US010053500B2

(12) United States Patent
Lai et al.

(10) Patent No.: US 10,053,500 B2
(45) Date of Patent: Aug. 21, 2018

(54) VARIANT OF ANTIHEMOPHILIC FACTOR VIII HAVING INCREASED SPECIFIC ACTIVITY

(71) Applicants: BAXALTA INCORPORATED, Bannockbun, IL (US); BAXALTA GMBH, Zug (CH)

(72) Inventors: Chee Kong Lai, Littleton, MA (US); Roddy Kevin Stafford, Shrewsbury, MA (US)

(73) Assignees: Baxalta Incorporated, Bannockburn, IL (US); Baxalta GmbH, Zug (CH)

(*) Notice: Subject to any disclaimer, the term of this patent is extended or adjusted under 35 U.S.C. 154(b) by 30 days.

(21) Appl. No.: 14/834,769

(22) Filed: Aug. 25, 2015

(65) Prior Publication Data

US 2015/0353625 A1    Dec. 10, 2015

Related U.S. Application Data

(62) Division of application No. 13/883,244, filed as application No. PCT/US2011/059297 on Nov. 4, 2011, now Pat. No. 9,150,637.

(60) Provisional application No. 61/410,437, filed on Nov. 5, 2010.

(51) Int. Cl.
*C07K 14/755* (2006.01)
*A61K 38/00* (2006.01)

(52) U.S. Cl.
CPC ............ *C07K 14/755* (2013.01); *A61K 38/00* (2013.01)

(58) Field of Classification Search
CPC .............................. C07K 14/755; A61K 38/00
See application file for complete search history.

(56) References Cited

U.S. PATENT DOCUMENTS

| | | | |
|---|---|---|---|
| 4,348,384 A | 9/1982 | Horikoshi et al. |
| 4,757,006 A | 7/1988 | Toole, Jr. et al. |
| 4,868,112 A | 9/1989 | Toole, Jr. |
| 5,364,771 A | 11/1994 | Lollar et al. |
| 5,384,132 A | 1/1995 | De Meere et al. |
| 5,563,045 A | 10/1996 | Pittman et al. |
| 5,565,427 A | 10/1996 | Freudenberg |
| 5,583,209 A | 12/1996 | Lollar et al. |
| 5,605,884 A | 2/1997 | Lee et al. |
| 5,663,060 A | 9/1997 | Lollar et al. |
| 5,733,873 A | 3/1998 | Osterberg et al. |
| 5,744,446 A | 4/1998 | Lollar et al. |
| 5,763,401 A | 6/1998 | Nayar |
| 5,859,204 A | 1/1999 | Lollar |
| 5,874,408 A | 2/1999 | Nayar |
| 5,888,974 A | 3/1999 | Lollar et al. |
| 5,925,739 A | 7/1999 | Spira et al. |
| 5,935,935 A | 8/1999 | Connelly et al. |
| 5,962,650 A | 10/1999 | Osterberg et al. |
| 5,972,885 A | 10/1999 | Spira et al. |
| 6,024,938 A | 2/2000 | Corbo et al. |
| 6,180,371 B1 | 1/2001 | Lollar |
| 6,200,560 B1 | 3/2001 | Couto et al. |
| 6,376,463 B1 | 4/2002 | Lollar |
| 6,458,563 B1 | 10/2002 | Lollar |
| 6,586,574 B1 | 7/2003 | Hansen |
| 6,642,028 B1 | 11/2003 | Ill et al. |
| 6,759,216 B1 | 7/2004 | Lollar |
| 6,770,744 B2 | 8/2004 | Lollar |
| 6,818,439 B1 | 11/2004 | Jolly et al. |
| 7,012,132 B2 | 3/2006 | Lollar |
| 7,033,791 B2 | 4/2006 | Lollar |
| 7,122,634 B2 | 10/2006 | Lollar |
| 7,560,107 B2* | 7/2009 | Lollar .................... A61K 38/37 424/94.64 |
| 7,576,181 B2 | 8/2009 | Lollar et al. |
| 7,576,182 B1 | 8/2009 | Goddard et al. |
| 7,790,680 B2 | 9/2010 | White et al. |
| 8,101,718 B2 | 1/2012 | Lollar et al. |
| 8,501,694 B2 | 8/2013 | Lollar et al. |
| 2004/0116345 A1 | 6/2004 | Besman et al. |
| 2004/0147436 A1 | 7/2004 | Kim et al. |
| 2004/0249134 A1 | 12/2004 | Lollar |
| 2005/0009148 A1 | 1/2005 | Lollar |
| 2005/0118684 A1 | 6/2005 | Lollar |
| 2005/0123997 A1* | 6/2005 | Lollar .................. C07K 14/755 435/7.1 |
| 2006/0014683 A1* | 1/2006 | Kaufman ............. C07K 14/755 530/383 |
| 2007/0135342 A1 | 6/2007 | Lollar |
| 2007/0173446 A1 | 7/2007 | Lollar et al. |
| 2009/0270329 A1 | 10/2009 | Lollar et al. |

(Continued)

FOREIGN PATENT DOCUMENTS

| | | |
|---|---|---|
| EP | 0182448 A2 | 5/1986 |
| EP | 0306968 A2 | 3/1989 |

(Continued)

OTHER PUBLICATIONS

Doering et al., 2002, High Level Expression of Recombinant Porcine Coagulation Factor VIII, The Journal of Biological Chemistry, 277(41): 38345-38349.*

Dooriss et al., 2009, Comparison of Factor VIII Transgenes Bioengineered for Improved Expression in Gene Therapy of Hemophilia A, Human Gene Therapy, 20: 465-478.*

Gangadharan et al., 2006, High-level expression of porcine factor VIII from genetically modified bone marrow-derived stem cells, Blood, 107(10): 3859-3864.*

T42763—porcine FVIII, http://pir.georgetown.edu/cgi-bin/nbrfget?uid=T42763, printed Jul. 12, 2017, last revision Dec. 31, 2004, 2 pages.*

(Continued)

*Primary Examiner* — Amber D Steele

(74) *Attorney, Agent, or Firm* — Morgan Lewis & Bockius LLP

(57) ABSTRACT

The present invention is in the field of hemophilia therapy. It relates to a new variant of antihemophilic factor VIII having increased specific activity in comparison to known factor VIII products.

20 Claims, 7 Drawing Sheets

(56) References Cited

U.S. PATENT DOCUMENTS

| | | |
|---|---|---|
| 2009/0271163 A1 | 10/2009 | Ngo et al. |
| 2009/0325881 A1 | 12/2009 | Lollar |
| 2010/0075891 A1 | 3/2010 | Ayalon-Soffer et al. |
| 2010/0081615 A1 | 4/2010 | Pan et al. |
| 2010/0120664 A1 | 5/2010 | Schulte et al. |

FOREIGN PATENT DOCUMENTS

| | | |
|---|---|---|
| JP | 62-81327 A | 4/1987 |
| JP | 64-85927 | 3/1989 |
| JP | 4-217630 | 8/1992 |
| JP | 08-99999 | 4/1996 |
| WO | WO-1989/009784 A1 | 10/1989 |
| WO | WO-1991/007438 A1 | 5/1991 |
| WO | WO-1993/020093 A1 | 10/1993 |
| WO | WO-1994/007510 A1 | 4/1994 |
| WO | WO-1994/011503 A2 | 5/1994 |
| WO | WO-1994/029471 A1 | 12/1994 |
| WO | WO-1995/024427 A1 | 9/1995 |
| WO | WO-1997/003191 A1 | 1/1997 |
| WO | WO-1997/003193 A1 | 1/1997 |
| WO | WO-1999/046274 A1 | 9/1999 |
| WO | WO-2000/048635 A1 | 8/2000 |
| WO | WO-2000/071141 A1 | 11/2000 |
| WO | WO-2001/003726 A1 | 1/2001 |
| WO | WO-2001/068109 A1 | 9/2001 |
| WO | WO-2003/080108 A1 | 10/2003 |
| WO | WO-2005/107776 A1 | 11/2005 |

OTHER PUBLICATIONS

Altschul et al., Basic Local Alignment Search Tool, *J. Mol. Biol.* 215: 403-10 (1990).
Altschul et al., Gapped BLAST and PSI-BLAST: A new generation of protein database search programs, *Nucl. Acids Res.*, 25(17): 3389-402 (1997).
Brandt, Measurement of factor VIII: A potential risk factor for vascular disease, *Arch. Pathol. Lab Med.* 117(1): 48-51 (1993).
Donath et al., Kinetics of factor VIII light-chain cleavage by thrombin and factor Xa. A regulatory role of the factor VIII heavy-chain region Lys713-Arg740. *Eur. J. Biochem.* 240: 365-72 (1996).
GenBank Accession No. AAR67709, B-domain deleted factor-VIII, dated Jul. 20, 1995.
GenBank Accession No. NP_999332, Coagulation factor VIII precursor [Sus scrofa], dated Mar. 12, 2010.
International Search Report and Written Opinion of the International Searching Authority, United States Patent and Trademark Office, issued in connection with International Application No. PCT/US2011/029297, dated Jul. 5, 2012.
Karlin et al., Applications and statistics for multiple high-scoring segments in molecular sequences, *Proc. Natl. Acad. Sci. USA*, 90(12): 5873-7 (1993).
Karlin et al., Methods for assessing the statistical significance of molecular sequence features by using general scoring schemes, *Proc. Natl. Acad. Sci. USA*, 87(6): 2264-8 (1990).
Langdell et al., Effect of antihemophilic factor on one-stage clotting tests: A presumptive test for hemophilia and a simple one-stage antihemophilic assay procedure, *J. Lab Clin. Med.* 41: 637-47 (1953).
Mertens et al., Biological activity of recombinant factor VIII variants lacking the central B-domain and the heavy-chain sequence Lys713-Arg740: discordant in vitro and in vivo activity, *Br. J.Haematol.* 85(1): 133-42 (1993).
Myers et al., Optimal alignments in linear space, *Comput. Appl. Biosci.* 4(1): 11-7 (1988).
National Committee for Clinical Laboratory Standards (NCCLS USA). Determination of factor coagulant activities; Approved guideline, NCCLS Document H-48-A; 17: 1-36 (1997).
Newell et al., Acidic residues C-terminal to the A2 domain facilitate thrombin-catalyzed activation of factor VIII. *Biochemistry*, 47(33): 8786-95 (2008).
Ngo et al., Crystal structure of human factor VIII: Implications for the formulation of the factor IXa-factor VIIIa complex. *Structure*, 16(4): 597-606 (2008).
Nogami et al., Exosite-interactive regions in the A1 and A2 domains of factor VIII facilitate thrombin-catalyzed cleavage of heavy chain. *J. Biol. Chem.*, 280(18): 18476-87 (2005).
Osterberg et al., Development of freeze-dried albumin-free formulation of recombinant factor VIII SQ. *Pharmaceut. Res.*, 14(7): 892-8 (1977).
Parker et al., Comparative immunogenicity of recombinant B domain-deleted porcine factor VIII and Hyate:C in hemophilia A mice presensitized to human factor VIII. *J. Thromb. Haemost.*, 2: 605-11 (2004).
Pearson et al., Improved tools for biological sequence comparison, *Proc. Natl. Acad. Sci. USA*, 85(8): 2444-8 (1988).
Pipe, Functional roles of the factor VIII B domain. *Haemophilia*, 15(6): 1187-96 (2009).
Preston et al., Quality control and factor VIII assays, *Haemophilia*, 4: 651-3 (1998).
Sabatino et.al., Recombinant canine B-domain-deleted FVIII exhibits high specific activity and is safe in the canine hemophilia A model, *Blood*, 114(20): 4562-5 (2009).
Supplemental European Search Report issued in counterpart European Patent Application No. 11838863.6, dated May 22, 2014.
Thim et al., Purification and characterization of a new recombinant factor VIII (N8). *Haemophilia*, 16(2): 349-59 (2009).
Toole et al., Molecular cloning of a cDNA encoding human antihaemophilic factor, *Nature*, 312(5992): 342-7 (1984).
Van Den Brink et al., Molecular analysis of human anti-factor VIII antibodies by V gene phage display identifies a new epitope in the acidic region following the A2 domain. *Blood*, 96(2): 540-5 (2000).
Vehar et al., Structure of human factor VIII, *Nature*, 312(5992): 337-42 (1984).
Wood et al., Expression of active human factor VIII from recombinant DNA clones, *Nature*, 312(5992): 330-7 (1984).

\* cited by examiner

```
                            1                                                          50
HUMFVIII (SEQ ID NO:13) ATRRYYLGAV ELSWDYMQSD .LGELPVDAR FPPRVPKSFP FNTSVVYKKT
PIGFVIII (SEQ ID NO:14) AIRRYYLGAV ELSWDYRQSE LLRELHVDTR FPATAPGALP LGPSVLYKKT
MURFVIII (SEQ ID NO:15) AIRRYYLGAV ELSWNYIQSD LLSVLHTDSR FLPRMSTSFP FNTSIMYKKT
CANFVIII (SEQ ID NO:16) ATRKYYLGAV ELSWDYMQSD LLSALHADTS FSSRVPGSLP LTTSVTYRKT 51                                                         100
HUMFVIII                LFVEFTDHLF NIAKPRPPWM GLLGPTIQAE VYDTVVITLK NMASHPVSLH
PIGFVIII                VFVEFTDQLF SVARPRPPWM GLLGPTIQAE VYDTVVVTLK NMASHPVSLH
MURFVIII                VFVEYKDQLF NIAKPRPPWM GLLGPTIWTE VHDTVVITLK NMASHPVSLH
CANFVIII                VFVEFTDDLF NIAKPRPPWM GLLGPTIQAE VYDTVVIVLK NMASHPVSLH 101                                                        150
HUMFVIII                AVGVSYWKAS EGAEYDDQTS QREKEDDKVF PGGSHTYVWQ VLKENGPMAS
PIGFVIII                AVGVSFWKSS EGAEYEDHTS QREKEDDKVL PGKSQTYVWQ VLKENGPTAS
MURFVIII                AVGVSYWKAS EGDEYEDQTS QMEKEDDKVF PGESHTYVWQ VLKENGPMAS
CANFVIII                AVGVSYWKAS EGAEYEDQTS QKEKEDDNVI PGESHTYVWQ VLKENGPMAS 151                                                        200
HUMFVIII                DPLCLTYSYL SHVDLVKDLN SGLIGALLVC REGSLAKEKT QTLHKFILLF
PIGFVIII                DPPCLTYSYL SHVDLVKDLN SGLIGALLVC REGSLTRERT QNLHEFVLLF
MURFVIII                DPPCLTYSYM SHVDLVKDLN SGLIGALLVC KEGSLSKERT QMLYQFVLLF
CANFVIII                DPPCLTYSYF SHVDLVKDLN SGLIGALLVC KEGSLAKERT QTLQEFVLLF 201                                                        250
HUMFVIII                AVFDEGKSWH SETKNSLMQD RDAASARAWP KMHTVNGYVN RSLPGLIGCH
PIGFVIII                AVFDEGKSWH SARNDSWTRA MDPAPARAQP AMHTVNGYVN RSLPGLIGCH
MURFVIII                AVFDEGKSWH SETNDSYTQS MDSASARDWP KMHTVNGYVN RSLPGLIGCH
CANFVIII                AVFDEGKSWH SETNASLTQ. .....AEAQH ELHTINGYVN RSLPGLTVCH 251                                                        300
HUMFVIII                RKSVYWHVIG MGTTPEVHSI FLEGHTFLVR NHRQASLEIS PITFLTAQTL
PIGFVIII                KKSVYWHVIG MGTSPEVHSI FLEGHTFLVR HHRQASLEIS PLTFLTAQTF
MURFVIII                RKSVYWHVIG MGTTPEIHSI FLEGHTFFVR NHRQASLEIS PITFLTAQTL
CANFVIII                KRSVYWHVIG MGTTPEVHSI FLEGHTFLVR NHRQASLEIS PITFLTAQTF 301                                                        350
HUMFVIII                LMDLGQFLLF CHISSHQHDG MEAYVKVDSC PEEPQLRMK. NNEEAEDYDD
PIGFVIII                LMDLGQFLLF CHISSHHHGG MEAHVRVESC AEEPQLRRK. ADEE.EDYDD
MURFVIII                LIDLGQFLLF CHISSHKHDG MEAYVKVDSC PEESQWQKKN NNEEMEDYDD
CANFVIII                LMDLGQFLLF CHIPSHQHDG MEAYVKVDSC PEEPQLRMK. NNED.KDYDD 351                                                        400
HUMFVIII                DLTDSEMDVV RFDDDNSPSF IQIRSVAKKH PKTWVHYIAA EEEDWDYAPL
PIGFVIII                NLYDSDMDVV RLDGDDVSPF IQIRSVAKKH PKTWVHYISA EEEDWDYAPA
MURFVIII                DLY.SEMDMF TLDYD.SSPF IQIRSVAKKY PKTWIHYISA EEEDWDYAPS
CANFVIII                GLYDSDMDVV SFDDDSSSPF IQIRSVAKKH PKTWVHYIAA EEEDWDYAPS 401                                                        450
HUMFVIII                VLAPDDRSYK SQYLNNGPQR IGRKYKKVRF MAYTDETFKT REAIQHESGI
PIGFVIII                VPSPSDRSYK SLYLNSGPQR IGRKYKKARF VAYTDVTFKT RKAIPYESGI
MURFVIII                VPTSDNGSYK SQYLSNGPHR IGRKYKKVRF IAYTDETFKT RETIQHESGL
CANFVIII                GPTPNDRSHK NLYLNNGPQR IGKKYKKVRF VAYTDETFKT REAIQYESGI 451                                                        500
HUMFVIII                LGPLLYGEVG DTLLIIFKNQ ASRPYNIYPH GITDVRPLYS RRLPKGVKHL
PIGFVIII                LGPLLYGEVG DTLLIIFKNK ASRPYNIYPH GITDVSALHP GRLLKGWKHL
MURFVIII                LGPLLYGEVG DTLLIIFKNQ ASRPYNIYPH GITDVSPLHA RRLPRGIKHV
CANFVIII                LGPLLYGEVG DTLLIIFKNQ ASRPYNIYPH GINYVTPLHT GRLPKGVKHL
```

Fig. 2a

```
            501                                                       550
HUMFVIII    KDFPILPGEI  FKYKWTVTVE  DGPTKSDPRC  LTRYYSSFVN  MERDLASGLI
PIGFVIII    KDMPILPGET  FKYKWTVTVE  DGPTKSDPRC  LTRYYSSSIN  LEKDLASGLI
MURFVIII    KDLPIHPGEI  FKYKWTVTVE  DGPTKSDPRC  LTRYYSSFIN  PERDLASGLI
CANFVIII    KDMPILPGEI  FKYKWTVTVE  DGPTKSDPRC  LTRYYSSFIN  LERDLASGLI 551                                                       600
HUMFVIII    GPLLICYKES  VDQRGNQIMS  DKRNVILFSV  FDENRSWYLT  ENIQRFLPNP
PIGFVIII    GPLLICYKES  VDQRGNQMMS  DKRNVILFSV  FDENQSWYLA  ENIQRFLPNP
MURFVIII    GPLLICYKES  VDQRGNQMMS  DKRNVILFSI  FDENQSWYIT  ENMQRFLPNA
CANFVIII    GPLLICYKES  VDQRGNQMMS  DKRNVILFSV  FDENRSWYLT  ENMQRFLPNA 601                                                       650
HUMFVIII    AGVQLEDPEF  QASNIMHSIN  GYVFDSLQLS  VCLHEVAYWY  ILSIGAQTDF
PIGFVIII    DGLQPQDPEF  QASNIMHSIN  GYVFDSLQLS  VCLHEVAYWY  ILSVGAQTDF
MURFVIII    AKTQPQDPGF  QASNIMHSIN  GYVFDSLELT  VCLHEVAYWH  ILSVGAQTDF
CANFVIII    DVVQPHDPEF  QLSNIMHSIN  GYVFDNLQLS  VCLHEVAYWY  ILSVGAQTDF 651                                                       700
HUMFVIII    LSVFFSGYTF  KHKMVYEDTL  TLFPFSGETV  FMSMENPGLW  ILGCHNSDFR
PIGFVIII    LSVFFSGYTF  KHKMVYEDTL  TLFPFSGETV  FMSMENPGLW  VLGCHNSDLR
MURFVIII    LSIFFSGYTF  KHKMVYEDTL  TLFPFSGETV  FMSMENPGLW  VLGCHNSDFR
CANFVIII    LSVFFSGYTF  KHKMVYEDTL  TLFPFSGETV  FMSMENPGLW  VLGCHNSDFR 701                                                       750
HUMFVIII    NRGMTALLKV  SSCDKNTGDY  YEDSYEDISA  YLLSKNNAIE  PRSFSQNSRH
PIGFVIII    NRGMTALLKV  YSCDRDIGDY  YDNTYEDIPG  FLLSGKNVIE  PRSFAQNSRH
MURFVIII    KRGMTALLKV  SSCDKSTSDY  YEEIYEDIPT  QLVNENNVID  PRSFFQNTNH
CANFVIII    NRGMTALLKV  SSCNRNIDDY  YEDTYEDIPT  PLLNENNVIK  PRSFSQNSRH 751                                                       800
HUMFVIII    PSTRQKQFNA  TTIPENDIEK  TDPWFAHRTP  MPKIQNVSSS  DLLMLLRQS.
PIGFVIII    PSASQKQFQT  ITSPEDDVE.  LDPQSGERTQ  ALEELSVPSG  DGSMLLGQN.
MURFVIII    PNTRKKKFKD  STIPKNDMEK  IEPQFEEIAE  MLKVQSVSVS  DMLMLLGQSH
CANFVIII    PSTKEKQLKA  TTTPENDIEK  IDLQSGERTQ  LIKAQSVSSS  DLLMLLGQN.

801                                                       850
HUMFVIII    PTPHGLSLSD  LQEAKYETFS  DDPSPGAIDS  NNSLSEMTHF  RPQLHHSGDM
PIGFVIII    PAPHGSSSSD  LQEARNE..A  DDYLPGARER  NTAFSAAARL  RPELHHSAER
MURFVIII    PTPHGLFLSD  GQEAIYEAIH  DDHSPNAIDS  NEGPSKVTQL  RPESHHSEKI
CANFVIII    PTPRGLFLSD  LREA..TDRA  DDHSRGAIER  NKGPPEVASL  RPELRHSEDR 851                                                       900
HUMFVIII    VFTPESGLQL  RLNEKLGTTA  ATELKKLDFK  VSSTSNNLI.  .STIPSDNLA
PIGFVIII    VLTPEPE...  ..........  .KELKKLDSK  MSSSSDLLKT  SPTIPSDTLS
MURFVIII    VFTPQPGLQL  RSNKSLETTI  EVKWKKLGLQ  VSSLPSNLMT  .TTILSDNLK
CANFVIII    EFTPEPELQL  RLNENLGTNT  TVELKKLDLK  ISSSSDSLMT  SPTIPSDKLA 901                                                       950
HUMFVIII    AGTDNTSSLG  PPSMPVHYDS  QLDTTLFGKK  SSPLTESGGP  LSLSEENNDS
PIGFVIII    AETERTHSLG  PPHPQVNFRS  QLGAIVLGKN  SSHFIGAGVP  LGSTEED...
MURFVIII    ATFEKTDSSG  FPDMPVHSSS  KLSTTAFGKK  AYSLVGSHVP  LNASEENSDS
CANFVIII    AATEKTGSLG  PPNMSVHFNS  HLGTIVFGNN  SSHLIQSGVP  LELSEEDNDS 951                                                       1000
HUMFVIII    KLLESGLMNS  QESSWGKNVS  STESGRLFKG  KRAHGPALLT  KDNALFKVSI
PIGFVIII    ..........  HESSLGENVS  PVESDGIFEK  ERAHGPASLT  KDDVLFKVNI
MURFVIII    NILDSTLMYS  QESLPRDNIL  SIENDRLLRE  KRFHGIALLT  KDNTLFKDNV
CANFVIII    KLLEAPLMNI  QESSLRENVL  SMESNRLFKE  ERIRGPASLI  KDNALFKVNI
```

Fig. 2b

```
              1001                                                              1050
HUMFVIII      SLLKTNKTSN  NSATNRKTHI  DGPSLLIENS  PSVWQNI.LE  SDTEFKKVTP
PIGFVIII      SLVKTNKARV  YLKTNRKIHI  DDAALLTENR  ASA.......  ..........
MURFVIII      SLMKTNKTYN  HSTTNEKLHT  ESPT.SIENS  TTDLQDAILK  VNSEIQEVTA
CANFVIII      SSVKTNRAPV  NLTTNRKTRV  AIPTLLIENS  TSVWQDIMLE  RNTEFKEVTS 1051                                                              1100
HUMFVIII      LIHDRMLMDK  NATALRLNHM  SNKTTSSKNM  EMVQQKKEGP  IPPDAQNPDM
PIGFVIII      .....TFMDK  NTTASGLNHV  SN........  ..........  ..........
MURFVIII      LIHDGTLLGK  NSTYLRLNHM  LNRTTSTKNK  DIFHRKDEDP  IPQDEENTIM
CANFVIII      LIHNETFMDR  NTTALGLNHV  SNKTTLSKNV  EMAHQKKEDP  VPLRAENPDL 1101                                                              1150
HUMFVIII      SFFKMLFLPE  SARWIQRTHG  KNSLNSGQGP  SPKQLVSLGP  EKSVEGQNFL
PIGFVIII      ..........  ...WIKGPLG  KNPLSSERGP  SPELLTSSGS  GKSVKGQSSG
MURFVIII      PFSKMLFLSE  SSNWFKKTNG  NNSLNSEQEH  SPKQLVYLMF  KKYVKNQSFL
CANFVIII      SSSKIPFLPD  WI....KTHG  KNSLSSEQRP  SPKQLTSLGS  EKSVKDQNFL 1151                                                              1200
HUMFVIII      SEKNKVVVGK  GEFTKDVGLK  EMVFPSSRNL  FLTNLDNLHE  NNTHNQEKKI
PIGFVIII      QGRIRVAVEE  EELSKG...K  EMMLPNSELT  FLTNSADVQG  NDTHSQGKKS
MURFVIII      SEKNKVTVEQ  DGFTKNIGLK  DMAFPHNMSI  FLTTLSNVHE  NGRPHNQEKNI
CANFVIII      SE.EKVVVGE  DEFTKDTELQ  E.IFPNNKSI  FFANLANVQE  NDTYNQEKKS 1201                                                              1250
HUMFVIII      QEEIEKKETL  IQENVVLPQI  HTVTGTKNFM  KNLFLLSTRQ  NVEGSYDGAY
PIGFVIII      REEMERREKL  VQEKVDLPQV  YTATGTKNFL  RNIFHQSTEP  SVEGFDGGSH
MURFVIII      QEEIE.KEAL  IEEKVVLPQV  HEATGSKNFL  KDILILGTRQ  NISLYE..VH
CANFVIII      PEEIERKEKL  TQENVALPQA  HTMIGTKNFL  KNLFLLSTKQ  NVAGLEEQPY 1251                                                              1300
HUMFVIII      APVLQDFRSL  NDSTNRTKKH  TAHFSKKG..  EEENLEGLGN  QTKQIVEKYA
PIGFVIII      APVPQDSRSL  NDSAERAETH  IAHFSAIR..  EEAPLEAPGN  RT........
MURFVIII      VPVLQNITSI  NNSTNTVQIH  MEHFFKRRKD  KETNSEGLVN  KTREMVKNY.
CANFVIII      TPILQDTRSL  NDSPHSEGIH  MANFSKIR..  EEANLEGLGN  QTNQMVERFP 1301                                                              1350
HUMFVIII      CTTRISPNTS  QQNFVTQRSK  RALKQFRLPL  EETELEKRII  VDDTSQWSK
PIGFVIII      ......GPG   PRSAVPRRVK  QSLKQIRLPL  EEIKPERGVV  LNATSTRWS.
MURFVIII      .........PS  QKNITTQRSK  RALGQFRL..  ..........  ....STQWLK
CANFVIII      STTRMSSNAS  QH.VITQRGK  RSLKQPRLSQ  GEIKFERKVI  ANDTSTQWSK 1351                                                              1400
HUMFVIII      NMKHLTPSTL  TQIDYNEKEK  GAITQSPLSD  CLTRSHSIPQ  ANRSPLPIAK
PIGFVIII      ..........  ..........  ..........  ..........  ..........
MURFVIII      TINCSTQCII  KQIDHSKEMK  KFITKSSLSD  SSVIK.STTQ  TNSSDSHIVK
CANFVIII      NMNYLAQGTL  TQIEYNEKEK  RAITQSPLSD  CSMRNHVTIQ  MNDSALPVAK 1401                                                              1450
HUMFVIII      VSSFPSIRPI  YLTRVLFQDN  SSHLPAAS..  ..YRKKDSGV  QESSHFLQGA
PIGFVIII      ..........  ..........  ..........  ..........  .ESSPILQGA
MURFVIII      TSAFP...PI  DLKRSPFQNK  FSHVQASSYI  YDFKTKSSRI  QESNNFLKET
CANFVIII      ESASPSVRHT  DLTKIPSQHN  SSHLPASACN  YTFRERTSGV  QEGSHFLQEA 1451                                                              1500
HUMFVIII      KKNNLSLAIL  TLEMGDQRE   VGSLGTSATN  SVTYKKVENT  VLPKPDLPKT
PIGFVIII      KRNNLSLPFL  TLEMAGGQGK  ISALGKSAAG  PLASGKLEKA  VLSSAGLSEA
MURFVIII      KINNPSLAIL  PWNMFIDQGK  FTSPGKSNTN  SVTYKKRENI  IFLKPTLPEE
CANFVIII      KRNNLSLAFV  TLGITEGQGK  FSSLGKSATN  QPMYKKLENT  VLLQPGLSET
```

Fig. 2c

```
              1501                                                        1550
HUMFVIII   SGKVELLPKV  HIYQKDLFPT  ETSNGSPGHL  DLVEGSLLQG  TEGAIKWNEA
PIGFVIII   SGKAEFLPKV  RVHREDLLPQ  KTSNVSCAHG  DLGQEIFLQK  TRGPVNLNKV
MURFVIII   SGKIELLPQV  SIQEEEILPT  ETSHGSPGHL  NLMKEVFLQK  IQGPTKWNKA
CANFVIII   SDKVELLSQV  HVDQEDSFPT  KTSNDSPGHL  DLMGKIFLQK  TQGPVKMNKT 1551                                                        1600
HUMFVIII   NRPGKVPFLR  VATESSAKTP  SKLLDPLAWD  NHYGTQIPKE  EWKSQEKSPE
PIGFVIII   NRPG......  .......RTP  SKLLGPPM..  ........PK  EWESLEKSPK
MURFVIII   KRHGES..IK  GKTESSKNTR  SKLLNHHAWD  YHYAAQIPKD  MWKSKEKSPE
CANFVIII   NSPGKVPFLK  WATESSEKIP  SKLLGVLAWD  NHYDTQIPSE  EWKSQKKSQT 1601                                                        1650
HUMFVIII   KTAFKKKDTI  .LSLNACESN  HAIAAINEGQ  NKPEIEVTWA  KQGRTERLCS
PIGFVIII   STALRTKDII  SLPLDRHESN  HSIAAKNEGQ  AETQREAAWT  KQGGPGRLCA
MURFVIII   IISIKQEDTI  .LSLRPHGNS  HSIGA.NEKQ  NWPQRETTWV  KQGQTQRTCS
CANFVIII   NTAFKRKDTI  .LPLGPCENN  DSTAAINEGQ  DKPQREAMWA  KQGEPGRLCS 1651                                                        1700
HUMFVIII   QNPPVLKRHQ  REITRTTLQS  DQEEIDYDDT  ISVEMKKEDF  DIYDEDENQS
PIGFVIII   DKPPVLRRHQ  RDISLPTFQP  EEDKMDYDDI  FSTETKGEDF  DIYGEDENQD
MURFVIII   QIPPVLKRHQ  RELS..AFQS  EQEATDYDDA  ITIETI.EDF  DIYSEDIKQG
CANFVIII   QNPPVSKHHQ  REITVTTLQP  EEDKFEYDDT  FSIEMKREDF  DIYGDYENQG 1701                                                        1750
HUMFVIII   PRSFQKKTRH  YFIAAVERLW  DYGMSSSPHV  LRNRAQSGSV  PQFKKVVFQE
PIGFVIII   PRSFQKRTRH  YFIAAVEQLW  DYGMSESPRA  LRNRAQNGEV  PRFKKVVFRE
MURFVIII   PRSFQQKTRH  YFIAAVERLW  DYGMSTS.HV  LRNRYQSDNV  PQFKKVVFQE
CANFVIII   LRSFQKKTRH  YFIAAVERLW  DYGMSRSPHI  LRNRAQSGDV  QQFKKVVFQE 1751                                                        1800
HUMFVIII   FTDGSFTQPL  YRGELNEHLG  LLGPYIRAEV  EDNIMVTFRN  QASRPYSFYS
PIGFVIII   FADGSFTQPS  YRGELNKHLG  LLGPYIRAEV  EDNIMVTFKN  QASRPYSFYS
MURFVIII   FTDGSFSQPL  YRGELNEHLG  LLGPYIRAEV  EDNIMVTFKN  QASRPYSFYS
CANFVIII   FTDGSFTQPL  YRGELNEHLG  LLGPYIRAEV  EDNIVVTFKN  QASRPYSFYS 1801                                                        1850
HUMFVIII   SLISYEEDQR  QGAEPRKNFV  KPNETKTYFW  KVQHHMAPTK  DEFDCKAWAY
PIGFVIII   SLISYPDDQE  QGAEPRHNFV  QPNETRTYFW  KVQHHMAPTE  DEFDCKAWAY
MURFVIII   SLISYKEDQ.  RGEEPRRNFV  KPNETKIYFW  KVQHHMAPTE  DEFDCKAWAY
CANFVIII   SLISYDEDEG  QGAEPRRKFV  NPNETKIYFW  KVQHHMAPTK  DEFDCKAWAY 1851                                                        1900
HUMFVIII   FSDVDLEKDV  HSGLIGPLLV  CHTNTLNPAH  GRQVTVQEFA  LFFTIFDETK
PIGFVIII   FSDVDLEKDV  HSGLIGPLLI  CRANTLNAAH  GRQVTVQEFA  LFFTIFDETK
MURFVIII   FSDVDLERDM  HSGLIGPLLI  CHANTLNPAH  GRQVSVQEFA  LLFTIFDETK
CANFVIII   FSDVDLEKDV  HSGLIGPLLI  CRSNTLNPAH  GRQVTVQEFA  LVFTIFDETK 1901                                                        1950
HUMFVIII   SWYFTENMER  NCRAPCNIQM  EDPTFKENYR  FHAINGYIMD  TLPGLVMAQD
PIGFVIII   SWYFTENVER  NCRAPCHLQM  EDPTLKENYR  FHAINGYVMD  TLPGLVMAQN
MURFVIII   SWYFTENVKR  NCKTPCNFQM  EDPTLKENYR  FHAINGYVMD  TLPGLVMAQD
CANFVIII   SWYFTENLER  NCRAPCNVQK  EDPTLKENFR  FHAINGYVKD  TLPGLVMAQD 1951                                                        2000
HUMFVIII   QRIRWYLLSM  GSNENIHSIH  FSGHVFTVRK  KEEYKMALYN  LYPGVFETVE
PIGFVIII   QRIRWYLLSM  GSNENIHSIH  FSGHVFSVRK  KEEYKMAVYN  LYPGVFETVE
MURFVIII   QRIRWYLLSM  GNNENIQSIH  FSGHVFTVRK  KEEYKMAVYN  LYPGVFETLE
CANFVIII   QKVRWYLLSM  GSNENIHSIH  FSGHVFTVRK  KEEYKMAVYN  LYPGVFETVE
```

Fig. 2d

```
                2001                                                    2050
HUMFVIII    MLPSKAGIWR  VECLIGEHLH  AGMSTLFLVY  SNKCQTPLGM  ASGHIRDFQI
PIGFVIII    MLPSKVGIWR  IECLIGEHLQ  AGMSTTFLVY  SKECQAPLGM  ASGRIRDFQI
MURFVIII    MIPSRAGIWR  VECLIGEHLQ  AGMSTLFLVY  SKQCQIPLGM  ASGSIRDFQI
CANFVIII    MLPSQVGIWR  IECLIGEHLQ  AGMSTLFLVY  SKKCQTPLGM  ASGHIRDFQI 2051                                                    2100
HUMFVIII    TASGQYGQWA  PKLARLHYSG  SINAWSTKEP  FSWIKVDLLA  PMIIHGIKTQ
PIGFVIII    TASGQYGQWA  PKLARLHYSG  SINAWSTKDP  HSWIKVDLLA  PMIIHGIMTQ
MURFVIII    TASGHYGQWA  PNLARLHYSG  SINAWSTKEP  FSWIKVDLLA  PMIVHGIKTQ
CANFVIII    TASGQYGQWA  PKLARLHYSG  SINAWSTKDP  FSWIKVDLLA  PMIIHGIMTQ 2101                                                    2150
HUMFVIII    GARQKFSSLY  ISQFIIMYSL  DGKKWQTYRG  NSTGTLMVFF  GNVDSSGIKH
PIGFVIII    GARQKFSSLY  ISQFIIMYSL  DGRNWQSYRG  NSTGTLMVFF  GNVDASGIKH
MURFVIII    GARQKFSSLY  ISQFIIMYSL  DGKKWLSYQG  NSTGTLMVFF  GNVDSSGIKH
CANFVIII    GARQKFSSLY  VSQFIIMYSL  DGNKWHSYRG  NSTGTLMVFF  GNVDSSGIKH 2151                                                    2200
HUMFVIII    NIFNPPIIAR  YIRLHPTHYS  IRSTLRMELM  GCDLNSCSMP  LGMESKAISD
PIGFVIII    NIFNPPIVAR  YIRLHPTHYS  IRSTLRMELM  GCDLNSCSMP  LGMQNKAISD
MURFVIII    NSFNPPIIAR  YIRLHPTHSS  IRSTLRMELM  GCDLNSCSIP  LGMESKVISD
CANFVIII    NIFNPPIIAQ  YIRLHPTHYS  IRSTLRMELL  GCDFNSCSMP  LGMESKAISD 2201                                                    2250
HUMFVIII    AQITASSYFT  NMFATWSPSK  ARLHLQGRSN  AWRPQVNNPK  EWLQVDFQKT
PIGFVIII    SQITASSHLS  NIFATWSPSQ  ARLHLQGRTN  AWRPRVSSAE  EWLQVDLQKT
MURFVIII    TQITASSYFT  NMFATWSPSQ  ARLHLQGRTN  AWRPQVNDPK  QWLQVDLQKT
CANFVIII    AQITASSYLS  SMLATWSPSQ  ARLHLQGRTN  AWRPQANNPK  EWLQVDFRKT 2251                                                    2300
HUMFVIII    MKVTGVTTQG  VKSLLTSMYV  KEFLISSSQD  GHQWTLFFQN  GKVKVFQGNQ
PIGFVIII    VKVTGITTQG  VKSLLSSMYV  KEFLVSSSQD  GREWTLFLQD  GHTKVFQGNQ
MURFVIII    MKVTGIITQG  VKSLFTSMFV  KEFLISSSQD  GHHWTQILYN  GKVKVFQGNQ
CANFVIII    MKVTGITTQG  VKSLLISMYV  KEFLISSSQD  GHNWTLFLQN  GKVKVFQGNR 2301                                          2345
HUMFVIII    DSFTPVVNSL  DPPLLTRYLR  IHPQSWVHQI  ALRMEVLGCE  AQDLY
PIGFVIII    DSSTPVVNAL  DPPLFTRYLR  IHPTSWAQHI  ALRLEVLGCE  AQDLY
MURFVIII    DSSTPMMNSL  DPPLLTRYLR  IHPQIWEHQI  ALRLEILGCE  AQQQY
CANFVIII    DSSTPVRNRL  EPPLVARYVR  LHPQSWAHHI  ALRLEVLGCD  TQQPA
```

Fig. 2e

SEQUENCE LISTING

<160> NUMBER OF SEQ ID NOS: 16

<210> SEQ ID NO 1
<211> LENGTH: 1421
<212> TYPE: PRT
<213> ORGANISM: sus scrofa

<400> SEQUENCE: 1

Ala Ile Arg Arg Tyr Tyr Leu Gly Ala Val Glu Leu Ser Trp Asp Tyr
1               5                   10                  15

Arg Gln Ser Glu Leu Leu Arg Glu Leu His Val Asp Thr Arg Phe Pro
            20                  25                  30

Ala Thr Ala Pro Gly Ala Leu Pro Leu Gly Pro Ser Val Leu Tyr Lys
        35                  40                  45

Lys Thr Val Phe Val Glu Phe Thr Asp Gln Leu Phe Ser Val Ala Arg
    50                  55                  60

Pro Arg Pro Pro Trp Met Gly Leu Leu Gly Pro Thr Ile Gln Ala Glu
65                  70                  75                  80

Val Tyr Asp Thr Val Val Val Thr Leu Lys Asn Met Ala Ser His Pro
                85                  90                  95

Val Ser Leu His Ala Val Gly Val Ser Phe Trp Lys Ser Ser Glu Gly
            100                 105                 110

Ala Glu Tyr Glu Asp His Thr Ser Gln Arg Glu Lys Glu Asp Asp Lys
        115                 120                 125

Val Leu Pro Gly Lys Ser Gln Thr Tyr Val Trp Gln Val Leu Lys Glu
    130                 135                 140

Asn Gly Pro Thr Ala Ser Asp Pro Pro Cys Leu Thr Tyr Ser Tyr Leu
145                 150                 155                 160

Ser His Val Asp Leu Val Lys Asp Leu Asn Ser Gly Leu Ile Gly Ala
                165                 170                 175

Leu Leu Val Cys Arg Glu Gly Ser Leu Thr Arg Glu Arg Thr Gln Asn
            180                 185                 190

Leu His Glu Phe Val Leu Leu Phe Ala Val Phe Asp Glu Gly Lys Ser
        195                 200                 205

Trp His Ser Ala Arg Asn Asp Ser Trp Thr Arg Ala Met Asp Pro Ala
    210                 215                 220

Pro Ala Arg Ala Gln Pro Ala Met His Thr Val Asn Gly Tyr Val Asn
225                 230                 235                 240

```
Arg Ser Leu Pro Gly Leu Ile Gly Cys His Lys Lys Ser Val Tyr Trp
            245                 250                 255

His Val Ile Gly Met Gly Thr Ser Pro Glu Val His Ser Ile Phe Leu
            260                 265                 270

Glu Gly His Thr Phe Leu Val Arg His His Arg Gln Ala Ser Leu Glu
            275                 280                 285

Ile Ser Pro Leu Thr Phe Leu Thr Ala Gln Thr Phe Leu Met Asp Leu
            290                 295                 300

Gly Gln Phe Leu Leu Phe Cys His Ile Ser Ser His His Gly Gly
305                 310                 315                 320

Met Glu Ala His Val Arg Val Glu Ser Cys Ala Glu Glu Pro Gln Leu
                325                 330                 335

Arg Arg Lys Ala Asp Glu Glu Asp Tyr Asp Asp Asn Leu Tyr Asp
                340                 345                 350

Ser Asp Met Asp Val Val Arg Leu Asp Gly Asp Val Ser Pro Phe
                355                 360                 365

Ile Gln Ile Arg Ser Val Ala Lys Lys His Pro Lys Thr Trp Val His
                370                 375                 380

Tyr Ile Ser Ala Glu Glu Asp Trp Asp Tyr Ala Pro Ala Val Pro
385                 390                 395                 400

Ser Pro Ser Asp Arg Ser Tyr Lys Ser Leu Tyr Leu Asn Ser Gly Pro
                405                 410                 415

Gln Arg Ile Gly Arg Lys Tyr Lys Lys Ala Arg Phe Val Ala Tyr Thr
                420                 425                 430

Asp Val Thr Phe Lys Thr Arg Lys Ala Ile Pro Tyr Glu Ser Gly Ile
                435                 440                 445

Leu Gly Pro Leu Leu Tyr Gly Glu Val Gly Asp Thr Leu Leu Ile Ile
450                 455                 460

Phe Lys Asn Lys Ala Ser Arg Pro Tyr Asn Ile Tyr Pro His Gly Ile
465                 470                 475                 480

Thr Asp Val Ser Ala Leu His Pro Gly Arg Leu Leu Lys Gly Trp Lys
                485                 490                 495

His Leu Lys Asp Met Pro Ile Leu Pro Gly Glu Thr Phe Lys Tyr Lys
                500                 505                 510

Trp Thr Val Thr Val Glu Asp Gly Pro Thr Lys Ser Asp Pro Arg Cys
                515                 520                 525

Leu Thr Arg Tyr Tyr Ser Ser Ser Ile Asn Leu Glu Lys Asp Leu Ala
530                 535                 540

Ser Gly Leu Ile Gly Pro Leu Leu Ile Cys Tyr Lys Glu Ser Val Asp
545                 550                 555                 560

Gln Arg Gly Asn Gln Met Met Ser Asp Lys Arg Asn Val Ile Leu Phe
                565                 570                 575

Ser Val Phe Asp Glu Asn Gln Ser Trp Tyr Leu Ala Glu Asn Ile Gln
                580                 585                 590

Arg Phe Leu Pro Asn Pro Asp Gly Leu Gln Pro Gln Asp Pro Glu Phe
                595                 600                 605

Gln Ala Ser Asn Ile Met His Ser Ile Asn Gly Tyr Val Phe Asp Ser
                610                 615                 620

Leu Gln Leu Ser Val Cys Leu His Glu Val Ala Tyr Trp Tyr Ile Leu
625                 630                 635                 640

Ser Val Gly Ala Gln Thr Asp Phe Leu Ser Val Phe Phe Ser Gly Tyr
                645                 650                 655
```

-continued

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
        675                 680                 685

Val Leu Gly Cys His Asn Ser Asp Leu Arg Asn Arg Gly Met Thr Ala
    690                 695                 700

Leu Leu Lys Val Tyr Ser Cys Asp Arg Ser Phe Ala Gln Asn Ser Arg
705                 710                 715                 720

Pro Pro Ser Ala Ser Ala Pro Lys Pro Val Leu Arg Arg His Gln
                725                 730                 735

Arg Asp Ile Ser Leu Pro Thr Phe Gln Pro Glu Glu Asp Lys Met Asp
                740                 745                 750

Tyr Asp Asp Ile Phe Ser Thr Glu Thr Lys Gly Glu Asp Phe Asp Ile
        755                 760                 765

Tyr Gly Glu Asp Glu Asn Gln Asp Pro Arg Ser Phe Gln Lys Arg Thr
    770                 775                 780

Arg His Tyr Phe Ile Ala Ala Val Glu Gln Leu Trp Asp Tyr Gly Met
785                 790                 795                 800

Ser Glu Ser Pro Arg Ala Leu Arg Asn Arg Ala Gln Asn Gly Glu Val
                805                 810                 815

Pro Arg Phe Lys Lys Val Val Phe Arg Glu Phe Ala Asp Gly Ser Phe
                820                 825                 830

Thr Gln Pro Ser Tyr Arg Gly Glu Leu Asn Lys His Leu Gly Leu Leu
        835                 840                 845

Gly Pro Tyr Ile Arg Ala Glu Val Glu Asp Asn Ile Met Val Thr Phe
    850                 855                 860

Lys Asn Gln Ala Ser Arg Pro Tyr Ser Phe Tyr Ser Ser Leu Ile Ser
865                 870                 875                 880

Tyr Pro Asp Asp Gln Glu Gln Gly Ala Glu Pro Arg His Asn Phe Val
                885                 890                 895

Gln Pro Asn Glu Thr Arg Thr Tyr Phe Trp Lys Val Gln His His Met
                900                 905                 910

Ala Pro Thr Glu Asp Glu Phe Asp Cys Lys Ala Trp Ala Tyr Phe Ser
        915                 920                 925

Asp Val Asp Leu Glu Lys Asp Val His Ser Gly Leu Ile Gly Pro Leu
    930                 935                 940

Leu Ile Cys Arg Ala Asn Thr Leu Asn Ala Ala His Gly Arg Gln Val
945                 950                 955                 960

Thr Val Gln Glu Phe Ala Leu Phe Phe Thr Ile Phe Asp Glu Thr Lys
                965                 970                 975

Ser Trp Tyr Phe Thr Glu Asn Val Glu Arg Asn Cys Arg Ala Pro Cys
        980                 985                 990

His Leu Gln Met Glu Asp Pro Thr Leu Lys Glu Asn Tyr Arg Phe His
    995                 1000                 1005

Ala Ile Asn Gly Tyr Val Met Asp Thr Leu Pro Gly Leu Val Met
    1010                 1015                 1020

Ala Gln Asn Gln Arg Ile Arg Trp Tyr Leu Leu Ser Met Gly Ser
    1025                 1030                 1035

Asn Glu Asn Ile His Ser Ile His Phe Ser Gly His Val Phe Ser
    1040                 1045                 1050

Val Arg Lys Lys Glu Glu Tyr Lys Met Ala Val Tyr Asn Leu Tyr
    1055                 1060                 1065

Pro Gly Val Phe Glu Thr Val Glu Met Leu Pro Ser Lys Val Gly

```
              1070                1075                1080
Ile Trp Arg Ile Glu Cys Leu Ile Gly Glu His Leu Gln Ala Gly
    1085                1090                1095
Met Ser Thr Thr Phe Leu Val Tyr Ser Lys Glu Cys Gln Ala Pro
    1100                1105                1110
Leu Gly Met Ala Ser Gly Arg Ile Arg Asp Phe Gln Ile Thr Ala
    1115                1120                1125
Ser Gly Gln Tyr Gly Gln Trp Ala Pro Lys Leu Ala Arg Leu His
    1130                1135                1140
Tyr Ser Gly Ser Ile Asn Ala Trp Ser Thr Lys Asp Pro His Ser
    1145                1150                1155
Trp Ile Lys Val Asp Leu Leu Ala Pro Met Ile Ile His Gly Ile
    1160                1165                1170
Met Thr Gln Gly Ala Arg Gln Lys Phe Ser Ser Leu Tyr Ile Ser
    1175                1180                1185
Gln Phe Ile Ile Met Tyr Ser Leu Asp Gly Arg Asn Trp Gln Ser
    1190                1195                1200
Tyr Arg Gly Asn Ser Thr Gly Thr Leu Met Val Phe Phe Gly Asn
    1205                1210                1215
Val Asp Ala Ser Gly Ile Lys His Asn Ile Phe Asn Pro Pro Ile
    1220                1225                1230
Val Ala Arg Tyr Ile Arg Leu His Pro Thr His Tyr Ser Ile Arg
    1235                1240                1245
Ser Thr Leu Arg Met Glu Leu Met Gly Cys Asp Leu Asn Ser Cys
    1250                1255                1260
Ser Met Pro Leu Gly Met Gln Asn Lys Ala Ile Ser Asp Ser Gln
    1265                1270                1275
Ile Thr Ala Ser Ser His Leu Ser Asn Ile Phe Ala Thr Trp Ser
    1280                1285                1290
Pro Ser Gln Ala Arg Leu His Leu Gln Gly Arg Thr Asn Ala Trp
    1295                1300                1305
Arg Pro Arg Val Ser Ser Ala Glu Glu Trp Leu Gln Val Asp Leu
    1310                1315                1320
Gln Lys Thr Val Lys Val Thr Gly Ile Thr Thr Gln Gly Val Lys
    1325                1330                1335
Ser Leu Leu Ser Ser Met Tyr Val Lys Glu Phe Leu Val Ser Ser
    1340                1345                1350
Ser Gln Asp Gly Arg Arg Trp Thr Leu Phe Leu Gln Asp Gly His
    1355                1360                1365
Thr Lys Val Phe Gln Gly Asn Gln Asp Ser Ser Thr Pro Val Val
    1370                1375                1380
Asn Ala Leu Asp Pro Pro Leu Phe Thr Arg Tyr Leu Arg Ile His
    1385                1390                1395
Pro Thr Ser Trp Ala Gln His Ile Ala Leu Arg Leu Glu Val Leu
    1400                1405                1410
Gly Cys Glu Ala Gln Asp Leu Tyr
    1415                1420

<210> SEQ ID NO 2
<211> LENGTH: 1397
<212> TYPE: PRT
<213> ORGANISM: homo sapiens

<400> SEQUENCE: 2
```

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
                35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
            115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
    195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
    355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
```

```
            420                 425                 430
Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
            450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                    485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
            530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
            610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
            690                 695                 700

Leu Leu Lys Val Ser Ser Cys Asp Lys Glu Ile Thr Arg Thr Thr Leu
705                 710                 715                 720

Gln Ser Asp Gln Glu Glu Ile Asp Tyr Asp Asp Thr Ile Ser Val Glu
                725                 730                 735

Met Lys Lys Glu Asp Phe Asp Ile Tyr Asp Glu Asp Glu Asn Gln Ser
                740                 745                 750

Pro Arg Ser Phe Gln Lys Lys Thr Arg His Tyr Phe Ile Ala Ala Val
                755                 760                 765

Glu Arg Leu Trp Asp Tyr Gly Met Ser Ser Ser Pro His Val Leu Arg
            770                 775                 780

Asn Arg Ala Gln Ser Gly Ser Val Pro Gln Phe Lys Lys Val Val Phe
785                 790                 795                 800

Gln Glu Phe Thr Asp Gly Ser Phe Thr Gln Pro Leu Tyr Arg Gly Glu
                805                 810                 815

Leu Asn Glu His Leu Gly Leu Leu Gly Pro Tyr Ile Arg Ala Glu Val
                820                 825                 830

Glu Asp Asn Ile Met Val Thr Phe Arg Asn Gln Ala Ser Arg Pro Tyr
                835                 840                 845
```

-continued

Ser Phe Tyr Ser Ser Leu Ile Ser Tyr Glu Glu Asp Gln Arg Gln Gly
850                 855                 860

Ala Glu Pro Arg Lys Asn Phe Val Lys Pro Asn Glu Thr Lys Thr Tyr
865                 870                 875                 880

Phe Trp Lys Val Gln His His Met Ala Pro Thr Lys Asp Glu Phe Asp
            885                 890                 895

Cys Lys Ala Trp Ala Tyr Phe Ser Asp Val Asp Leu Glu Lys Asp Val
            900                 905                 910

His Ser Gly Leu Ile Gly Pro Leu Leu Val Cys His Thr Asn Thr Leu
        915                 920                 925

Asn Pro Ala His Gly Arg Gln Val Thr Val Gln Glu Phe Ala Leu Phe
    930                 935                 940

Phe Thr Ile Phe Asp Glu Thr Lys Ser Trp Tyr Phe Thr Glu Asn Met
945                 950                 955                 960

Glu Arg Asn Cys Arg Ala Pro Cys Asn Ile Gln Met Glu Asp Pro Thr
            965                 970                 975

Phe Lys Glu Asn Tyr Arg Phe His Ala Ile Asn Gly Tyr Ile Met Asp
            980                 985                 990

Thr Leu Pro Gly Leu Val Met Ala Gln Asp Gln Arg Ile Arg Trp Tyr
        995                 1000                1005

Leu Leu Ser Met Gly Ser Asn Glu Asn Ile His Ser Ile His Phe
        1010                1015                1020

Ser Gly His Val Phe Thr Val Arg Lys Lys Glu Glu Tyr Lys Met
        1025                1030                1035

Ala Leu Tyr Asn Leu Tyr Pro Gly Val Phe Glu Thr Val Glu Met
        1040                1045                1050

Leu Pro Ser Lys Ala Gly Ile Trp Arg Val Glu Cys Leu Ile Gly
        1055                1060                1065

Glu His Leu His Ala Gly Met Ser Thr Leu Phe Leu Val Tyr Ser
        1070                1075                1080

Asn Lys Cys Gln Thr Pro Leu Gly Met Ala Ser Gly His Ile Arg
        1085                1090                1095

Asp Phe Gln Ile Thr Ala Ser Gly Gln Tyr Gly Gln Trp Ala Pro
        1100                1105                1110

Lys Leu Ala Arg Leu His Tyr Ser Gly Ser Ile Asn Ala Trp Ser
        1115                1120                1125

Thr Lys Glu Pro Phe Ser Trp Ile Lys Val Asp Leu Leu Ala Pro
        1130                1135                1140

Met Ile Ile His Gly Ile Lys Thr Gln Gly Ala Arg Gln Lys Phe
        1145                1150                1155

Ser Ser Leu Tyr Ile Ser Gln Phe Ile Ile Met Tyr Ser Leu Asp
        1160                1165                1170

Gly Lys Lys Trp Gln Thr Tyr Arg Gly Asn Ser Thr Gly Thr Leu
        1175                1180                1185

Met Val Phe Phe Gly Asn Val Asp Ser Ser Gly Ile Lys His Asn
        1190                1195                1200

Ile Phe Asn Pro Pro Ile Ile Ala Arg Tyr Ile Arg Leu His Pro
        1205                1210                1215

Thr His Tyr Ser Ile Arg Ser Thr Leu Arg Met Glu Leu Met Gly
        1220                1225                1230

Cys Asp Leu Asn Ser Cys Ser Met Pro Leu Gly Met Glu Ser Lys
        1235                1240                1245

Ala Ile Ser Asp Ala Gln Ile Thr Ala Ser Ser Tyr Phe Thr Asn
    1250                1255                1260

Met Phe Ala Thr Trp Ser Pro Ser Lys Ala Arg Leu His Leu Gln
1265                1270                1275

Gly Arg Ser Asn Ala Trp Arg Pro Gln Val Asn Asn Pro Lys Glu
    1280                1285                1290

Trp Leu Gln Val Asp Phe Gln Lys Thr Met Lys Val Thr Gly Val
    1295                1300                1305

Thr Thr Gln Gly Val Lys Ser Leu Leu Thr Ser Met Tyr Val Lys
    1310                1315                1320

Glu Phe Leu Ile Ser Ser Ser Gln Asp Gly His Gln Trp Thr Leu
    1325                1330                1335

Phe Phe Gln Asn Gly Lys Val Lys Val Phe Gln Gly Asn Gln Asp
    1340                1345                1350

Ser Phe Thr Pro Val Val Asn Ser Leu Asp Pro Pro Leu Leu Thr
    1355                1360                1365

Arg Tyr Leu Arg Ile His Pro Gln Ser Trp Val His Gln Ile Ala
    1370                1375                1380

Leu Arg Met Glu Val Leu Gly Cys Glu Ala Gln Asp Leu Tyr
    1385                1390                1395

<210> SEQ ID NO 3
<211> LENGTH: 1397
<212> TYPE: PRT
<213> ORGANISM: Canis familiaris

<400> SEQUENCE: 3

Ala Thr Arg Lys Tyr Tyr Leu Gly Ala Val Glu Leu Ser Trp Asp Tyr
1               5                   10                  15

Met Gln Ser Asp Leu Leu Ser Ala Leu His Ala Asp Thr Ser Phe Ser
            20                  25                  30

Ser Arg Val Pro Gly Ser Leu Pro Leu Thr Thr Ser Val Thr Tyr Arg
        35                  40                  45

Lys Thr Val Phe Val Glu Phe Thr Asp Asp Leu Phe Asn Ile Ala Lys
    50                  55                  60

Pro Arg Pro Pro Trp Met Gly Leu Leu Gly Pro Thr Ile Gln Ala Glu
65                  70                  75                  80

Val Tyr Asp Thr Val Val Ile Val Leu Lys Asn Met Ala Ser His Pro
                85                  90                  95

Val Ser Leu His Ala Val Gly Val Ser Tyr Trp Lys Ala Ser Glu Gly
            100                 105                 110

Ala Glu Tyr Glu Asp Gln Thr Ser Gln Lys Glu Lys Glu Asp Asp Asn
        115                 120                 125

Val Ile Pro Gly Glu Ser His Thr Tyr Val Trp Gln Val Leu Lys Glu
    130                 135                 140

Asn Gly Pro Met Ala Ser Asp Pro Pro Cys Leu Thr Tyr Ser Tyr Phe
145                 150                 155                 160

Ser His Val Asp Leu Val Lys Asp Leu Asn Ser Gly Leu Ile Gly Ala
                165                 170                 175

Leu Leu Val Cys Lys Glu Gly Ser Leu Ala Lys Glu Arg Thr Gln Thr
            180                 185                 190

Leu Gln Glu Phe Val Leu Leu Phe Ala Val Phe Asp Glu Gly Lys Ser
        195                 200                 205

Trp His Ser Glu Thr Asn Ala Ser Leu Thr Gln Ala Glu Ala Gln His
    210                 215                 220

-continued

```
Glu Leu His Thr Ile Asn Gly Tyr Val Asn Arg Ser Leu Pro Gly Leu
225                 230                 235                 240

Thr Val Cys His Lys Arg Ser Val Tyr Trp His Val Ile Gly Met Gly
                245                 250                 255

Thr Thr Pro Glu Val His Ser Ile Phe Leu Glu Gly His Thr Phe Leu
            260                 265                 270

Val Arg Asn His Arg Gln Ala Ser Leu Glu Ile Ser Pro Ile Thr Phe
        275                 280                 285

Leu Thr Ala Gln Thr Phe Leu Met Asp Leu Gly Gln Phe Leu Leu Phe
290                 295                 300

Cys His Ile Pro Ser His Gln His Asp Gly Met Glu Ala Tyr Val Lys
305                 310                 315                 320

Val Asp Ser Cys Pro Glu Glu Pro Gln Leu Arg Met Lys Asn Asn Glu
                325                 330                 335

Asp Lys Asp Tyr Asp Asp Gly Leu Tyr Asp Ser Asp Met Asp Val Val
            340                 345                 350

Ser Phe Asp Asp Asp Ser Ser Pro Phe Ile Gln Ile Arg Ser Val
        355                 360                 365

Ala Lys Lys His Pro Lys Thr Trp Val His Tyr Ile Ala Ala Glu Glu
370                 375                 380

Glu Asp Trp Asp Tyr Ala Pro Ser Gly Pro Thr Pro Asn Asp Arg Ser
385                 390                 395                 400

His Lys Asn Leu Tyr Leu Asn Asn Gly Pro Gln Arg Ile Gly Lys Lys
                405                 410                 415

Tyr Lys Lys Val Arg Phe Val Ala Tyr Thr Asp Glu Thr Phe Lys Thr
            420                 425                 430

Arg Glu Ala Ile Gln Tyr Glu Ser Gly Ile Leu Gly Pro Leu Leu Tyr
        435                 440                 445

Gly Glu Val Gly Asp Thr Leu Leu Ile Ile Phe Lys Asn Gln Ala Ser
450                 455                 460

Arg Pro Tyr Asn Ile Tyr Pro His Gly Ile Asn Tyr Val Thr Pro Leu
465                 470                 475                 480

His Thr Gly Arg Leu Pro Lys Gly Val Lys His Leu Lys Asp Met Pro
                485                 490                 495

Ile Leu Pro Gly Glu Ile Phe Lys Tyr Lys Trp Thr Val Thr Val Glu
            500                 505                 510

Asp Gly Pro Thr Lys Ser Asp Pro Arg Cys Leu Thr Arg Tyr Tyr Ser
        515                 520                 525

Ser Phe Ile Asn Leu Glu Arg Asp Leu Ala Ser Gly Leu Ile Gly Pro
530                 535                 540

Leu Leu Ile Cys Tyr Lys Glu Ser Val Asp Gln Arg Gly Asn Gln Met
545                 550                 555                 560

Met Ser Asp Lys Arg Asn Val Ile Leu Phe Ser Val Phe Asp Glu Asn
                565                 570                 575

Arg Ser Trp Tyr Leu Thr Glu Asn Met Gln Arg Phe Leu Pro Asn Ala
            580                 585                 590

Asp Val Val Gln Pro His Asp Pro Glu Phe Gln Leu Ser Asn Ile Met
        595                 600                 605

His Ser Ile Asn Gly Tyr Val Phe Asp Asn Leu Gln Leu Ser Val Cys
610                 615                 620

Leu His Glu Val Ala Tyr Trp Tyr Ile Leu Ser Val Gly Ala Gln Thr
625                 630                 635                 640
```

-continued

```
Asp Phe Leu Ser Val Phe Ser Gly Tyr Thr Phe Lys His Lys Met
            645                 650                 655

Val Tyr Glu Asp Thr Leu Thr Leu Phe Pro Phe Ser Gly Glu Thr Val
        660                 665                 670

Phe Met Ser Met Glu Asn Pro Gly Leu Trp Val Leu Gly Cys His Asn
    675                 680                 685

Ser Asp Phe Arg Asn Phe Val Ile Ile Ile Asn Arg Gly Met Thr Ala
690                 695                 700

Leu Leu Lys Val Ser Ser Cys Asn Arg Glu Ile Thr Val Thr Thr Leu
705                 710                 715                 720

Gln Pro Glu Glu Asp Lys Phe Glu Tyr Asp Asp Thr Phe Ser Ile Glu
                725                 730                 735

Met Lys Arg Glu Asp Phe Asp Ile Tyr Gly Asp Tyr Glu Asn Gln Gly
            740                 745                 750

Leu Arg Ser Phe Gln Lys Lys Thr Arg His Tyr Phe Ile Ala Ala Val
        755                 760                 765

Glu Arg Leu Trp Asp Tyr Gly Met Ser Arg Ser Pro His Ile Leu Arg
    770                 775                 780

Asn Arg Ala Gln Ser Gly Asp Val Gln Gln Phe Lys Lys Val Val Phe
785                 790                 795                 800

Gln Glu Phe Thr Asp Gly Ser Phe Thr Gln Pro Leu Tyr Arg Gly Glu
                805                 810                 815

Leu Asn Glu His Leu Gly Leu Leu Gly Pro Tyr Ile Arg Ala Glu Val
            820                 825                 830

Glu Asp Asn Ile Val Val Thr Phe Lys Asn Gln Ala Ser Arg Pro Tyr
        835                 840                 845

Ser Phe Tyr Ser Ser Leu Ile Ser Tyr Asp Glu Asp Glu Gly Gln Gly
    850                 855                 860

Ala Glu Pro Arg Arg Lys Phe Val Asn Pro Asn Glu Thr Lys Ile Tyr
865                 870                 875                 880

Phe Trp Lys Val Gln His His Met Ala Pro Thr Lys Asp Glu Phe Asp
                885                 890                 895

Cys Lys Ala Trp Ala Tyr Phe Ser Asp Val Asp Leu Glu Lys Asp Val
            900                 905                 910

His Ser Gly Leu Ile Gly Pro Leu Leu Ile Cys Arg Ser Asn Thr Leu
        915                 920                 925

Asn Pro Ala His Gly Arg Gln Val Thr Val Gln Glu Phe Ala Leu Val
    930                 935                 940

Phe Thr Ile Phe Asp Glu Thr Lys Ser Trp Tyr Phe Thr Glu Asn Leu
945                 950                 955                 960

Glu Arg Asn Cys Arg Ala Pro Cys Asn Val Gln Lys Glu Asp Pro Thr
                965                 970                 975

Leu Lys Glu Asn Phe Arg Phe His Ala Ile Asn Gly Tyr Val Lys Asp
            980                 985                 990

Thr Leu Pro Gly Leu Val Met Ala  Gln Asp Gln Lys Val  Arg Trp Tyr
        995                 1000                1005

Leu Leu  Ser Met Gly Ser Asn  Glu Asn Ile His Ser  Ile His Phe
    1010                1015                1020

Ser Gly  His Val Phe Thr Val  Arg Lys Lys Glu Glu  Tyr Lys Met
    1025                1030                1035

Ala Val  Tyr Asn Leu Tyr Pro  Gly Val Phe Glu Thr  Val Glu Met
    1040                1045                1050

Leu Pro  Ser Gln Val Gly Ile  Trp Arg Ile Glu Cys  Leu Ile Gly
```

```
                    1055                1060                1065

Glu His Leu Gln Ala Gly Met Ser Thr Leu Phe Leu Val Tyr Ser
         1070                1075                1080

Lys Lys Cys Gln Thr Pro Leu Gly Met Ala Ser Gly His Ile Arg
    1085                1090                1095

Asp Phe Gln Ile Thr Ala Ser Gly Gln Tyr Gly Gln Trp Ala Pro
    1100                1105                1110

Lys Leu Ala Arg Leu His Tyr Ser Gly Ser Ile Asn Ala Trp Ser
    1115                1120                1125

Thr Lys Asp Pro Phe Ser Trp Ile Lys Val Asp Leu Leu Ala Pro
    1130                1135                1140

Met Ile Ile His Gly Ile Met Thr Gln Gly Ala Arg Gln Lys Phe
    1145                1150                1155

Ser Ser Leu Tyr Val Ser Gln Phe Ile Ile Met Tyr Ser Leu Asp
    1160                1165                1170

Gly Asn Lys Trp His Ser Tyr Arg Gly Asn Ser Thr Gly Thr Leu
    1175                1180                1185

Met Val Phe Phe Gly Asn Val Asp Ser Ser Gly Ile Lys His Asn
    1190                1195                1200

Ile Phe Asn Pro Pro Ile Ile Ala Gln Tyr Ile Arg Leu His Pro
    1205                1210                1215

Thr His Tyr Ser Ile Arg Ser Thr Leu Arg Met Glu Leu Leu Gly
    1220                1225                1230

Cys Asp Phe Asn Ser Cys Ser Met Pro Leu Gly Met Glu Ser Lys
    1235                1240                1245

Ala Ile Ser Asp Ala Gln Ile Thr Ala Ser Ser Tyr Leu Ser Ser
    1250                1255                1260

Met Leu Ala Thr Trp Ser Pro Ser Gln Ala Arg Leu His Leu Gln
    1265                1270                1275

Gly Arg Thr Asn Ala Trp Arg Pro Gln Ala Asn Asn Pro Lys Glu
    1280                1285                1290

Trp Leu Gln Val Asp Phe Arg Lys Thr Met Lys Val Thr Gly Ile
    1295                1300                1305

Thr Thr Gln Gly Val Lys Ser Leu Leu Ile Ser Met Tyr Val Lys
    1310                1315                1320

Glu Phe Leu Ile Ser Ser Ser Gln Asp Gly His Asn Trp Thr Leu
    1325                1330                1335

Phe Leu Gln Asn Gly Lys Val Lys Val Phe Gln Gly Asn Arg Asp
    1340                1345                1350

Ser Ser Thr Pro Val Arg Asn Arg Leu Glu Pro Pro Leu Val Ala
    1355                1360                1365

Arg Tyr Val Arg Leu His Pro Gln Ser Trp Ala His His Ile Ala
    1370                1375                1380

Leu Arg Leu Glu Val Leu Gly Cys Asp Thr Gln Gln Pro Ala
    1385                1390                1395

<210> SEQ ID NO 4
<211> LENGTH: 24
<212> TYPE: PRT
<213> ORGANISM: sus scrofa

<400> SEQUENCE: 4

Ser Phe Ala Gln Asn Ser Arg Pro Pro Ser Ala Ser Ala Pro Lys Pro
1               5                   10                  15
```

```
Pro Val Leu Arg Arg His Gln Arg
            20

<210> SEQ ID NO 5
<211> LENGTH: 24
<212> TYPE: PRT
<213> ORGANISM: homo sapiens

<400> SEQUENCE: 5

Ser Phe Ser Gln Asn Ser Arg His Pro Ser Thr Arg Ser Gln Asn Pro
1               5                   10                  15

Pro Val Leu Lys Arg His Gln Arg
            20

<210> SEQ ID NO 6
<211> LENGTH: 24
<212> TYPE: PRT
<213> ORGANISM: Canis familiaris

<400> SEQUENCE: 6

Ser Phe Ser Gln Asn Ser Arg His Pro Ser Thr Lys Ser Gln Asn Pro
1               5                   10                  15

Pro Val Ser Lys His His Gln Arg
            20

<210> SEQ ID NO 7
<211> LENGTH: 2114
<212> TYPE: PRT
<213> ORGANISM: Sus scrofa

<400> SEQUENCE: 7

Ala Ile Arg Arg Tyr Tyr Leu Gly Ala Val Glu Leu Ser Trp Asp Tyr
1               5                   10                  15

Arg Gln Ser Glu Leu Leu Arg Glu Leu His Val Asp Thr Arg Phe Pro
                20                  25                  30

Ala Thr Ala Pro Gly Ala Leu Pro Leu Gly Pro Ser Val Leu Tyr Lys
            35                  40                  45

Lys Thr Val Phe Val Glu Phe Thr Asp Gln Leu Phe Ser Val Ala Arg
        50                  55                  60

Pro Arg Pro Pro Trp Met Gly Leu Leu Gly Pro Thr Ile Gln Ala Glu
65                  70                  75                  80

Val Tyr Asp Thr Val Val Val Thr Leu Lys Asn Met Ala Ser His Pro
                85                  90                  95

Val Ser Leu His Ala Val Gly Val Ser Phe Trp Lys Ser Ser Glu Gly
                100                 105                 110

Ala Glu Tyr Glu Asp His Thr Ser Gln Arg Glu Lys Glu Asp Asp Lys
            115                 120                 125

Val Leu Pro Gly Lys Ser Gln Thr Tyr Val Trp Gln Val Leu Lys Glu
        130                 135                 140

Asn Gly Pro Thr Ala Ser Asp Pro Pro Cys Leu Thr Tyr Ser Tyr Leu
145                 150                 155                 160

Ser His Val Asp Leu Val Lys Asp Leu Asn Ser Gly Leu Ile Gly Ala
                165                 170                 175

Leu Leu Val Cys Arg Glu Gly Ser Leu Thr Arg Glu Arg Thr Gln Asn
                180                 185                 190

Leu His Glu Phe Val Leu Leu Phe Ala Val Phe Asp Glu Gly Lys Ser
            195                 200                 205

Trp His Ser Ala Arg Asn Asp Ser Trp Thr Arg Ala Met Asp Pro Ala
```

```
            210                 215                 220
Pro Ala Arg Ala Gln Pro Ala Met His Thr Val Asn Gly Tyr Val Asn
225                 230                 235                 240

Arg Ser Leu Pro Gly Leu Ile Gly Cys His Lys Ser Val Tyr Trp
                245                 250                 255

His Val Ile Gly Met Gly Thr Ser Pro Glu Val His Ser Ile Phe Leu
                260                 265                 270

Glu Gly His Thr Phe Leu Val Arg His Arg Gln Ala Ser Leu Glu
            275                 280                 285

Ile Ser Pro Leu Thr Phe Leu Thr Ala Gln Thr Phe Leu Met Asp Leu
290                 295                 300

Gly Gln Phe Leu Leu Phe Cys His Ile Ser Ser His His Gly Gly
305                 310                 315                 320

Met Glu Ala His Val Arg Val Glu Ser Cys Ala Glu Pro Gln Leu
                325                 330                 335

Arg Arg Lys Ala Asp Glu Glu Asp Tyr Asp Asp Asn Leu Tyr Asp
            340                 345                 350

Ser Asp Met Asp Val Val Arg Leu Asp Gly Asp Val Ser Pro Phe
                355                 360                 365

Ile Gln Ile Arg Ser Val Ala Lys Lys His Pro Lys Thr Trp Val His
370                 375                 380

Tyr Ile Ser Ala Glu Glu Asp Trp Asp Tyr Ala Pro Ala Val Pro
385                 390                 395                 400

Ser Pro Ser Asp Arg Ser Tyr Lys Ser Leu Tyr Leu Asn Ser Gly Pro
                405                 410                 415

Gln Arg Ile Gly Arg Lys Tyr Lys Lys Ala Arg Phe Val Ala Tyr Thr
                420                 425                 430

Asp Val Thr Phe Lys Thr Arg Lys Ala Ile Pro Tyr Glu Ser Gly Ile
            435                 440                 445

Leu Gly Pro Leu Leu Tyr Gly Glu Val Gly Asp Thr Leu Leu Ile Ile
            450                 455                 460

Phe Lys Asn Lys Ala Ser Arg Pro Tyr Asn Ile Tyr Pro His Gly Ile
465                 470                 475                 480

Thr Asp Val Ser Ala Leu His Pro Gly Arg Leu Leu Lys Gly Trp Lys
                485                 490                 495

His Leu Lys Asp Met Pro Ile Leu Pro Gly Glu Thr Phe Lys Tyr Lys
            500                 505                 510

Trp Thr Val Thr Val Glu Asp Gly Pro Thr Lys Ser Asp Pro Arg Cys
            515                 520                 525

Leu Thr Arg Tyr Tyr Ser Ser Ser Ile Asn Leu Glu Lys Asp Leu Ala
530                 535                 540

Ser Gly Leu Ile Gly Pro Leu Leu Ile Cys Tyr Lys Glu Ser Val Asp
545                 550                 555                 560

Gln Arg Gly Asn Gln Met Met Ser Asp Lys Arg Asn Val Ile Leu Phe
                565                 570                 575

Ser Val Phe Asp Glu Asn Gln Ser Trp Tyr Leu Ala Glu Asn Ile Gln
                580                 585                 590

Arg Phe Leu Pro Asn Pro Asp Gly Leu Gln Pro Gln Asp Pro Glu Phe
                595                 600                 605

Gln Ala Ser Asn Ile Met His Ser Ile Asn Gly Tyr Val Phe Asp Ser
            610                 615                 620

Leu Gln Leu Ser Val Cys Leu His Glu Val Ala Tyr Trp Tyr Ile Leu
625                 630                 635                 640
```

-continued

Ser Val Gly Ala Gln Thr Asp Phe Leu Ser Val Phe Gly Tyr
              645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
            675                 680                 685

Val Leu Gly Cys His Asn Ser Asp Leu Arg Asn Arg Gly Met Thr Ala
        690                 695                 700

Leu Leu Lys Val Tyr Ser Cys Asp Arg Asp Ile Gly Asp Tyr Tyr Asp
705                 710                 715                 720

Asn Thr Tyr Glu Asp Ile Pro Gly Phe Leu Leu Ser Gly Lys Asn Val
            725                 730                 735

Ile Glu Pro Arg Ser Phe Ala Gln Asn Ser Arg Pro Pro Ser Ala Ser
            740                 745                 750

Gln Lys Gln Phe Gln Thr Ile Thr Ser Pro Glu Asp Val Glu Leu
            755                 760                 765

Asp Pro Gln Ser Gly Glu Arg Thr Gln Ala Leu Glu Glu Leu Ser Val
        770                 775                 780

Pro Ser Gly Asp Gly Ser Met Leu Leu Gly Gln Asn Pro Ala Pro His
785                 790                 795                 800

Gly Ser Ser Ser Asp Leu Gln Glu Ala Arg Asn Glu Ala Asp Asp
            805                 810                 815

Tyr Leu Pro Gly Ala Arg Glu Arg Asn Thr Ala Pro Ser Ala Ala Ala
            820                 825                 830

Arg Leu Arg Pro Glu Leu His His Ser Ala Glu Arg Val Leu Thr Pro
            835                 840                 845

Glu Pro Glu Lys Glu Leu Lys Lys Leu Asp Ser Lys Met Ser Ser Ser
        850                 855                 860

Ser Asp Leu Leu Lys Thr Ser Pro Thr Ile Pro Ser Asp Thr Leu Ser
865                 870                 875                 880

Ala Glu Thr Glu Arg Thr His Ser Leu Gly Pro Pro His Pro Gln Val
            885                 890                 895

Asn Phe Arg Ser Gln Leu Gly Ala Ile Val Leu Gly Lys Asn Ser Ser
            900                 905                 910

His Phe Ile Gly Ala Gly Val Pro Leu Gly Ser Thr Glu Glu Asp His
            915                 920                 925

Glu Ser Ser Leu Gly Glu Asn Val Ser Pro Val Glu Ser Asp Gly Ile
        930                 935                 940

Phe Glu Lys Glu Arg Ala His Gly Pro Ala Ser Leu Thr Lys Asp Asp
945                 950                 955                 960

Val Leu Phe Lys Val Asn Ile Ser Leu Val Lys Thr Asn Lys Ala Arg
            965                 970                 975

Val Tyr Leu Lys Thr Asn Arg Lys Ile His Ile Asp Asp Ala Ala Leu
            980                 985                 990

Leu Thr Glu Asn Arg Ala Ser Ala Thr Phe Met Asp Lys Asn Thr Thr
            995                 1000                1005

Ala Ser Gly Leu Asn His Val Ser Asn Trp Ile Lys Gly Pro Leu
            1010                1015                1020

Gly Lys Asn Pro Leu Ser Ser Glu Arg Gly Pro Ser Pro Glu Leu
            1025                1030                1035

Leu Thr Ser Ser Gly Ser Gly Lys Ser Val Lys Gly Gln Ser Ser
            1040                1045                1050

Gly Gln Gly Arg Ile Arg Val Ala Val Glu Glu Glu Leu Ser
1055               1060              1065

Lys Gly Lys Glu Met Met Leu Pro Asn Ser Glu Leu Thr Phe Leu
1070               1075              1080

Thr Asn Ser Ala Asp Val Gln Gly Asn Asp Thr His Ser Gln Gly
1085               1090              1095

Lys Lys Ser Arg Glu Glu Met Glu Arg Arg Lys Leu Val Gln
1100               1105              1110

Glu Lys Val Asp Leu Pro Gln Val Tyr Thr Ala Thr Gly Thr Lys
1115               1120              1125

Asn Phe Leu Arg Asn Ile Phe His Gln Ser Thr Glu Pro Ser Val
1130               1135              1140

Glu Gly Phe Asp Gly Gly Ser His Ala Pro Val Pro Gln Asp Ser
1145               1150              1155

Arg Ser Leu Asn Asp Ser Ala Glu Arg Ala Glu Thr His Ile Ala
1160               1165              1170

His Phe Ser Ala Ile Arg Glu Glu Ala Pro Leu Glu Ala Pro Gly
1175               1180              1185

Asn Arg Thr Gly Pro Gly Pro Arg Ser Ala Val Pro Arg Arg Val
1190               1195              1200

Lys Gln Ser Leu Lys Gln Ile Arg Leu Pro Leu Glu Glu Ile Lys
1205               1210              1215

Pro Glu Arg Gly Val Val Leu Asn Ala Thr Ser Thr Arg Trp Ser
1220               1225              1230

Glu Ser Ser Pro Ile Leu Gln Gly Ala Lys Arg Asn Asn Leu Ser
1235               1240              1245

Leu Pro Phe Leu Thr Leu Glu Met Ala Gly Gly Gln Gly Lys Ile
1250               1255              1260

Ser Ala Leu Gly Lys Ser Ala Ala Gly Pro Leu Ala Ser Gly Lys
1265               1270              1275

Leu Glu Lys Ala Val Leu Ser Ser Ala Gly Leu Ser Glu Ala Ser
1280               1285              1290

Gly Lys Ala Glu Phe Leu Pro Lys Val Arg Val His Arg Glu Asp
1295               1300              1305

Leu Leu Pro Gln Lys Thr Ser Asn Val Ser Cys Ala His Gly Asp
1310               1315              1320

Leu Gly Gln Glu Ile Phe Leu Gln Lys Thr Arg Gly Pro Val Asn
1325               1330              1335

Leu Asn Lys Val Asn Arg Pro Gly Arg Thr Pro Ser Lys Leu Leu
1340               1345              1350

Gly Pro Pro Met Pro Lys Glu Trp Glu Ser Leu Glu Lys Ser Pro
1355               1360              1365

Lys Ser Thr Ala Leu Arg Thr Lys Asp Ile Ile Ser Leu Pro Leu
1370               1375              1380

Asp Arg His Glu Ser Asn His Ser Ile Ala Ala Lys Asn Glu Gly
1385               1390              1395

Gln Ala Glu Thr Gln Arg Glu Ala Ala Trp Thr Lys Gln Gly Gly
1400               1405              1410

Pro Gly Arg Leu Cys Ala Pro Lys Pro Pro Val Leu Arg Arg His
1415               1420              1425

Gln Arg Asp Ile Ser Leu Pro Thr Phe Gln Pro Glu Glu Asp Lys
1430               1435              1440

Met Asp Tyr Asp Asp Ile Phe Ser Thr Glu Thr Lys Gly Glu Asp

```
            1445                1450                1455

Phe Asp Ile Tyr Gly Glu Asp Glu Asn Gln Asp Pro Arg Ser Phe
        1460                1465                1470

Gln Lys Arg Thr Arg His Tyr Phe Ile Ala Ala Val Glu Gln Leu
    1475                1480                1485

Trp Asp Tyr Gly Met Ser Glu Ser Pro Arg Ala Leu Arg Asn Arg
    1490                1495                1500

Ala Gln Asn Gly Glu Val Pro Arg Phe Lys Lys Val Val Phe Arg
    1505                1510                1515

Glu Phe Ala Asp Gly Ser Phe Thr Gln Pro Ser Tyr Arg Gly Glu
    1520                1525                1530

Leu Asn Lys His Leu Gly Leu Leu Gly Pro Tyr Ile Arg Ala Glu
    1535                1540                1545

Val Glu Asp Asn Ile Met Val Thr Phe Lys Asn Gln Ala Ser Arg
    1550                1555                1560

Pro Tyr Ser Phe Tyr Ser Ser Leu Ile Ser Tyr Pro Asp Asp Gln
    1565                1570                1575

Glu Gln Gly Ala Glu Pro Arg His Asn Phe Val Gln Pro Asn Glu
    1580                1585                1590

Thr Arg Thr Tyr Phe Trp Lys Val Gln His His Met Ala Pro Thr
    1595                1600                1605

Glu Asp Glu Phe Asp Cys Lys Ala Trp Ala Tyr Phe Ser Asp Val
    1610                1615                1620

Asp Leu Glu Lys Asp Val His Ser Gly Leu Ile Gly Pro Leu Leu
    1625                1630                1635

Ile Cys Arg Ala Asn Thr Leu Asn Ala Ala His Gly Arg Gln Val
    1640                1645                1650

Thr Val Gln Glu Phe Ala Leu Phe Phe Thr Ile Phe Asp Glu Thr
    1655                1660                1665

Lys Ser Trp Tyr Phe Thr Glu Asn Val Glu Arg Asn Cys Arg Ala
    1670                1675                1680

Pro Cys His Leu Gln Met Glu Asp Pro Thr Leu Lys Glu Asn Tyr
    1685                1690                1695

Arg Phe His Ala Ile Asn Gly Tyr Val Met Asp Thr Leu Pro Gly
    1700                1705                1710

Leu Val Met Ala Gln Asn Gln Arg Ile Arg Trp Tyr Leu Leu Ser
    1715                1720                1725

Met Gly Ser Asn Glu Asn Ile His Ser Ile His Phe Ser Gly His
    1730                1735                1740

Val Phe Ser Val Arg Lys Lys Glu Glu Tyr Lys Met Ala Val Tyr
    1745                1750                1755

Asn Leu Tyr Pro Gly Val Phe Glu Thr Val Glu Met Leu Pro Ser
    1760                1765                1770

Lys Val Gly Ile Trp Arg Ile Glu Cys Leu Ile Gly Glu His Leu
    1775                1780                1785

Gln Ala Gly Met Ser Thr Thr Phe Leu Val Tyr Ser Lys Glu Cys
    1790                1795                1800

Gln Ala Pro Leu Gly Met Ala Ser Gly Arg Ile Arg Asp Phe Gln
    1805                1810                1815

Ile Thr Ala Ser Gly Gln Tyr Gly Gln Trp Ala Pro Lys Leu Ala
    1820                1825                1830

Arg Leu His Tyr Ser Gly Ser Ile Asn Ala Trp Ser Thr Lys Asp
    1835                1840                1845
```

-continued

Pro His Ser Trp Ile Lys Val Asp Leu Leu Ala Pro Met Ile Ile
    1850                1855                1860

His Gly Ile Met Thr Gln Gly Ala Arg Gln Lys Phe Ser Ser Leu
    1865                1870                1875

Tyr Ile Ser Gln Phe Ile Ile Met Tyr Ser Leu Asp Gly Arg Asn
    1880                1885                1890

Trp Gln Ser Tyr Arg Gly Asn Ser Thr Gly Thr Leu Met Val Phe
    1895                1900                1905

Phe Gly Asn Val Asp Ala Ser Gly Ile Lys His Asn Ile Phe Asn
    1910                1915                1920

Pro Pro Ile Val Ala Arg Tyr Ile Arg Leu His Pro Thr His Tyr
    1925                1930                1935

Ser Ile Arg Ser Thr Leu Arg Met Glu Leu Met Gly Cys Asp Leu
    1940                1945                1950

Asn Ser Cys Ser Met Pro Leu Gly Met Gln Asn Lys Ala Ile Ser
    1955                1960                1965

Asp Ser Gln Ile Thr Ala Ser Ser His Leu Ser Asn Ile Phe Ala
    1970                1975                1980

Thr Trp Ser Pro Ser Gln Ala Arg Leu His Leu Gln Gly Arg Thr
    1985                1990                1995

Asn Ala Trp Arg Pro Arg Val Ser Ser Ala Glu Glu Trp Leu Gln
    2000                2005                2010

Val Asp Leu Gln Lys Thr Val Lys Val Thr Gly Ile Thr Thr Gln
    2015                2020                2025

Gly Val Lys Ser Leu Leu Ser Ser Met Tyr Val Lys Glu Phe Leu
    2030                2035                2040

Val Ser Ser Ser Gln Asp Gly Arg Arg Trp Thr Leu Phe Leu Gln
    2045                2050                2055

Asp Gly His Thr Lys Val Phe Gln Gly Asn Gln Asp Ser Ser Thr
    2060                2065                2070

Pro Val Val Asn Ala Leu Asp Pro Pro Leu Phe Thr Arg Tyr Leu
    2075                2080                2085

Arg Ile His Pro Thr Ser Trp Ala Gln His Ile Ala Leu Arg Leu
    2090                2095                2100

Glu Val Leu Gly Cys Glu Ala Gln Asp Leu Tyr
    2105                2110

<210> SEQ ID NO 8
<211> LENGTH: 2332
<212> TYPE: PRT
<213> ORGANISM: homo sapiens

<400> SEQUENCE: 8

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
                20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val

```
                    85                  90                  95
Ser Leu His Ala Val Gly Val Ser Tyr Trp Lys Ala Ser Glu Gly Ala
                100                 105                 110

Glu Tyr Asp Asp Gln Thr Ser Gln Arg Glu Lys Glu Asp Asp Lys Val
                115                 120                 125

Phe Pro Gly Gly Ser His Thr Tyr Val Trp Gln Val Leu Lys Glu Asn
130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
                180                 185                 190

His Lys Phe Ile Leu Leu Phe Ala Val Phe Asp Glu Gly Lys Ser Trp
                195                 200                 205

His Ser Glu Thr Lys Asn Ser Leu Met Gln Asp Arg Asp Ala Ala Ser
                210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
                260                 265                 270

Gly His Thr Phe Leu Val Arg Asn His Arg Gln Ala Ser Leu Glu Ile
                275                 280                 285

Ser Pro Ile Thr Phe Leu Thr Ala Gln Thr Leu Leu Met Asp Leu Gly
                290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
                340                 345                 350

Ser Glu Met Asp Val Val Arg Phe Asp Asp Asp Asn Ser Pro Ser Phe
                355                 360                 365

Ile Gln Ile Arg Ser Val Ala Lys Lys His Pro Lys Thr Trp Val His
370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
                435                 440                 445

Leu Gly Pro Leu Leu Tyr Gly Glu Val Gly Asp Thr Leu Leu Ile Ile
                450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510
```

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
        530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys
        755                 760                 765

Thr Asp Pro Trp Phe Ala His Arg Thr Pro Met Pro Lys Ile Gln Asn
    770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
            820                 825                 830

Glu Met Thr His Phe Arg Pro Gln Leu His His Ser Gly Asp Met Val
        835                 840                 845

Phe Thr Pro Glu Ser Gly Leu Gln Leu Arg Leu Asn Glu Lys Leu Gly
    850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
        915                 920                 925

```
Leu Thr Glu Ser Gly Gly Pro Leu Ser Leu Ser Glu Asn Asn Asp
    930             935             940

Ser Lys Leu Leu Glu Ser Gly Leu Met Asn Ser Gln Glu Ser Ser Trp
945             950              955             960

Gly Lys Asn Val Ser Ser Thr Glu Ser Gly Arg Leu Phe Lys Gly Lys
                965             970             975

Arg Ala His Gly Pro Ala Leu Leu Thr Lys Asp Asn Ala Leu Phe Lys
            980             985             990

Val Ser Ile Ser Leu Leu Lys Thr Asn Lys Thr Ser Asn Asn Ser Ala
        995             1000            1005

Thr Asn Arg Lys Thr His Ile Asp Gly Pro Ser Leu Leu Ile Glu
    1010            1015            1020

Asn Ser Pro Ser Val Trp Gln Asn Ile Leu Glu Ser Asp Thr Glu
    1025            1030            1035

Phe Lys Lys Val Thr Pro Leu Ile His Asp Arg Met Leu Met Asp
    1040            1045            1050

Lys Asn Ala Thr Ala Leu Arg Leu Asn His Met Ser Asn Lys Thr
    1055            1060            1065

Thr Ser Ser Lys Asn Met Glu Met Val Gln Gln Lys Lys Glu Gly
    1070            1075            1080

Pro Ile Pro Pro Asp Ala Gln Asn Pro Asp Met Ser Phe Phe Lys
    1085            1090            1095

Met Leu Phe Leu Pro Glu Ser Ala Arg Trp Ile Gln Arg Thr His
    1100            1105            1110

Gly Lys Asn Ser Leu Asn Ser Gly Gln Gly Pro Ser Pro Lys Gln
    1115            1120            1125

Leu Val Ser Leu Gly Pro Glu Lys Ser Val Glu Gly Gln Asn Phe
    1130            1135            1140

Leu Ser Glu Lys Asn Lys Val Val Val Gly Lys Gly Glu Phe Thr
    1145            1150            1155

Lys Asp Val Gly Leu Lys Glu Met Val Phe Pro Ser Ser Arg Asn
    1160            1165            1170

Leu Phe Leu Thr Asn Leu Asp Asn Leu His Glu Asn Asn Thr His
    1175            1180            1185

Asn Gln Glu Lys Lys Ile Gln Glu Glu Ile Glu Lys Lys Glu Thr
    1190            1195            1200

Leu Ile Gln Glu Asn Val Val Leu Pro Gln Ile His Thr Val Thr
    1205            1210            1215

Gly Thr Lys Asn Phe Met Lys Asn Leu Phe Leu Leu Ser Thr Arg
    1220            1225            1230

Gln Asn Val Glu Gly Ser Tyr Asp Gly Ala Tyr Ala Pro Val Leu
    1235            1240            1245

Gln Asp Phe Arg Ser Leu Asn Asp Ser Thr Asn Arg Thr Lys Lys
    1250            1255            1260

His Thr Ala His Phe Ser Lys Lys Gly Glu Glu Glu Asn Leu Glu
    1265            1270            1275

Gly Leu Gly Asn Gln Thr Lys Gln Ile Val Glu Lys Tyr Ala Cys
    1280            1285            1290

Thr Thr Arg Ile Ser Pro Asn Thr Ser Gln Gln Asn Phe Val Thr
    1295            1300            1305

Gln Arg Ser Lys Arg Ala Leu Lys Gln Phe Arg Leu Pro Leu Glu
    1310            1315            1320

Glu Thr Glu Leu Glu Lys Arg Ile Ile Val Asp Asp Thr Ser Thr
```

```
            1325                1330                1335

Gln Trp Ser Lys Asn Met Lys His Leu Thr Pro Ser  Thr Leu Thr
        1340                1345                1350

Gln Ile Asp Tyr Asn Glu Lys Glu Lys Gly Ala Ile  Thr Gln Ser
        1355                1360                1365

Pro Leu Ser Asp Cys Leu Thr Arg Ser His Ser Ile  Pro Gln Ala
        1370                1375                1380

Asn Arg Ser Pro Leu Pro Ile Ala Lys Val Ser Ser  Phe Pro Ser
        1385                1390                1395

Ile Arg Pro Ile Tyr Leu Thr Arg Val Leu Phe Gln  Asp Asn Ser
        1400                1405                1410

Ser His Leu Pro Ala Ala Ser Tyr Arg Lys Lys Asp  Ser Gly Val
        1415                1420                1425

Gln Glu Ser Ser His Phe Leu Gln Gly Ala Lys Lys  Asn Asn Leu
        1430                1435                1440

Ser Leu Ala Ile Leu Thr Leu Glu Met Thr Gly Asp  Gln Arg Glu
        1445                1450                1455

Val Gly Ser Leu Gly Thr Ser Ala Thr Asn Ser Val  Thr Tyr Lys
        1460                1465                1470

Lys Val Glu Asn Thr Val Leu Pro Lys Pro Asp Leu  Pro Lys Thr
        1475                1480                1485

Ser Gly Lys Val Glu Leu Leu Pro Lys Val His Ile  Tyr Gln Lys
        1490                1495                1500

Asp Leu Phe Pro Thr Glu Thr Ser Asn Gly Ser Pro  Gly His Leu
        1505                1510                1515

Asp Leu Val Glu Gly Ser Leu Leu Gln Gly Thr Glu  Gly Ala Ile
        1520                1525                1530

Lys Trp Asn Glu Ala Asn Arg Pro Gly Lys Val Pro  Phe Leu Arg
        1535                1540                1545

Val Ala Thr Glu Ser Ser Ala Lys Thr Pro Ser Lys  Leu Leu Asp
        1550                1555                1560

Pro Leu Ala Trp Asp Asn His Tyr Gly Thr Gln Ile  Pro Lys Glu
        1565                1570                1575

Glu Trp Lys Ser Gln Glu Lys Ser Pro Glu Lys Thr  Ala Phe Lys
        1580                1585                1590

Lys Lys Asp Thr Ile Leu Ser Leu Asn Ala Cys Glu  Ser Asn His
        1595                1600                1605

Ala Ile Ala Ala Ile Asn Glu Gly Gln Asn Lys Pro  Glu Ile Glu
        1610                1615                1620

Val Thr Trp Ala Lys Gln Gly Arg Thr Glu Arg Leu  Cys Ser Gln
        1625                1630                1635

Asn Pro Pro Val Leu Lys Arg His Gln Arg Glu Ile  Thr Arg Thr
        1640                1645                1650

Thr Leu Gln Ser Asp Gln Glu Glu Ile Asp Tyr Asp  Asp Thr Ile
        1655                1660                1665

Ser Val Glu Met Lys Lys Glu Asp Phe Asp Ile Tyr  Asp Glu Asp
        1670                1675                1680

Glu Asn Gln Ser Pro Arg Ser Phe Gln Lys Lys Thr  Arg His Tyr
        1685                1690                1695

Phe Ile Ala Ala Val Glu Arg Leu Trp Asp Tyr Gly  Met Ser Ser
        1700                1705                1710

Ser Pro His Val Leu Arg Asn Arg Ala Gln Ser Gly  Ser Val Pro
        1715                1720                1725
```

```
Gln Phe Lys Lys Val Val Phe Gln Glu Phe Thr Asp Gly Ser Phe
    1730                1735                1740

Thr Gln Pro Leu Tyr Arg Gly Glu Leu Asn Glu His Leu Gly Leu
    1745                1750                1755

Leu Gly Pro Tyr Ile Arg Ala Glu Val Glu Asp Asn Ile Met Val
    1760                1765                1770

Thr Phe Arg Asn Gln Ala Ser Arg Pro Tyr Ser Phe Tyr Ser Ser
    1775                1780                1785

Leu Ile Ser Tyr Glu Glu Asp Gln Arg Gln Gly Ala Glu Pro Arg
    1790                1795                1800

Lys Asn Phe Val Lys Pro Asn Glu Thr Lys Thr Tyr Phe Trp Lys
    1805                1810                1815

Val Gln His His Met Ala Pro Thr Lys Asp Glu Phe Asp Cys Lys
    1820                1825                1830

Ala Trp Ala Tyr Phe Ser Asp Val Asp Leu Glu Lys Asp Val His
    1835                1840                1845

Ser Gly Leu Ile Gly Pro Leu Leu Val Cys His Thr Asn Thr Leu
    1850                1855                1860

Asn Pro Ala His Gly Arg Gln Val Thr Val Gln Glu Phe Ala Leu
    1865                1870                1875

Phe Phe Thr Ile Phe Asp Glu Thr Lys Ser Trp Tyr Phe Thr Glu
    1880                1885                1890

Asn Met Glu Arg Asn Cys Arg Ala Pro Cys Asn Ile Gln Met Glu
    1895                1900                1905

Asp Pro Thr Phe Lys Glu Asn Tyr Arg Phe His Ala Ile Asn Gly
    1910                1915                1920

Tyr Ile Met Asp Thr Leu Pro Gly Leu Val Met Ala Gln Asp Gln
    1925                1930                1935

Arg Ile Arg Trp Tyr Leu Leu Ser Met Gly Ser Asn Glu Asn Ile
    1940                1945                1950

His Ser Ile His Phe Ser Gly His Val Phe Thr Val Arg Lys Lys
    1955                1960                1965

Glu Glu Tyr Lys Met Ala Leu Tyr Asn Leu Tyr Pro Gly Val Phe
    1970                1975                1980

Glu Thr Val Glu Met Leu Pro Ser Lys Ala Gly Ile Trp Arg Val
    1985                1990                1995

Glu Cys Leu Ile Gly Glu His Leu His Ala Gly Met Ser Thr Leu
    2000                2005                2010

Phe Leu Val Tyr Ser Asn Lys Cys Gln Thr Pro Leu Gly Met Ala
    2015                2020                2025

Ser Gly His Ile Arg Asp Phe Gln Ile Thr Ala Ser Gly Gln Tyr
    2030                2035                2040

Gly Gln Trp Ala Pro Lys Leu Ala Arg Leu His Tyr Ser Gly Ser
    2045                2050                2055

Ile Asn Ala Trp Ser Thr Lys Glu Pro Phe Ser Trp Ile Lys Val
    2060                2065                2070

Asp Leu Leu Ala Pro Met Ile Ile His Gly Ile Lys Thr Gln Gly
    2075                2080                2085

Ala Arg Gln Lys Phe Ser Ser Leu Tyr Ile Ser Gln Phe Ile Ile
    2090                2095                2100

Met Tyr Ser Leu Asp Gly Lys Lys Trp Gln Thr Tyr Arg Gly Asn
    2105                2110                2115
```

```
Ser Thr Gly Thr Leu Met Val Phe Phe Gly Asn Val Asp Ser Ser
    2120                2125                2130

Gly Ile Lys His Asn Ile Phe Asn Pro Pro Ile Ile Ala Arg Tyr
    2135                2140                2145

Ile Arg Leu His Pro Thr His Tyr Ser Ile Arg Ser Thr Leu Arg
    2150                2155                2160

Met Glu Leu Met Gly Cys Asp Leu Asn Ser Cys Ser Met Pro Leu
    2165                2170                2175

Gly Met Glu Ser Lys Ala Ile Ser Asp Ala Gln Ile Thr Ala Ser
    2180                2185                2190

Ser Tyr Phe Thr Asn Met Phe Ala Thr Trp Ser Pro Ser Lys Ala
    2195                2200                2205

Arg Leu His Leu Gln Gly Arg Ser Asn Ala Trp Arg Pro Gln Val
    2210                2215                2220

Asn Asn Pro Lys Glu Trp Leu Gln Val Asp Phe Gln Lys Thr Met
    2225                2230                2235

Lys Val Thr Gly Val Thr Thr Gln Gly Val Lys Ser Leu Leu Thr
    2240                2245                2250

Ser Met Tyr Val Lys Glu Phe Leu Ile Ser Ser Ser Gln Asp Gly
    2255                2260                2265

His Gln Trp Thr Leu Phe Phe Gln Asn Gly Lys Val Lys Val Phe
    2270                2275                2280

Gln Gly Asn Gln Asp Ser Phe Thr Pro Val Val Asn Ser Leu Asp
    2285                2290                2295

Pro Pro Leu Leu Thr Arg Tyr Leu Arg Ile His Pro Gln Ser Trp
    2300                2305                2310

Val His Gln Ile Ala Leu Arg Met Glu Val Leu Gly Cys Glu Ala
    2315                2320                2325

Gln Asp Leu Tyr
    2330

<210> SEQ ID NO 9
<211> LENGTH: 2324
<212> TYPE: PRT
<213> ORGANISM: canis familiaris

<400> SEQUENCE: 9

Ala Thr Arg Lys Tyr Tyr Leu Gly Ala Val Glu Leu Ser Trp Asp Tyr
1               5                   10                  15

Met Gln Ser Asp Leu Leu Ser Ala Leu His Ala Asp Thr Ser Phe Ser
                20                  25                  30

Ser Arg Val Pro Gly Ser Leu Pro Leu Thr Thr Ser Val Thr Tyr Arg
            35                  40                  45

Lys Thr Val Phe Val Glu Phe Thr Asp Asp Leu Phe Asn Ile Ala Lys
        50                  55                  60

Pro Arg Pro Pro Trp Met Gly Leu Leu Gly Pro Thr Ile Gln Ala Glu
65                  70                  75                  80

Val Tyr Asp Thr Val Val Ile Val Leu Lys Asn Met Ala Ser His Pro
                85                  90                  95

Val Ser Leu His Ala Val Gly Val Ser Tyr Trp Lys Ala Ser Glu Gly
            100                 105                 110

Ala Glu Tyr Glu Asp Gln Thr Ser Gln Lys Glu Lys Glu Asp Asp Asn
        115                 120                 125

Val Ile Pro Gly Glu Ser His Thr Tyr Val Trp Gln Val Leu Lys Glu
    130                 135                 140
```

```
Asn Gly Pro Met Ala Ser Asp Pro Cys Leu Thr Tyr Ser Tyr Phe
145                 150                 155                 160

Ser His Val Asp Leu Val Lys Asp Leu Asn Ser Gly Leu Ile Gly Ala
        165                 170                 175

Leu Leu Val Cys Lys Glu Gly Ser Leu Ala Lys Glu Arg Thr Gln Thr
            180                 185                 190

Leu Gln Glu Phe Val Leu Leu Phe Ala Val Phe Asp Glu Gly Lys Ser
                195                 200                 205

Trp His Ser Glu Thr Asn Ala Ser Leu Thr Gln Ala Glu Ala Gln His
    210                 215                 220

Glu Leu His Thr Ile Asn Gly Tyr Val Asn Arg Ser Leu Pro Gly Leu
225                 230                 235                 240

Thr Val Cys His Lys Arg Ser Val Tyr Trp His Val Ile Gly Met Gly
            245                 250                 255

Thr Thr Pro Glu Val His Ser Ile Phe Leu Glu Gly His Thr Phe Leu
                260                 265                 270

Val Arg Asn His Arg Gln Ala Ser Leu Glu Ile Ser Pro Ile Thr Phe
            275                 280                 285

Leu Thr Ala Gln Thr Phe Leu Met Asp Leu Gly Gln Phe Leu Leu Phe
290                 295                 300

Cys His Ile Pro Ser His Gln His Asp Gly Met Glu Ala Tyr Val Lys
305                 310                 315                 320

Val Asp Ser Cys Pro Glu Glu Pro Gln Leu Arg Met Lys Asn Asn Glu
            325                 330                 335

Asp Lys Asp Tyr Asp Asp Gly Leu Tyr Asp Ser Asp Met Asp Val Val
            340                 345                 350

Ser Phe Asp Asp Asp Ser Ser Pro Phe Ile Gln Ile Arg Ser Val
            355                 360                 365

Ala Lys Lys His Pro Lys Thr Trp Val His Tyr Ile Ala Ala Glu Glu
    370                 375                 380

Glu Asp Trp Asp Tyr Ala Pro Ser Gly Pro Thr Pro Asn Asp Arg Ser
385                 390                 395                 400

His Lys Asn Leu Tyr Leu Asn Asn Gly Pro Gln Arg Ile Gly Lys Lys
                405                 410                 415

Tyr Lys Lys Val Arg Phe Val Ala Tyr Thr Asp Glu Thr Phe Lys Thr
            420                 425                 430

Arg Glu Ala Ile Gln Tyr Glu Ser Gly Ile Leu Gly Pro Leu Leu Tyr
        435                 440                 445

Gly Glu Val Gly Asp Thr Leu Leu Ile Ile Phe Lys Asn Gln Ala Ser
    450                 455                 460

Arg Pro Tyr Asn Ile Tyr Pro His Gly Ile Asn Tyr Val Thr Pro Leu
465                 470                 475                 480

His Thr Gly Arg Leu Pro Lys Gly Val Lys His Leu Lys Asp Met Pro
            485                 490                 495

Ile Leu Pro Gly Glu Ile Phe Lys Tyr Lys Trp Thr Val Thr Val Glu
            500                 505                 510

Asp Gly Pro Thr Lys Ser Asp Pro Arg Cys Leu Thr Arg Tyr Tyr Ser
            515                 520                 525

Ser Phe Ile Asn Leu Glu Arg Asp Leu Ala Ser Gly Leu Ile Gly Pro
            530                 535                 540

Leu Leu Ile Cys Tyr Lys Glu Ser Val Asp Gln Arg Gly Asn Gln Met
545                 550                 555                 560
```

-continued

```
Met Ser Asp Lys Arg Asn Val Ile Leu Phe Ser Val Phe Asp Glu Asn
            565                 570                 575

Arg Ser Trp Tyr Leu Thr Glu Asn Met Gln Arg Phe Leu Pro Asn Ala
        580                 585                 590

Asp Val Val Gln Pro His Asp Pro Glu Phe Gln Leu Ser Asn Ile Met
            595                 600                 605

His Ser Ile Asn Gly Tyr Val Phe Asp Asn Leu Gln Leu Ser Val Cys
        610                 615                 620

Leu His Glu Val Ala Tyr Trp Tyr Ile Leu Ser Val Gly Ala Gln Thr
625                 630                 635                 640

Asp Phe Leu Ser Val Phe Phe Ser Gly Tyr Thr Phe Lys His Lys Met
            645                 650                 655

Val Tyr Glu Asp Thr Leu Thr Leu Phe Pro Phe Ser Gly Glu Thr Val
        660                 665                 670

Phe Met Ser Met Glu Asn Pro Gly Leu Trp Val Leu Gly Cys His Asn
            675                 680                 685

Ser Asp Phe Arg Asn Arg Gly Met Thr Ala Leu Leu Lys Val Ser Ser
        690                 695                 700

Cys Asn Arg Asn Ile Asp Asp Tyr Tyr Glu Asp Thr Tyr Glu Asp Ile
705                 710                 715                 720

Pro Thr Pro Leu Leu Asn Glu Asn Asn Val Ile Lys Pro Arg Ser Phe
            725                 730                 735

Ser Gln Asn Ser Arg His Pro Ser Thr Lys Glu Lys Gln Leu Lys Ala
        740                 745                 750

Thr Thr Thr Pro Glu Asn Asp Ile Glu Lys Ile Asp Leu Gln Ser Gly
            755                 760                 765

Glu Arg Thr Gln Leu Ile Lys Ala Gln Ser Val Ser Ser Ser Asp Leu
        770                 775                 780

Leu Met Leu Leu Gly Gln Asn Pro Thr Pro Arg Gly Leu Phe Leu Ser
785                 790                 795                 800

Asp Leu Arg Glu Ala Thr Asp Arg Ala Asp His Ser Arg Gly Ala
            805                 810                 815

Ile Glu Arg Asn Lys Gly Pro Pro Glu Val Ala Ser Leu Arg Pro Glu
        820                 825                 830

Leu Arg His Ser Glu Asp Arg Glu Phe Thr Pro Glu Pro Glu Leu Gln
            835                 840                 845

Leu Arg Leu Asn Glu Asn Leu Gly Thr Asn Thr Thr Val Glu Leu Lys
        850                 855                 860

Lys Leu Asp Leu Lys Ile Ser Ser Ser Ser Asp Ser Leu Met Thr Ser
865                 870                 875                 880

Pro Thr Ile Pro Ser Asp Lys Leu Ala Ala Ala Thr Glu Lys Thr Gly
            885                 890                 895

Ser Leu Gly Pro Pro Asn Met Ser Val His Phe Asn Ser His Leu Gly
        900                 905                 910

Thr Ile Val Phe Gly Asn Asn Ser Ser His Leu Ile Gln Ser Gly Val
            915                 920                 925

Pro Leu Glu Leu Ser Glu Glu Asp Asn Asp Ser Lys Leu Leu Glu Ala
        930                 935                 940

Pro Leu Met Asn Ile Gln Glu Ser Ser Leu Arg Glu Asn Val Leu Ser
945                 950                 955                 960

Met Glu Ser Asn Arg Leu Phe Lys Glu Glu Arg Ile Arg Gly Pro Ala
            965                 970                 975

Ser Leu Ile Lys Asp Asn Ala Leu Phe Lys Val Asn Ile Ser Ser Val
```

-continued

```
                980             985             990
Lys Thr Asn Arg Ala Pro Val Asn Leu Thr Thr Asn Arg Lys Thr Arg
                    995            1000            1005
Val Ala Ile Pro Thr Leu Leu Ile Glu Asn Ser Thr Ser Val Trp
    1010            1015            1020
Gln Asp Ile Met Leu Glu Arg Asn Thr Glu Phe Lys Glu Val Thr
    1025            1030            1035
Ser Leu Ile His Asn Glu Thr Phe Met Asp Arg Asn Thr Thr Ala
    1040            1045            1050
Leu Gly Leu Asn His Val Ser Asn Lys Thr Thr Leu Ser Lys Asn
    1055            1060            1065
Val Glu Met Ala His Gln Lys Lys Glu Asp Pro Val Pro Leu Arg
    1070            1075            1080
Ala Glu Asn Pro Asp Leu Ser Ser Ser Lys Ile Pro Phe Leu Pro
    1085            1090            1095
Asp Trp Ile Lys Thr His Gly Lys Asn Ser Leu Ser Ser Glu Gln
    1100            1105            1110
Arg Pro Ser Pro Lys Gln Leu Thr Ser Leu Gly Ser Glu Lys Ser
    1115            1120            1125
Val Lys Asp Gln Asn Phe Leu Ser Glu Glu Lys Val Val Val Gly
    1130            1135            1140
Glu Asp Glu Phe Thr Lys Asp Thr Glu Leu Gln Glu Ile Phe Pro
    1145            1150            1155
Asn Asn Lys Ser Ile Phe Phe Ala Asn Leu Ala Asn Val Gln Glu
    1160            1165            1170
Asn Asp Thr Tyr Asn Gln Glu Lys Lys Ser Pro Glu Glu Ile Glu
    1175            1180            1185
Arg Lys Glu Lys Leu Thr Gln Glu Asn Val Ala Leu Pro Gln Ala
    1190            1195            1200
His Thr Met Ile Gly Thr Lys Asn Phe Leu Lys Asn Leu Phe Leu
    1205            1210            1215
Leu Ser Thr Lys Gln Asn Val Ala Gly Leu Glu Glu Gln Pro Tyr
    1220            1225            1230
Thr Pro Ile Leu Gln Asp Thr Arg Ser Leu Asn Asp Ser Pro His
    1235            1240            1245
Ser Glu Gly Ile His Met Ala Asn Phe Ser Lys Ile Arg Glu Glu
    1250            1255            1260
Ala Asn Leu Glu Gly Leu Gly Asn Gln Thr Asn Gln Met Val Glu
    1265            1270            1275
Arg Phe Pro Ser Thr Thr Arg Met Ser Ser Asn Ala Ser Gln His
    1280            1285            1290
Val Ile Thr Gln Arg Gly Lys Arg Ser Leu Lys Gln Pro Arg Leu
    1295            1300            1305
Ser Gln Gly Glu Ile Lys Phe Glu Arg Lys Val Ile Ala Asn Asp
    1310            1315            1320
Thr Ser Thr Gln Trp Ser Lys Asn Met Asn Tyr Leu Ala Gln Gly
    1325            1330            1335
Thr Leu Thr Gln Ile Glu Tyr Asn Glu Lys Glu Lys Arg Ala Ile
    1340            1345            1350
Thr Gln Ser Pro Leu Ser Asp Cys Ser Met Arg Asn His Val Thr
    1355            1360            1365
Ile Gln Met Asn Asp Ser Ala Leu Pro Val Ala Lys Glu Ser Ala
    1370            1375            1380
```

-continued

```
Ser Pro Ser Val Arg His Thr Asp Leu Thr Lys Ile Pro Ser Gln
    1385                1390                1395

His Asn Ser Ser His Leu Pro Ala Ser Ala Cys Asn Tyr Thr Phe
    1400                1405                1410

Arg Glu Arg Thr Ser Gly Val Gln Glu Gly Ser His Phe Leu Gln
    1415                1420                1425

Glu Ala Lys Arg Asn Asn Leu Ser Leu Ala Phe Val Thr Leu Gly
    1430                1435                1440

Ile Thr Glu Gly Gln Gly Lys Phe Ser Ser Leu Gly Lys Ser Ala
    1445                1450                1455

Thr Asn Gln Pro Met Tyr Lys Lys Leu Glu Asn Thr Val Leu Leu
    1460                1465                1470

Gln Pro Gly Leu Ser Glu Thr Ser Asp Lys Val Glu Leu Leu Ser
    1475                1480                1485

Gln Val His Val Asp Gln Glu Asp Ser Phe Pro Thr Lys Thr Ser
    1490                1495                1500

Asn Asp Ser Pro Gly His Leu Asp Leu Met Gly Lys Ile Phe Leu
    1505                1510                1515

Gln Lys Thr Gln Gly Pro Val Lys Met Asn Lys Thr Asn Ser Pro
    1520                1525                1530

Gly Lys Val Pro Phe Leu Lys Trp Ala Thr Glu Ser Ser Glu Lys
    1535                1540                1545

Ile Pro Ser Lys Leu Leu Gly Val Leu Ala Trp Asp Asn His Tyr
    1550                1555                1560

Asp Thr Gln Ile Pro Ser Glu Glu Trp Lys Ser Gln Lys Lys Ser
    1565                1570                1575

Gln Thr Asn Thr Ala Phe Lys Arg Lys Asp Thr Ile Leu Pro Leu
    1580                1585                1590

Gly Pro Cys Glu Asn Asn Asp Ser Thr Ala Ala Ile Asn Glu Gly
    1595                1600                1605

Gln Asp Lys Pro Gln Arg Glu Ala Met Trp Ala Lys Gln Gly Glu
    1610                1615                1620

Pro Gly Arg Leu Cys Ser Gln Asn Pro Pro Val Ser Lys His His
    1625                1630                1635

Gln Arg Glu Ile Thr Val Thr Thr Leu Gln Pro Glu Glu Asp Lys
    1640                1645                1650

Phe Glu Tyr Asp Asp Thr Phe Ser Ile Glu Met Lys Arg Glu Asp
    1655                1660                1665

Phe Asp Ile Tyr Gly Asp Tyr Glu Asn Gln Gly Leu Arg Ser Phe
    1670                1675                1680

Gln Lys Lys Thr Arg His Tyr Phe Ile Ala Ala Val Glu Arg Leu
    1685                1690                1695

Trp Asp Tyr Gly Met Ser Arg Ser Pro His Ile Leu Arg Asn Arg
    1700                1705                1710

Ala Gln Ser Gly Asp Val Gln Gln Phe Lys Lys Val Val Phe Gln
    1715                1720                1725

Glu Phe Thr Asp Gly Ser Phe Thr Gln Pro Leu Tyr Arg Gly Glu
    1730                1735                1740

Leu Asn Glu His Leu Gly Leu Leu Gly Pro Tyr Ile Arg Ala Glu
    1745                1750                1755

Val Glu Asp Asn Ile Val Val Thr Phe Lys Asn Gln Ala Ser Arg
    1760                1765                1770
```

```
Pro Tyr Ser Phe Tyr Ser Ser Leu Ile Ser Tyr Asp Glu Asp Glu
    1775                1780                1785

Gly Gln Gly Ala Glu Pro Arg Arg Lys Phe Val Asn Pro Asn Glu
    1790                1795                1800

Thr Lys Ile Tyr Phe Trp Lys Val Gln His His Met Ala Pro Thr
    1805                1810                1815

Lys Asp Glu Phe Asp Cys Lys Ala Trp Ala Tyr Phe Ser Asp Val
    1820                1825                1830

Asp Leu Glu Lys Asp Val His Ser Gly Leu Ile Gly Pro Leu Leu
    1835                1840                1845

Ile Cys Arg Ser Asn Thr Leu Asn Pro Ala His Gly Arg Gln Val
    1850                1855                1860

Thr Val Gln Glu Phe Ala Leu Val Phe Thr Ile Phe Asp Glu Thr
    1865                1870                1875

Lys Ser Trp Tyr Phe Thr Glu Asn Leu Glu Arg Asn Cys Arg Ala
    1880                1885                1890

Pro Cys Asn Val Gln Lys Glu Asp Pro Thr Leu Lys Glu Asn Phe
    1895                1900                1905

Arg Phe His Ala Ile Asn Gly Tyr Val Lys Asp Thr Leu Pro Gly
    1910                1915                1920

Leu Val Met Ala Gln Asp Gln Lys Val Arg Trp Tyr Leu Leu Ser
    1925                1930                1935

Met Gly Ser Asn Glu Asn Ile His Ser Ile His Phe Ser Gly His
    1940                1945                1950

Val Phe Thr Val Arg Lys Lys Glu Glu Tyr Lys Met Ala Val Tyr
    1955                1960                1965

Asn Leu Tyr Pro Gly Val Phe Glu Thr Val Glu Met Leu Pro Ser
    1970                1975                1980

Gln Val Gly Ile Trp Arg Ile Glu Cys Leu Ile Gly Glu His Leu
    1985                1990                1995

Gln Ala Gly Met Ser Thr Leu Phe Leu Val Tyr Ser Lys Lys Cys
    2000                2005                2010

Gln Thr Pro Leu Gly Met Ala Ser Gly His Ile Arg Asp Phe Gln
    2015                2020                2025

Ile Thr Ala Ser Gly Gln Tyr Gly Gln Trp Ala Pro Lys Leu Ala
    2030                2035                2040

Arg Leu His Tyr Ser Gly Ser Ile Asn Ala Trp Ser Thr Lys Asp
    2045                2050                2055

Pro Phe Ser Trp Ile Lys Val Asp Leu Leu Ala Pro Met Ile Ile
    2060                2065                2070

His Gly Ile Met Thr Gln Gly Ala Arg Gln Lys Phe Ser Ser Leu
    2075                2080                2085

Tyr Val Ser Gln Phe Ile Ile Met Tyr Ser Leu Asp Gly Asn Lys
    2090                2095                2100

Trp His Ser Tyr Arg Gly Asn Ser Thr Gly Thr Leu Met Val Phe
    2105                2110                2115

Phe Gly Asn Val Asp Ser Ser Gly Ile Lys His Asn Ile Phe Asn
    2120                2125                2130

Pro Pro Ile Ile Ala Gln Tyr Ile Arg Leu His Pro Thr His Tyr
    2135                2140                2145

Ser Ile Arg Ser Thr Leu Arg Met Glu Leu Leu Gly Cys Asp Phe
    2150                2155                2160

Asn Ser Cys Ser Met Pro Leu Gly Met Glu Ser Lys Ala Ile Ser
```

```
            2165                2170                2175

Asp Ala Gln Ile Thr Ala Ser Ser Tyr Leu Ser Ser Met Leu Ala
        2180                2185                2190

Thr Trp Ser Pro Ser Gln Ala Arg Leu His Leu Gln Gly Arg Thr
    2195                2200                2205

Asn Ala Trp Arg Pro Gln Ala Asn Asn Pro Lys Glu Trp Leu Gln
    2210                2215                2220

Val Asp Phe Arg Lys Thr Met Lys Val Thr Gly Ile Thr Thr Gln
    2225                2230                2235

Gly Val Lys Ser Leu Leu Ile Ser Met Tyr Val Lys Glu Phe Leu
    2240                2245                2250

Ile Ser Ser Ser Gln Asp Gly His Asn Trp Thr Leu Phe Leu Gln
    2255                2260                2265

Asn Gly Lys Val Lys Val Phe Gln Gly Asn Arg Asp Ser Ser Thr
    2270                2275                2280

Pro Val Arg Asn Arg Leu Glu Pro Pro Leu Val Ala Arg Tyr Val
    2285                2290                2295

Arg Leu His Pro Gln Ser Trp Ala His His Ile Ala Leu Arg Leu
    2300                2305                2310

Glu Val Leu Gly Cys Asp Thr Gln Gln Pro Ala
    2315                2320

<210> SEQ ID NO 10
<211> LENGTH: 27
<212> TYPE: PRT
<213> ORGANISM: Sus scrofa

<400> SEQUENCE: 10

Asp Ile Gly Asp Tyr Tyr Asp Asn Thr Tyr Glu Asp Ile Pro Gly Phe
1               5                   10                  15

Leu Leu Ser Gly Lys Asn Val Ile Glu Pro Arg
            20                  25

<210> SEQ ID NO 11
<211> LENGTH: 27
<212> TYPE: PRT
<213> ORGANISM: Homo sapiens

<400> SEQUENCE: 11

Asn Thr Gly Asp Tyr Tyr Glu Asp Ser Tyr Glu Asp Ile Ser Ala Tyr
1               5                   10                  15

Leu Leu Ser Lys Asn Asn Ala Ile Glu Pro Arg
            20                  25

<210> SEQ ID NO 12
<211> LENGTH: 27
<212> TYPE: PRT
<213> ORGANISM: Canis familiaris

<400> SEQUENCE: 12

Asn Ile Asp Asp Tyr Tyr Glu Asp Thr Tyr Glu Asp Ile Pro Thr Pro
1               5                   10                  15

Leu Leu Asn Glu Asn Asn Val Ile Lys Pro Arg
            20                  25

<210> SEQ ID NO 13
<211> LENGTH: 2332
<212> TYPE: PRT
<213> ORGANISM: Homo sapiens
```

<400> SEQUENCE: 13

```
Ala Thr Arg Arg Tyr Tyr Leu Gly Ala Val Glu Leu Ser Trp Asp Tyr
 1               5                  10                  15

Met Gln Ser Asp Leu Gly Glu Leu Pro Val Asp Ala Arg Phe Pro Pro
             20                  25                  30

Arg Val Pro Lys Ser Phe Pro Phe Asn Thr Ser Val Val Tyr Lys Lys
         35                  40                  45

Thr Leu Phe Val Glu Phe Thr Asp His Leu Phe Asn Ile Ala Lys Pro
     50                  55                  60

Arg Pro Pro Trp Met Gly Leu Leu Gly Pro Thr Ile Gln Ala Glu Val
 65                  70                  75                  80

Tyr Asp Thr Val Ile Thr Leu Lys Asn Met Ala Ser His Pro Val
                 85                  90                  95

Ser Leu His Ala Val Gly Val Ser Tyr Trp Lys Ala Ser Glu Gly Ala
                100                 105                 110

Glu Tyr Asp Asp Gln Thr Ser Gln Arg Glu Lys Glu Asp Asp Lys Val
            115                 120                 125

Phe Pro Gly Gly Ser His Thr Tyr Val Trp Gln Val Leu Lys Glu Asn
130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Leu Thr Asp
            340                 345                 350

Ser Glu Met Asp Val Val Arg Phe Asp Asp Asn Ser Pro Ser Phe
        355                 360                 365

Ile Gln Ile Arg Ser Val Ala Lys Lys His Pro Lys Thr Trp Val His
    370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
```

-continued

```
                405                 410                 415
Gln Arg Ile Gly Arg Lys Tyr Lys Val Arg Phe Met Ala Tyr Thr
            420                 425                 430
Asp Glu Thr Phe Lys Thr Arg Glu Ala Ile Gln His Glu Ser Gly Ile
            435                 440                 445
Leu Gly Pro Leu Leu Tyr Gly Glu Val Gly Asp Thr Leu Leu Ile Ile
            450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
                500                 505                 510
Trp Thr Val Thr Val Glu Asp Gly Pro Thr Lys Ser Asp Pro Arg Cys
                515                 520                 525
Leu Thr Arg Tyr Tyr Ser Ser Phe Val Asn Met Glu Arg Asp Leu Ala
            530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
            580                 585                 590
Arg Phe Leu Pro Asn Pro Ala Gly Val Gln Leu Glu Asp Pro Glu Phe
            595                 600                 605
Gln Ala Ser Asn Ile Met His Ser Ile Asn Gly Tyr Val Phe Asp Ser
        610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
Thr Phe Lys His Lys Met Val Tyr Glu Asp Thr Leu Thr Leu Phe Pro
            660                 665                 670
Phe Ser Gly Glu Thr Val Phe Met Ser Met Glu Asn Pro Gly Leu Trp
            675                 680                 685
Ile Leu Gly Cys His Asn Ser Asp Phe Arg Asn Arg Gly Met Thr Ala
        690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                725                 730                 735
Ile Glu Pro Arg Ser Phe Ser Gln Asn Ser Arg His Pro Ser Thr Arg
            740                 745                 750
Gln Lys Gln Phe Asn Ala Thr Thr Ile Pro Glu Asn Asp Ile Glu Lys
            755                 760                 765
Thr Asp Pro Trp Phe Ala His Arg Thr Pro Met Pro Lys Ile Gln Asn
        770                 775                 780
Val Ser Ser Ser Asp Leu Leu Met Leu Leu Arg Gln Ser Pro Thr Pro
785                 790                 795                 800
His Gly Leu Ser Leu Ser Asp Leu Gln Glu Ala Lys Tyr Glu Thr Phe
                805                 810                 815
Ser Asp Asp Pro Ser Pro Gly Ala Ile Asp Ser Asn Asn Ser Leu Ser
            820                 825                 830
```

Glu Met Thr His Phe Arg Pro Gln Leu His His Ser Gly Asp Met Val
        835                 840                 845

Phe Thr Pro Glu Ser Gly Leu Gln Leu Arg Leu Asn Glu Lys Leu Gly
850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
        885                 890                 895

Gly Thr Asp Asn Thr Ser Ser Leu Gly Pro Pro Ser Met Pro Val His
            900                 905                 910

Tyr Asp Ser Gln Leu Asp Thr Thr Leu Phe Gly Lys Lys Ser Ser Pro
        915                 920                 925

Leu Thr Glu Ser Gly Gly Pro Leu Ser Leu Ser Glu Glu Asn Asn Asp
    930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
        995                 1000                1005

Thr Asn Arg Lys Thr His Ile Asp Gly Pro Ser Leu Leu Ile Glu
    1010                1015                1020

Asn Ser Pro Ser Val Trp Gln Asn Ile Leu Glu Ser Asp Thr Glu
    1025                1030                1035

Phe Lys Lys Val Thr Pro Leu Ile His Asp Arg Met Leu Met Asp
    1040                1045                1050

Lys Asn Ala Thr Ala Leu Arg Leu Asn His Met Ser Asn Lys Thr
    1055                1060                1065

Thr Ser Ser Lys Asn Met Glu Met Val Gln Gln Lys Lys Glu Gly
    1070                1075                1080

Pro Ile Pro Pro Asp Ala Gln Asn Pro Asp Met Ser Phe Phe Lys
    1085                1090                1095

Met Leu Phe Leu Pro Glu Ser Ala Arg Trp Ile Gln Arg Thr His
    1100                1105                1110

Gly Lys Asn Ser Leu Asn Ser Gly Gln Gly Pro Ser Pro Lys Gln
    1115                1120                1125

Leu Val Ser Leu Gly Pro Glu Lys Ser Val Glu Gly Gln Asn Phe
    1130                1135                1140

Leu Ser Glu Lys Asn Lys Val Val Val Gly Lys Gly Glu Phe Thr
    1145                1150                1155

Lys Asp Val Gly Leu Lys Glu Met Val Phe Pro Ser Ser Arg Asn
    1160                1165                1170

Leu Phe Leu Thr Asn Leu Asp Asn Leu His Glu Asn Asn Thr His
    1175                1180                1185

Asn Gln Glu Lys Lys Ile Gln Glu Glu Ile Glu Lys Lys Glu Thr
    1190                1195                1200

Leu Ile Gln Glu Asn Val Val Leu Pro Gln Ile His Thr Val Thr
    1205                1210                1215

Gly Thr Lys Asn Phe Met Lys Asn Leu Phe Leu Leu Ser Thr Arg
    1220                1225                1230

-continued

| | | | | | | | | | | | |
|---|---|---|---|---|---|---|---|---|---|---|---|
|Gln|Asn|Val|Glu|Gly|Ser|Tyr|Asp|Gly|Ala|Tyr|Ala|Pro|Val|Leu|
|1235| | | | |1240| | | |1245| | | | | |

Gln Asn Val Glu Gly Ser Tyr Asp Gly Ala Tyr Ala Pro Val Leu
1235                1240            1245

Gln Asp Phe Arg Ser Leu Asn Asp Ser Thr Asn Arg Thr Lys Lys
1250                1255            1260

His Thr Ala His Phe Ser Lys Lys Gly Glu Glu Asn Leu Glu
1265                1270            1275

Gly Leu Gly Asn Gln Thr Lys Gln Ile Val Glu Lys Tyr Ala Cys
1280                1285            1290

Thr Thr Arg Ile Ser Pro Asn Thr Ser Gln Gln Asn Phe Val Thr
1295                1300            1305

Gln Arg Ser Lys Arg Ala Leu Lys Gln Phe Arg Leu Pro Leu Glu
1310                1315            1320

Glu Thr Glu Leu Glu Lys Arg Ile Ile Val Asp Thr Ser Thr
1325                1330            1335

Gln Trp Ser Lys Asn Met Lys His Leu Thr Pro Ser Thr Leu Thr
1340                1345            1350

Gln Ile Asp Tyr Asn Glu Lys Glu Lys Gly Ala Ile Thr Gln Ser
1355                1360            1365

Pro Leu Ser Asp Cys Leu Thr Arg Ser His Ser Ile Pro Gln Ala
1370                1375            1380

Asn Arg Ser Pro Leu Pro Ile Ala Lys Val Ser Phe Pro Ser
1385                1390            1395

Ile Arg Pro Ile Tyr Leu Thr Arg Val Leu Phe Gln Asp Asn Ser
1400                1405            1410

Ser His Leu Pro Ala Ala Ser Tyr Arg Lys Lys Asp Ser Gly Val
1415                1420            1425

Gln Glu Ser Ser His Phe Leu Gln Gly Ala Lys Lys Asn Asn Leu
1430                1435            1440

Ser Leu Ala Ile Leu Thr Leu Glu Met Thr Gly Asp Gln Arg Glu
1445                1450            1455

Val Gly Ser Leu Gly Thr Ser Ala Thr Asn Ser Val Thr Tyr Lys
1460                1465            1470

Lys Val Glu Asn Thr Val Leu Pro Lys Pro Asp Leu Pro Lys Thr
1475                1480            1485

Ser Gly Lys Val Glu Leu Leu Pro Lys Val His Ile Tyr Gln Lys
1490                1495            1500

Asp Leu Phe Pro Thr Glu Thr Ser Asn Gly Ser Pro Gly His Leu
1505                1510            1515

Asp Leu Val Glu Gly Ser Leu Leu Gln Gly Thr Glu Gly Ala Ile
1520                1525            1530

Lys Trp Asn Glu Ala Asn Arg Pro Gly Lys Val Pro Phe Leu Arg
1535                1540            1545

Val Ala Thr Glu Ser Ser Ala Lys Thr Pro Ser Lys Leu Leu Asp
1550                1555            1560

Pro Leu Ala Trp Asp Asn His Tyr Gly Thr Gln Ile Pro Lys Glu
1565                1570            1575

Glu Trp Lys Ser Gln Glu Lys Ser Pro Glu Lys Thr Ala Phe Lys
1580                1585            1590

Lys Lys Asp Thr Ile Leu Ser Leu Asn Ala Cys Glu Ser Asn His
1595                1600            1605

Ala Ile Ala Ala Ile Asn Glu Gly Gln Asn Lys Pro Glu Ile Glu
1610                1615            1620

Val Thr Trp Ala Lys Gln Gly Arg Thr Glu Arg Leu Cys Ser Gln

```
            1625                1630                1635
Asn Pro Pro Val Leu Lys Arg His Gln Arg Glu Ile Thr Arg Thr
            1640                1645                1650
Thr Leu Gln Ser Asp Gln Glu Glu Ile Asp Tyr Asp Asp Thr Ile
            1655                1660                1665
Ser Val Glu Met Lys Lys Glu Asp Phe Asp Ile Tyr Asp Glu Asp
            1670                1675                1680
Glu Asn Gln Ser Pro Arg Ser Phe Gln Lys Lys Thr Arg His Tyr
            1685                1690                1695
Phe Ile Ala Ala Val Glu Arg Leu Trp Asp Tyr Gly Met Ser Ser
            1700                1705                1710
Ser Pro His Val Leu Arg Asn Arg Ala Gln Ser Gly Ser Val Pro
            1715                1720                1725
Gln Phe Lys Lys Val Val Phe Gln Glu Phe Thr Asp Gly Ser Phe
            1730                1735                1740
Thr Gln Pro Leu Tyr Arg Gly Glu Leu Asn Glu His Leu Gly Leu
            1745                1750                1755
Leu Gly Pro Tyr Ile Arg Ala Glu Val Glu Asp Asn Ile Met Val
            1760                1765                1770
Thr Phe Arg Asn Gln Ala Ser Arg Pro Tyr Ser Phe Tyr Ser Ser
            1775                1780                1785
Leu Ile Ser Tyr Glu Glu Asp Gln Arg Gln Gly Ala Glu Pro Arg
            1790                1795                1800
Lys Asn Phe Val Lys Pro Asn Glu Thr Lys Thr Tyr Phe Trp Lys
            1805                1810                1815
Val Gln His His Met Ala Pro Thr Lys Asp Glu Phe Asp Cys Lys
            1820                1825                1830
Ala Trp Ala Tyr Phe Ser Asp Val Asp Leu Glu Lys Asp Val His
            1835                1840                1845
Ser Gly Leu Ile Gly Pro Leu Leu Val Cys His Thr Asn Thr Leu
            1850                1855                1860
Asn Pro Ala His Gly Arg Gln Val Thr Val Gln Glu Phe Ala Leu
            1865                1870                1875
Phe Phe Thr Ile Phe Asp Glu Thr Lys Ser Trp Tyr Phe Thr Glu
            1880                1885                1890
Asn Met Glu Arg Asn Cys Arg Ala Pro Cys Asn Ile Gln Met Glu
            1895                1900                1905
Asp Pro Thr Phe Lys Glu Asn Tyr Arg Phe His Ala Ile Asn Gly
            1910                1915                1920
Tyr Ile Met Asp Thr Leu Pro Gly Leu Val Met Ala Gln Asp Gln
            1925                1930                1935
Arg Ile Arg Trp Tyr Leu Leu Ser Met Gly Ser Asn Glu Asn Ile
            1940                1945                1950
His Ser Ile His Phe Ser Gly His Val Phe Thr Val Arg Lys Lys
            1955                1960                1965
Glu Glu Tyr Lys Met Ala Leu Tyr Asn Leu Tyr Pro Gly Val Phe
            1970                1975                1980
Glu Thr Val Glu Met Leu Pro Ser Lys Ala Gly Ile Trp Arg Val
            1985                1990                1995
Glu Cys Leu Ile Gly Glu His Leu His Ala Gly Met Ser Thr Leu
            2000                2005                2010
Phe Leu Val Tyr Ser Asn Lys Cys Gln Thr Pro Leu Gly Met Ala
            2015                2020                2025
```

Ser Gly His Ile Arg Asp Phe Gln Ile Thr Ala Ser Gly Gln Tyr
2030                2035                2040

Gly Gln Trp Ala Pro Lys Leu Ala Arg Leu His Tyr Ser Gly Ser
    2045                2050                2055

Ile Asn Ala Trp Ser Thr Lys Glu Pro Phe Ser Trp Ile Lys Val
2060                2065                2070

Asp Leu Leu Ala Pro Met Ile Ile His Gly Ile Lys Thr Gln Gly
2075                2080                2085

Ala Arg Gln Lys Phe Ser Ser Leu Tyr Ile Ser Gln Phe Ile Ile
2090                2095                2100

Met Tyr Ser Leu Asp Gly Lys Lys Trp Gln Thr Tyr Arg Gly Asn
2105                2110                2115

Ser Thr Gly Thr Leu Met Val Phe Phe Gly Asn Val Asp Ser Ser
2120                2125                2130

Gly Ile Lys His Asn Ile Phe Asn Pro Pro Ile Ile Ala Arg Tyr
2135                2140                2145

Ile Arg Leu His Pro Thr His Tyr Ser Ile Arg Ser Thr Leu Arg
2150                2155                2160

Met Glu Leu Met Gly Cys Asp Leu Asn Ser Cys Ser Met Pro Leu
2165                2170                2175

Gly Met Glu Ser Lys Ala Ile Ser Asp Ala Gln Ile Thr Ala Ser
2180                2185                2190

Ser Tyr Phe Thr Asn Met Phe Ala Thr Trp Ser Pro Ser Lys Ala
2195                2200                2205

Arg Leu His Leu Gln Gly Arg Ser Asn Ala Trp Arg Pro Gln Val
2210                2215                2220

Asn Asn Pro Lys Glu Trp Leu Gln Val Asp Phe Gln Lys Thr Met
2225                2230                2235

Lys Val Thr Gly Val Thr Thr Gln Gly Val Lys Ser Leu Leu Thr
2240                2245                2250

Ser Met Tyr Val Lys Glu Phe Leu Ile Ser Ser Ser Gln Asp Gly
2255                2260                2265

His Gln Trp Thr Leu Phe Phe Gln Asn Gly Lys Val Lys Val Phe
2270                2275                2280

Gln Gly Asn Gln Asp Ser Phe Thr Pro Val Val Asn Ser Leu Asp
2285                2290                2295

Pro Pro Leu Leu Thr Arg Tyr Leu Arg Ile His Pro Gln Ser Trp
2300                2305                2310

Val His Gln Ile Ala Leu Arg Met Glu Val Leu Gly Cys Glu Ala
2315                2320                2325

Gln Asp Leu Tyr
2330

<210> SEQ ID NO 14
<211> LENGTH: 2114
<212> TYPE: PRT
<213> ORGANISM: Sus scrofa

<400> SEQUENCE: 14

Ala Ile Arg Arg Tyr Tyr Leu Gly Ala Val Glu Leu Ser Trp Asp Tyr
1               5                   10                  15

Arg Gln Ser Glu Leu Leu Arg Glu Leu His Val Asp Thr Arg Phe Pro
            20                  25                  30

Ala Thr Ala Pro Gly Ala Leu Pro Leu Gly Pro Ser Val Leu Tyr Lys

-continued

```
            35                  40                  45
Lys Thr Val Phe Val Glu Phe Thr Asp Gln Leu Phe Ser Val Ala Arg
 50                  55                  60
Pro Arg Pro Pro Trp Met Gly Leu Leu Gly Pro Thr Ile Gln Ala Glu
 65                  70                  75                  80
Val Tyr Asp Thr Val Val Thr Leu Lys Asn Met Ala Ser His Pro
                     85                  90                  95
Val Ser Leu His Ala Val Gly Val Ser Phe Trp Lys Ser Ser Glu Gly
                100                 105                 110
Ala Glu Tyr Glu Asp His Thr Ser Gln Arg Glu Lys Glu Asp Asp Lys
            115                 120                 125
Val Leu Pro Gly Lys Ser Gln Thr Tyr Val Trp Gln Val Leu Lys Glu
130                 135                 140
Asn Gly Pro Thr Ala Ser Asp Pro Pro Cys Leu Thr Tyr Ser Tyr Leu
145                 150                 155                 160
Ser His Val Asp Leu Val Lys Asp Leu Asn Ser Gly Leu Ile Gly Ala
                165                 170                 175
Leu Leu Val Cys Arg Glu Gly Ser Leu Thr Arg Glu Arg Thr Gln Asn
                180                 185                 190
Leu His Glu Phe Val Leu Leu Phe Ala Val Phe Asp Glu Gly Lys Ser
            195                 200                 205
Trp His Ser Ala Arg Asn Asp Ser Trp Thr Arg Ala Met Asp Pro Ala
            210                 215                 220
Pro Ala Arg Ala Gln Pro Ala Met His Thr Val Asn Gly Tyr Val Asn
225                 230                 235                 240
Arg Ser Leu Pro Gly Leu Ile Gly Cys His Lys Lys Ser Val Tyr Trp
                245                 250                 255
His Val Ile Gly Met Gly Thr Ser Pro Glu Val His Ser Ile Phe Leu
                260                 265                 270
Glu Gly His Thr Phe Leu Val Arg His His Arg Gln Ala Ser Leu Glu
            275                 280                 285
Ile Ser Pro Leu Thr Phe Leu Thr Ala Gln Thr Phe Leu Met Asp Leu
            290                 295                 300
Gly Gln Phe Leu Leu Phe Cys His Ile Ser Ser His His His Gly Gly
305                 310                 315                 320
Met Glu Ala His Val Arg Val Glu Ser Cys Ala Glu Glu Pro Gln Leu
                325                 330                 335
Arg Arg Lys Ala Asp Glu Glu Asp Tyr Asp Asp Asn Leu Tyr Asp
            340                 345                 350
Ser Asp Met Asp Val Val Arg Leu Asp Gly Asp Asp Val Ser Pro Phe
            355                 360                 365
Ile Gln Ile Arg Ser Val Ala Lys Lys His Pro Lys Thr Trp Val His
            370                 375                 380
Tyr Ile Ser Ala Glu Glu Glu Asp Trp Asp Tyr Ala Pro Ala Val Pro
385                 390                 395                 400
Ser Pro Ser Asp Arg Ser Tyr Lys Ser Leu Tyr Leu Asn Ser Gly Pro
                405                 410                 415
Gln Arg Ile Gly Arg Lys Tyr Lys Lys Ala Arg Phe Val Ala Tyr Thr
                420                 425                 430
Asp Val Thr Phe Lys Thr Arg Lys Ala Ile Pro Tyr Glu Ser Gly Ile
            435                 440                 445
Leu Gly Pro Leu Leu Tyr Gly Glu Val Gly Asp Thr Leu Leu Ile Ile
450                 455                 460
```

```
Phe Lys Asn Lys Ala Ser Arg Pro Tyr Asn Ile Tyr Pro His Gly Ile
465                 470                 475                 480

Thr Asp Val Ser Ala Leu His Pro Gly Arg Leu Leu Lys Gly Trp Lys
                485                 490                 495

His Leu Lys Asp Met Pro Ile Leu Pro Gly Glu Thr Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Ile Asn Leu Glu Lys Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Met Met Ser Asp Lys Arg Asn Val Ile Leu Phe
                565                 570                 575

Ser Val Phe Asp Glu Asn Gln Ser Trp Tyr Leu Ala Glu Asn Ile Gln
            580                 585                 590

Arg Phe Leu Pro Asn Pro Asp Gly Leu Gln Pro Gln Asp Pro Glu Phe
        595                 600                 605

Gln Ala Ser Asn Ile Met His Ser Ile Asn Gly Tyr Val Phe Asp Ser
610                 615                 620

Leu Gln Leu Ser Val Cys Leu His Glu Val Ala Tyr Trp Tyr Ile Leu
625                 630                 635                 640

Ser Val Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Val Leu Gly Cys His Asn Ser Asp Leu Arg Asn Arg Gly Met Thr Ala
690                 695                 700

Leu Leu Lys Val Tyr Ser Cys Asp Arg Asp Ile Gly Asp Tyr Tyr Asp
705                 710                 715                 720

Asn Thr Tyr Glu Asp Ile Pro Gly Phe Leu Leu Ser Gly Lys Asn Val
                725                 730                 735

Ile Glu Pro Arg Ser Phe Ala Gln Asn Ser Arg Pro Pro Ser Ala Ser
            740                 745                 750

Gln Lys Gln Phe Gln Thr Ile Thr Ser Pro Glu Asp Val Glu Leu
        755                 760                 765

Asp Pro Gln Ser Gly Glu Arg Thr Gln Ala Leu Glu Glu Leu Ser Val
    770                 775                 780

Pro Ser Gly Asp Gly Ser Met Leu Leu Gly Gln Asn Pro Ala Pro His
785                 790                 795                 800

Gly Ser Ser Ser Asp Leu Gln Glu Ala Arg Asn Glu Ala Asp Asp
                805                 810                 815

Tyr Leu Pro Gly Ala Arg Glu Arg Asn Thr Ala Pro Ser Ala Ala Ala
            820                 825                 830

Arg Leu Arg Pro Glu Leu His His Ser Ala Glu Arg Val Leu Thr Pro
        835                 840                 845

Glu Pro Glu Lys Glu Leu Lys Lys Leu Asp Ser Lys Met Ser Ser Ser
    850                 855                 860

Ser Asp Leu Leu Lys Thr Ser Pro Thr Ile Pro Ser Asp Thr Leu Ser
865                 870                 875                 880
```

```
Ala Glu Thr Glu Arg Thr His Ser Leu Gly Pro Pro His Pro Gln Val
            885                 890                 895

Asn Phe Arg Ser Gln Leu Gly Ala Ile Val Leu Gly Lys Asn Ser Ser
        900                 905                 910

His Phe Ile Gly Ala Gly Val Pro Leu Gly Ser Thr Glu Glu Asp His
        915                 920                 925

Glu Ser Ser Leu Gly Glu Asn Val Ser Pro Val Glu Ser Asp Gly Ile
        930                 935                 940

Phe Glu Lys Glu Arg Ala His Gly Pro Ala Ser Leu Thr Lys Asp Asp
945                 950                 955                 960

Val Leu Phe Lys Val Asn Ile Ser Leu Val Lys Thr Asn Lys Ala Arg
            965                 970                 975

Val Tyr Leu Lys Thr Asn Arg Lys Ile His Ile Asp Asp Ala Ala Leu
            980                 985                 990

Leu Thr Glu Asn Arg Ala Ser Ala Thr Phe Met Asp Lys Asn Thr Thr
            995                 1000                1005

Ala Ser Gly Leu Asn His Val Ser Asn Trp Ile Lys Gly Pro Leu
    1010                1015                1020

Gly Lys Asn Pro Leu Ser Ser Glu Arg Gly Pro Ser Pro Glu Leu
    1025                1030                1035

Leu Thr Ser Ser Gly Ser Gly Lys Ser Val Lys Gly Gln Ser Ser
    1040                1045                1050

Gly Gln Gly Arg Ile Arg Val Ala Val Glu Glu Glu Leu Ser
    1055                1060                1065

Lys Gly Lys Glu Met Met Leu Pro Asn Ser Glu Leu Thr Phe Leu
    1070                1075                1080

Thr Asn Ser Ala Asp Val Gln Gly Asn Asp Thr His Ser Gln Gly
    1085                1090                1095

Lys Lys Ser Arg Glu Glu Met Glu Arg Arg Glu Lys Leu Val Gln
    1100                1105                1110

Glu Lys Val Asp Leu Pro Gln Val Tyr Thr Ala Thr Gly Thr Lys
    1115                1120                1125

Asn Phe Leu Arg Asn Ile Phe His Gln Ser Thr Glu Pro Ser Val
    1130                1135                1140

Glu Gly Phe Asp Gly Gly Ser His Ala Pro Val Pro Gln Asp Ser
    1145                1150                1155

Arg Ser Leu Asn Asp Ser Ala Glu Arg Ala Glu Thr His Ile Ala
    1160                1165                1170

His Phe Ser Ala Ile Arg Glu Glu Ala Pro Leu Glu Ala Pro Gly
    1175                1180                1185

Asn Arg Thr Gly Pro Gly Pro Arg Ser Ala Val Pro Arg Arg Val
    1190                1195                1200

Lys Gln Ser Leu Lys Gln Ile Arg Leu Pro Leu Glu Glu Ile Lys
    1205                1210                1215

Pro Glu Arg Gly Val Val Leu Asn Ala Thr Ser Thr Arg Trp Ser
    1220                1225                1230

Glu Ser Ser Pro Ile Leu Gln Gly Ala Lys Arg Asn Asn Leu Ser
    1235                1240                1245

Leu Pro Phe Leu Thr Leu Glu Met Ala Gly Gly Gln Gly Lys Ile
    1250                1255                1260

Ser Ala Leu Gly Lys Ser Ala Ala Gly Pro Leu Ala Ser Gly Lys
    1265                1270                1275

Leu Glu Lys Ala Val Leu Ser Ser Ala Gly Leu Ser Glu Ala Ser
```

```
                1280                1285                1290
Gly Lys Ala Glu Phe Leu Pro Lys Val Arg Val His Arg Glu Asp
    1295                1300                1305
Leu Leu Pro Gln Lys Thr Ser Asn Val Ser Cys Ala His Gly Asp
    1310                1315                1320
Leu Gly Gln Glu Ile Phe Leu Gln Lys Thr Arg Gly Pro Val Asn
    1325                1330                1335
Leu Asn Lys Val Asn Arg Pro Gly Arg Thr Pro Ser Lys Leu Leu
    1340                1345                1350
Gly Pro Pro Met Pro Lys Glu Trp Glu Ser Leu Glu Lys Ser Pro
    1355                1360                1365
Lys Ser Thr Ala Leu Arg Thr Lys Asp Ile Ile Ser Leu Pro Leu
    1370                1375                1380
Asp Arg His Glu Ser Asn His Ser Ile Ala Ala Lys Asn Glu Gly
    1385                1390                1395
Gln Ala Glu Thr Gln Arg Glu Ala Ala Trp Thr Lys Gln Gly Gly
    1400                1405                1410
Pro Gly Arg Leu Cys Ala Pro Lys Pro Pro Val Leu Arg Arg His
    1415                1420                1425
Gln Arg Asp Ile Ser Leu Pro Thr Phe Gln Pro Glu Glu Asp Lys
    1430                1435                1440
Met Asp Tyr Asp Asp Ile Phe Ser Thr Glu Thr Lys Gly Glu Asp
    1445                1450                1455
Phe Asp Ile Tyr Gly Glu Asp Glu Asn Gln Asp Pro Arg Ser Phe
    1460                1465                1470
Gln Lys Arg Thr Arg His Tyr Phe Ile Ala Ala Val Glu Gln Leu
    1475                1480                1485
Trp Asp Tyr Gly Met Ser Glu Ser Pro Arg Ala Leu Arg Asn Arg
    1490                1495                1500
Ala Gln Asn Gly Glu Val Pro Arg Phe Lys Lys Val Val Phe Arg
    1505                1510                1515
Glu Phe Ala Asp Gly Ser Phe Thr Gln Pro Ser Tyr Arg Gly Glu
    1520                1525                1530
Leu Asn Lys His Leu Gly Leu Leu Gly Pro Tyr Ile Arg Ala Glu
    1535                1540                1545
Val Glu Asp Asn Ile Met Val Thr Phe Lys Asn Gln Ala Ser Arg
    1550                1555                1560
Pro Tyr Ser Phe Tyr Ser Ser Leu Ile Ser Tyr Pro Asp Asp Gln
    1565                1570                1575
Glu Gln Gly Ala Glu Pro Arg His Asn Phe Val Gln Pro Asn Glu
    1580                1585                1590
Thr Arg Thr Tyr Phe Trp Lys Val Gln His His Met Ala Pro Thr
    1595                1600                1605
Glu Asp Glu Phe Asp Cys Lys Ala Trp Ala Tyr Phe Ser Asp Val
    1610                1615                1620
Asp Leu Glu Lys Asp Val His Ser Gly Leu Ile Gly Pro Leu Leu
    1625                1630                1635
Ile Cys Arg Ala Asn Thr Leu Asn Ala Ala His Gly Arg Gln Val
    1640                1645                1650
Thr Val Gln Glu Phe Ala Leu Phe Phe Thr Ile Phe Asp Glu Thr
    1655                1660                1665
Lys Ser Trp Tyr Phe Thr Glu Asn Val Glu Arg Asn Cys Arg Ala
    1670                1675                1680
```

```
Pro Cys His Leu Gln Met Glu Asp Pro Thr Leu Lys Glu Asn Tyr
    1685                1690                1695

Arg Phe His Ala Ile Asn Gly Tyr Val Met Asp Thr Leu Pro Gly
    1700                1705                1710

Leu Val Met Ala Gln Asn Gln Arg Ile Arg Trp Tyr Leu Leu Ser
    1715                1720                1725

Met Gly Ser Asn Glu Asn Ile His Ser Ile His Phe Ser Gly His
    1730                1735                1740

Val Phe Ser Val Arg Lys Lys Glu Glu Tyr Lys Met Ala Val Tyr
    1745                1750                1755

Asn Leu Tyr Pro Gly Val Phe Glu Thr Val Glu Met Leu Pro Ser
    1760                1765                1770

Lys Val Gly Ile Trp Arg Ile Glu Cys Leu Ile Gly Glu His Leu
    1775                1780                1785

Gln Ala Gly Met Ser Thr Thr Phe Leu Val Tyr Ser Lys Glu Cys
    1790                1795                1800

Gln Ala Pro Leu Gly Met Ala Ser Gly Arg Ile Arg Asp Phe Gln
    1805                1810                1815

Ile Thr Ala Ser Gly Gln Tyr Gly Gln Trp Ala Pro Lys Leu Ala
    1820                1825                1830

Arg Leu His Tyr Ser Gly Ser Ile Asn Ala Trp Ser Thr Lys Asp
    1835                1840                1845

Pro His Ser Trp Ile Lys Val Asp Leu Leu Ala Pro Met Ile Ile
    1850                1855                1860

His Gly Ile Met Thr Gln Gly Ala Arg Gln Lys Phe Ser Ser Leu
    1865                1870                1875

Tyr Ile Ser Gln Phe Ile Ile Met Tyr Ser Leu Asp Gly Arg Asn
    1880                1885                1890

Trp Gln Ser Tyr Arg Gly Asn Ser Thr Gly Thr Leu Met Val Phe
    1895                1900                1905

Phe Gly Asn Val Asp Ala Ser Gly Ile Lys His Asn Ile Phe Asn
    1910                1915                1920

Pro Pro Ile Val Ala Arg Tyr Ile Arg Leu His Pro Thr His Tyr
    1925                1930                1935

Ser Ile Arg Ser Thr Leu Arg Met Glu Leu Met Gly Cys Asp Leu
    1940                1945                1950

Asn Ser Cys Ser Met Pro Leu Gly Met Gln Asn Lys Ala Ile Ser
    1955                1960                1965

Asp Ser Gln Ile Thr Ala Ser Ser His Leu Ser Asn Ile Phe Ala
    1970                1975                1980

Thr Trp Ser Pro Ser Gln Ala Arg Leu His Leu Gln Gly Arg Thr
    1985                1990                1995

Asn Ala Trp Arg Pro Arg Val Ser Ser Ala Glu Glu Trp Leu Gln
    2000                2005                2010

Val Asp Leu Gln Lys Thr Val Lys Val Thr Gly Ile Thr Thr Gln
    2015                2020                2025

Gly Val Lys Ser Leu Leu Ser Ser Met Tyr Val Lys Glu Phe Leu
    2030                2035                2040

Val Ser Ser Ser Gln Asp Gly Arg Arg Trp Thr Leu Phe Leu Gln
    2045                2050                2055

Asp Gly His Thr Lys Val Phe Gln Gly Asn Gln Asp Ser Ser Thr
    2060                2065                2070
```

```
Pro Val Val Asn Ala Leu Asp  Pro Pro Leu Phe Thr  Arg Tyr Leu
    2075              2080                2085

Arg Ile His Pro Thr Ser Trp  Ala Gln His Ile Ala  Leu Arg Leu
    2090              2095                2100

Glu Val Leu Gly Cys Glu Ala  Gln Asp Leu Tyr
    2105              2110

<210> SEQ ID NO 15
<211> LENGTH: 2300
<212> TYPE: PRT
<213> ORGANISM: Mus musculus

<400> SEQUENCE: 15

Ala Ile Arg Arg Tyr Tyr Leu Gly Ala Val Glu Leu Ser Trp Asn Tyr
1               5                   10                  15

Ile Gln Ser Asp Leu Leu Ser Val Leu His Thr Asp Ser Arg Phe Leu
            20                  25                  30

Pro Arg Met Ser Thr Ser Phe Pro Phe Asn Thr Ser Ile Met Tyr Lys
        35                  40                  45

Lys Thr Val Phe Val Glu Tyr Lys Asp Gln Leu Phe Asn Ile Ala Lys
    50                  55                  60

Pro Arg Pro Pro Trp Met Gly Leu Leu Gly Pro Thr Ile Trp Thr Glu
65                  70                  75                  80

Val His Asp Thr Val Ile Thr Leu Lys Asn Met Ala Ser His Pro
                85                  90                  95

Val Ser Leu His Ala Val Gly Val Ser Tyr Trp Lys Ala Ser Glu Gly
            100                 105                 110

Asp Glu Tyr Glu Asp Gln Thr Ser Gln Met Glu Lys Glu Asp Asp Lys
        115                 120                 125

Val Phe Pro Gly Glu Ser His Thr Tyr Val Trp Gln Val Leu Lys Glu
    130                 135                 140

Asn Gly Pro Met Ala Ser Asp Pro Pro Cys Leu Thr Tyr Ser Tyr Met
145                 150                 155                 160

Ser His Val Asp Leu Val Lys Asp Leu Asn Ser Gly Leu Ile Gly Ala
                165                 170                 175

Leu Leu Val Cys Lys Glu Gly Ser Leu Ser Lys Glu Arg Thr Gln Met
            180                 185                 190

Leu Tyr Gln Phe Val Leu Leu Phe Ala Val Phe Asp Glu Gly Lys Ser
        195                 200                 205

Trp His Ser Glu Thr Asn Asp Ser Tyr Thr Gln Ser Met Asp Ser Ala
    210                 215                 220

Ser Ala Arg Asp Trp Pro Lys Met His Thr Val Asn Gly Tyr Val Asn
225                 230                 235                 240

Arg Ser Leu Pro Gly Leu Ile Gly Cys His Arg Lys Ser Val Tyr Trp
                245                 250                 255

His Val Ile Gly Met Gly Thr Thr Pro Glu Ile His Ser Ile Phe Leu
            260                 265                 270

Glu Gly His Thr Phe Phe Val Arg Asn His Arg Gln Ala Ser Leu Glu
        275                 280                 285

Ile Ser Pro Ile Thr Phe Leu Thr Ala Gln Thr Leu Leu Ile Asp Leu
    290                 295                 300

Gly Gln Phe Leu Leu Phe Cys His Ile Ser Ser His Lys His Asp Gly
305                 310                 315                 320

Met Glu Ala Tyr Val Lys Val Asp Ser Cys Pro Glu Glu Ser Gln Trp
                325                 330                 335
```

```
Gln Lys Lys Asn Asn Asn Glu Glu Met Glu Asp Tyr Asp Asp Leu
                340                 345                 350

Tyr Ser Glu Met Asp Met Phe Thr Leu Asp Tyr Asp Ser Pro Phe
            355                 360                 365

Ile Gln Ile Arg Ser Val Ala Lys Lys Tyr Pro Lys Thr Trp Ile His
370                 375                 380

Tyr Ile Ser Ala Glu Glu Asp Trp Asp Tyr Ala Pro Ser Val Pro
385                 390                 395                 400

Thr Ser Asp Asn Gly Ser Tyr Lys Ser Gln Tyr Leu Ser Asn Gly Pro
                405                 410                 415

His Arg Ile Gly Arg Lys Tyr Lys Val Arg Phe Ile Ala Tyr Thr
                420                 425                 430

Asp Glu Thr Phe Lys Thr Arg Glu Thr Ile Gln His Glu Ser Gly Leu
                435                 440                 445

Leu Gly Pro Leu Leu Tyr Gly Glu Val Gly Asp Thr Leu Leu Ile Ile
            450                 455                 460

Phe Lys Asn Gln Ala Ser Arg Pro Tyr Asn Ile Tyr Pro His Gly Ile
465                 470                 475                 480

Thr Asp Val Ser Pro Leu His Ala Arg Arg Leu Pro Arg Gly Ile Lys
                485                 490                 495

His Val Lys Asp Leu Pro Ile His Pro Gly Glu Ile Phe Lys Tyr Lys
                500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Ile Asn Pro Glu Arg Asp Leu Ala
            530                 535                 540

Ser Gly Leu Ile Gly Pro Leu Leu Ile Cys Tyr Lys Glu Ser Val Asp
545                 550                 555                 560

Gln Arg Gly Asn Gln Met Met Ser Asp Lys Arg Asn Val Ile Leu Phe
                565                 570                 575

Ser Ile Phe Asp Glu Asn Gln Ser Trp Tyr Ile Thr Glu Asn Met Gln
            580                 585                 590

Arg Phe Leu Pro Asn Ala Ala Lys Thr Gln Pro Gln Asp Pro Gly Phe
            595                 600                 605

Gln Ala Ser Asn Ile Met His Ser Ile Asn Gly Tyr Val Phe Asp Ser
610                 615                 620

Leu Glu Leu Thr Val Cys Leu His Glu Val Ala Tyr Trp His Ile Leu
625                 630                 635                 640

Ser Val Gly Ala Gln Thr Asp Phe Leu Ser Ile Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
            675                 680                 685

Val Leu Gly Cys His Asn Ser Asp Phe Arg Lys Arg Gly Met Thr Ala
                690                 695                 700

Leu Leu Lys Val Ser Ser Cys Asp Lys Ser Thr Ser Asp Tyr Tyr Glu
705                 710                 715                 720

Glu Ile Tyr Glu Asp Ile Pro Thr Gln Leu Val Asn Glu Asn Asn Val
                725                 730                 735

Ile Asp Pro Arg Ser Phe Phe Gln Asn Thr Asn His Pro Asn Thr Arg
                740                 745                 750
```

-continued

```
Lys Lys Lys Phe Lys Asp Ser Thr Ile Pro Lys Asn Asp Met Glu Lys
            755                 760                 765
Ile Glu Pro Gln Phe Glu Glu Ile Ala Glu Met Leu Lys Val Gln Ser
    770                 775                 780
Val Ser Val Ser Asp Met Leu Met Leu Gly Gln Ser His Pro Thr
785                 790                 795                 800
Pro His Gly Leu Phe Leu Ser Asp Gly Gln Glu Ala Ile Tyr Glu Ala
                805                 810                 815
Ile His Asp Asp His Ser Pro Asn Ala Ile Asp Ser Asn Glu Gly Pro
            820                 825                 830
Ser Lys Val Thr Gln Leu Arg Pro Glu Ser His His Ser Glu Lys Ile
            835                 840                 845
Val Phe Thr Pro Gln Pro Gly Leu Gln Leu Arg Ser Asn Lys Ser Leu
850                 855                 860
Glu Thr Thr Ile Glu Val Lys Trp Lys Lys Leu Gly Leu Gln Val Ser
865                 870                 875                 880
Ser Leu Pro Ser Asn Leu Met Thr Thr Thr Ile Leu Ser Asp Asn Leu
                885                 890                 895
Lys Ala Thr Phe Glu Lys Thr Asp Ser Ser Gly Phe Pro Asp Met Pro
                900                 905                 910
Val His Ser Ser Ser Lys Leu Ser Thr Thr Ala Phe Gly Lys Lys Ala
            915                 920                 925
Tyr Ser Leu Val Gly Ser His Val Pro Leu Asn Ala Ser Glu Glu Asn
    930                 935                 940
Ser Asp Ser Asn Ile Leu Asp Ser Thr Leu Met Tyr Ser Gln Glu Ser
945                 950                 955                 960
Leu Pro Arg Asp Asn Ile Leu Ser Ile Glu Asn Asp Arg Leu Leu Arg
            965                 970                 975
Glu Lys Arg Phe His Gly Ile Ala Leu Leu Thr Lys Asp Asn Thr Leu
            980                 985                 990
Phe Lys Asp Asn Val Ser Leu Met Lys Thr Asn Lys Thr Tyr Asn His
            995                 1000                1005
Ser Thr Thr Asn Glu Lys Leu His Thr Glu Ser Pro Thr Ser Ile
    1010                1015                1020
Glu Asn Ser Thr Thr Asp Leu Gln Asp Ala Ile Leu Lys Val Asn
    1025                1030                1035
Ser Glu Ile Gln Glu Val Thr Ala Leu Ile His Asp Gly Thr Leu
    1040                1045                1050
Leu Gly Lys Asn Ser Thr Tyr Leu Arg Leu Asn His Met Leu Asn
    1055                1060                1065
Arg Thr Thr Ser Thr Lys Asn Lys Asp Ile Phe His Arg Lys Asp
    1070                1075                1080
Glu Asp Pro Ile Pro Gln Asp Glu Asn Thr Ile Met Pro Phe
    1085                1090                1095
Ser Lys Met Leu Phe Leu Ser Glu Ser Ser Asn Trp Phe Lys Lys
    1100                1105                1110
Thr Asn Gly Asn Asn Ser Leu Asn Ser Glu Gln Glu His Ser Pro
    1115                1120                1125
Lys Gln Leu Val Tyr Leu Met Phe Lys Lys Tyr Val Lys Asn Gln
    1130                1135                1140
Ser Phe Leu Ser Glu Lys Asn Lys Val Thr Val Glu Gln Asp Gly
    1145                1150                1155
Phe Thr Lys Asn Ile Gly Leu Lys Asp Met Ala Phe Pro His Asn
```

-continued

```
            1160                1165                1170

Met Ser Ile Phe Leu Thr Thr Leu Ser Asn Val His Glu Asn Gly
            1175                1180                1185

Arg His Asn Gln Glu Lys Asn Ile Gln Glu Glu Ile Glu Lys Glu
            1190                1195                1200

Ala Leu Ile Glu Glu Lys Val Val Leu Pro Gln Val His Glu Ala
            1205                1210                1215

Thr Gly Ser Lys Asn Phe Leu Lys Asp Ile Leu Ile Leu Gly Thr
            1220                1225                1230

Arg Gln Asn Ile Ser Leu Tyr Glu Val His Val Pro Val Leu Gln
            1235                1240                1245

Asn Ile Thr Ser Ile Asn Asn Ser Thr Asn Thr Val Gln Ile His
            1250                1255                1260

Met Glu His Phe Phe Lys Arg Arg Lys Asp Lys Glu Thr Asn Ser
            1265                1270                1275

Glu Gly Leu Val Asn Lys Thr Arg Glu Met Val Lys Asn Tyr Pro
            1280                1285                1290

Ser Gln Lys Asn Ile Thr Thr Gln Arg Ser Lys Arg Ala Leu Gly
            1295                1300                1305

Gln Phe Arg Leu Ser Thr Gln Trp Leu Lys Thr Ile Asn Cys Ser
            1310                1315                1320

Thr Gln Cys Ile Ile Lys Ser Gln Ile Asp His Ser Lys Glu Met Lys
            1325                1330                1335

Lys Phe Ile Thr Lys Ser Ser Leu Ser Asp Ser Ser Val Ile Lys
            1340                1345                1350

Ser Thr Thr Gln Thr Asn Ser Ser Asp Ser His Ile Val Lys Thr
            1355                1360                1365

Ser Ala Phe Pro Pro Ile Asp Leu Lys Arg Ser Pro Phe Gln Asn
            1370                1375                1380

Lys Phe Ser His Val Gln Ala Ser Ser Tyr Ile Tyr Asp Phe Lys
            1385                1390                1395

Thr Lys Ser Ser Arg Ile Gln Glu Ser Asn Asn Phe Leu Lys Glu
            1400                1405                1410

Thr Lys Ile Asn Asn Pro Ser Leu Ala Ile Leu Pro Trp Asn Met
            1415                1420                1425

Phe Ile Asp Gln Gly Lys Phe Thr Ser Pro Gly Lys Ser Asn Thr
            1430                1435                1440

Asn Ser Val Thr Tyr Lys Lys Arg Glu Asn Ile Ile Phe Leu Lys
            1445                1450                1455

Pro Thr Leu Pro Glu Glu Ser Gly Lys Ile Glu Leu Leu Pro Gln
            1460                1465                1470

Val Ser Ile Gln Glu Glu Ile Leu Pro Thr Glu Thr Ser His
            1475                1480                1485

Gly Ser Pro Gly His Leu Asn Leu Met Lys Glu Val Phe Leu Gln
            1490                1495                1500

Lys Ile Gln Gly Pro Thr Lys Trp Asn Lys Ala Lys Arg His Gly
            1505                1510                1515

Glu Ser Ile Lys Gly Lys Thr Glu Ser Ser Lys Asn Thr Arg Ser
            1520                1525                1530

Lys Leu Leu Asn His His Ala Trp Asp Tyr His Tyr Ala Ala Gln
            1535                1540                1545

Ile Pro Lys Asp Met Trp Lys Ser Lys Glu Lys Ser Pro Glu Ile
            1550                1555                1560
```

-continued

```
Ile Ser Ile Lys Gln Glu Asp Thr Ile Leu Ser Leu Arg Pro His
    1565                1570                1575

Gly Asn Ser His Ser Ile Gly Ala Asn Glu Lys Gln Asn Trp Pro
    1580                1585                1590

Gln Arg Glu Thr Thr Trp Val Lys Gln Gly Gln Thr Gln Arg Thr
    1595                1600                1605

Cys Ser Gln Ile Pro Pro Val Leu Lys Arg His Gln Arg Glu Leu
    1610                1615                1620

Ser Ala Phe Gln Ser Glu Gln Glu Ala Thr Asp Tyr Asp Asp Ala
    1625                1630                1635

Ile Thr Ile Glu Thr Ile Glu Asp Phe Asp Ile Tyr Ser Glu Asp
    1640                1645                1650

Ile Lys Gln Gly Pro Arg Ser Phe Gln Gln Lys Thr Arg His Tyr
    1655                1660                1665

Phe Ile Ala Ala Val Glu Arg Leu Trp Asp Tyr Gly Met Ser Thr
    1670                1675                1680

Ser His Val Leu Arg Asn Arg Tyr Gln Ser Asp Asn Val Pro Gln
    1685                1690                1695

Phe Lys Lys Val Val Phe Gln Glu Phe Thr Asp Gly Ser Phe Ser
    1700                1705                1710

Gln Pro Leu Tyr Arg Gly Glu Leu Asn Glu His Leu Gly Leu Leu
    1715                1720                1725

Gly Pro Tyr Ile Arg Ala Glu Val Glu Asp Asn Ile Met Val Thr
    1730                1735                1740

Phe Lys Asn Gln Ala Ser Arg Pro Tyr Ser Phe Tyr Ser Ser Leu
    1745                1750                1755

Ile Ser Tyr Lys Glu Asp Gln Arg Gly Glu Glu Pro Arg Arg Asn
    1760                1765                1770

Phe Val Lys Pro Asn Glu Thr Lys Ile Tyr Phe Trp Lys Val Gln
    1775                1780                1785

His His Met Ala Pro Thr Glu Asp Glu Phe Asp Cys Lys Ala Trp
    1790                1795                1800

Ala Tyr Phe Ser Asp Val Asp Leu Glu Arg Asp Met His Ser Gly
    1805                1810                1815

Leu Ile Gly Pro Leu Leu Ile Cys His Ala Asn Thr Leu Asn Pro
    1820                1825                1830

Ala His Gly Arg Gln Val Ser Val Gln Glu Phe Ala Leu Leu Phe
    1835                1840                1845

Thr Ile Phe Asp Glu Thr Lys Ser Trp Tyr Phe Thr Glu Asn Val
    1850                1855                1860

Lys Arg Asn Cys Lys Thr Pro Cys Asn Phe Gln Met Glu Asp Pro
    1865                1870                1875

Thr Leu Lys Glu Asn Tyr Arg Phe His Ala Ile Asn Gly Tyr Val
    1880                1885                1890

Met Asp Thr Leu Pro Gly Leu Val Met Ala Gln Asp Gln Arg Ile
    1895                1900                1905

Arg Trp Tyr Leu Leu Ser Met Gly Asn Asn Glu Asn Ile Gln Ser
    1910                1915                1920

Ile His Phe Ser Gly His Val Phe Thr Val Arg Lys Lys Glu Glu
    1925                1930                1935

Tyr Lys Met Ala Val Tyr Asn Leu Tyr Pro Gly Val Phe Glu Thr
    1940                1945                1950
```

```
Leu Glu Met Ile Pro Ser Arg Ala Gly Ile Trp Arg Val Glu Cys
    1955                1960                1965

Leu Ile Gly Glu His Leu Gln Ala Gly Met Ser Thr Leu Phe Leu
    1970                1975                1980

Val Tyr Ser Lys Gln Cys Gln Ile Pro Leu Gly Met Ala Ser Gly
    1985                1990                1995

Ser Ile Arg Asp Phe Gln Ile Thr Ala Ser Gly His Tyr Gly Gln
    2000                2005                2010

Trp Ala Pro Asn Leu Ala Arg Leu His Tyr Ser Gly Ser Ile Asn
    2015                2020                2025

Ala Trp Ser Thr Lys Glu Pro Phe Ser Trp Ile Lys Val Asp Leu
    2030                2035                2040

Leu Ala Pro Met Ile Val His Gly Ile Lys Thr Gln Gly Ala Arg
    2045                2050                2055

Gln Lys Phe Ser Ser Leu Tyr Ile Ser Gln Phe Ile Ile Met Tyr
    2060                2065                2070

Ser Leu Asp Gly Lys Lys Trp Leu Ser Tyr Gln Gly Asn Ser Thr
    2075                2080                2085

Gly Thr Leu Met Val Phe Phe Gly Asn Val Asp Ser Ser Gly Ile
    2090                2095                2100

Lys His Asn Ser Phe Asn Pro Pro Ile Ile Ala Arg Tyr Ile Arg
    2105                2110                2115

Leu His Pro Thr His Ser Ser Ile Arg Ser Thr Leu Arg Met Glu
    2120                2125                2130

Leu Met Gly Cys Asp Leu Asn Ser Cys Ser Ile Pro Leu Gly Met
    2135                2140                2145

Glu Ser Lys Val Ile Ser Asp Thr Gln Ile Thr Ala Ser Ser Tyr
    2150                2155                2160

Phe Thr Asn Met Phe Ala Thr Trp Ser Pro Ser Gln Ala Arg Leu
    2165                2170                2175

His Leu Gln Gly Arg Thr Asn Ala Trp Arg Pro Gln Val Asn Asp
    2180                2185                2190

Pro Lys Gln Trp Leu Gln Val Asp Leu Gln Lys Thr Met Lys Val
    2195                2200                2205

Thr Gly Ile Ile Thr Gln Gly Val Lys Ser Leu Phe Thr Ser Met
    2210                2215                2220

Phe Val Lys Glu Phe Leu Ile Ser Ser Ser Gln Asp Gly His His
    2225                2230                2235

Trp Thr Gln Ile Leu Tyr Asn Gly Lys Val Lys Val Phe Gln Gly
    2240                2245                2250

Asn Gln Asp Ser Ser Thr Pro Met Met Asn Ser Leu Asp Pro Pro
    2255                2260                2265

Leu Leu Thr Arg Tyr Leu Arg Ile His Pro Gln Ile Trp Glu His
    2270                2275                2280

Gln Ile Ala Leu Arg Leu Glu Ile Leu Gly Cys Glu Ala Gln Gln
    2285                2290                2295

Gln Tyr
    2300

<210> SEQ ID NO 16
<211> LENGTH: 2324
<212> TYPE: PRT
<213> ORGANISM: Canis familiaris

<400> SEQUENCE: 16
```

```
Ala Thr Arg Lys Tyr Tyr Leu Gly Ala Val Glu Leu Ser Trp Asp Tyr
1               5                   10                  15

Met Gln Ser Asp Leu Leu Ser Ala Leu His Ala Asp Thr Ser Phe Ser
            20                  25                  30

Ser Arg Val Pro Gly Ser Leu Pro Leu Thr Thr Ser Val Thr Tyr Arg
        35                  40                  45

Lys Thr Val Phe Val Glu Phe Thr Asp Asp Leu Phe Asn Ile Ala Lys
    50                  55                  60

Pro Arg Pro Pro Trp Met Gly Leu Leu Gly Pro Thr Ile Gln Ala Glu
65                  70                  75                  80

Val Tyr Asp Thr Val Val Ile Val Leu Lys Asn Met Ala Ser His Pro
                85                  90                  95

Val Ser Leu His Ala Val Gly Val Ser Tyr Trp Lys Ala Ser Glu Gly
                100                 105                 110

Ala Glu Tyr Glu Asp Gln Thr Ser Gln Lys Glu Lys Glu Asp Asp Asn
            115                 120                 125

Val Ile Pro Gly Glu Ser His Thr Tyr Val Trp Gln Val Leu Lys Glu
        130                 135                 140

Asn Gly Pro Met Ala Ser Asp Pro Pro Cys Leu Thr Tyr Ser Tyr Phe
145                 150                 155                 160

Ser His Val Asp Leu Val Lys Asp Leu Asn Ser Gly Leu Ile Gly Ala
                165                 170                 175

Leu Leu Val Cys Lys Glu Gly Ser Leu Ala Lys Glu Arg Thr Gln Thr
                180                 185                 190

Leu Gln Glu Phe Val Leu Leu Phe Ala Val Phe Asp Glu Gly Lys Ser
            195                 200                 205

Trp His Ser Glu Thr Asn Ala Ser Leu Thr Gln Ala Glu Ala Gln His
210                 215                 220

Glu Leu His Thr Ile Asn Gly Tyr Val Asn Arg Ser Leu Pro Gly Leu
225                 230                 235                 240

Thr Val Cys His Lys Arg Ser Val Tyr Trp His Val Ile Gly Met Gly
                245                 250                 255

Thr Thr Pro Glu Val His Ser Ile Phe Leu Glu Gly His Thr Phe Leu
                260                 265                 270

Val Arg Asn His Arg Gln Ala Ser Leu Glu Ile Ser Pro Ile Thr Phe
                275                 280                 285

Leu Thr Ala Gln Thr Phe Leu Met Asp Leu Gly Gln Phe Leu Leu Phe
                290                 295                 300

Cys His Ile Pro Ser His Gln His Asp Gly Met Glu Ala Tyr Val Lys
305                 310                 315                 320

Val Asp Ser Cys Pro Glu Glu Pro Gln Leu Arg Met Lys Asn Asn Glu
                325                 330                 335

Asp Lys Asp Tyr Asp Asp Gly Leu Tyr Asp Ser Asp Met Asp Val Val
            340                 345                 350

Ser Phe Asp Asp Asp Ser Ser Pro Phe Ile Gln Ile Arg Ser Val
            355                 360                 365

Ala Lys Lys His Pro Lys Thr Trp Val His Tyr Ile Ala Ala Glu Glu
    370                 375                 380

Glu Asp Trp Asp Tyr Ala Pro Ser Gly Pro Thr Pro Asn Asp Arg Ser
385                 390                 395                 400

His Lys Asn Leu Tyr Leu Asn Asn Gly Pro Gln Arg Ile Gly Lys Lys
                405                 410                 415
```

-continued

```
Tyr Lys Lys Val Arg Phe Val Ala Tyr Thr Asp Glu Thr Phe Lys Thr
                420                 425                 430

Arg Glu Ala Ile Gln Tyr Glu Ser Gly Ile Leu Gly Pro Leu Leu Tyr
            435                 440                 445

Gly Glu Val Gly Asp Thr Leu Leu Ile Ile Phe Lys Asn Gln Ala Ser
        450                 455                 460

Arg Pro Tyr Asn Ile Tyr Pro His Gly Ile Asn Tyr Val Thr Pro Leu
465                 470                 475                 480

His Thr Gly Arg Leu Pro Lys Gly Val Lys His Leu Lys Asp Met Pro
                485                 490                 495

Ile Leu Pro Gly Glu Ile Phe Lys Tyr Lys Trp Thr Val Thr Val Glu
            500                 505                 510

Asp Gly Pro Thr Lys Ser Asp Pro Arg Cys Leu Thr Arg Tyr Tyr Ser
        515                 520                 525

Ser Phe Ile Asn Leu Glu Arg Asp Leu Ala Ser Gly Leu Ile Gly Pro
530                 535                 540

Leu Leu Ile Cys Tyr Lys Glu Ser Val Asp Gln Arg Gly Asn Gln Met
545                 550                 555                 560

Met Ser Asp Lys Arg Asn Val Ile Leu Phe Ser Val Phe Asp Glu Asn
                565                 570                 575

Arg Ser Trp Tyr Leu Thr Glu Asn Met Gln Arg Phe Leu Pro Asn Ala
            580                 585                 590

Asp Val Val Gln Pro His Asp Pro Glu Phe Gln Leu Ser Asn Ile Met
        595                 600                 605

His Ser Ile Asn Gly Tyr Val Phe Asp Asn Leu Gln Leu Ser Val Cys
610                 615                 620

Leu His Glu Val Ala Tyr Trp Tyr Ile Leu Ser Val Gly Ala Gln Thr
625                 630                 635                 640

Asp Phe Leu Ser Val Phe Phe Ser Gly Tyr Thr Phe Lys His Lys Met
                645                 650                 655

Val Tyr Glu Asp Thr Leu Thr Leu Phe Pro Phe Ser Gly Glu Thr Val
            660                 665                 670

Phe Met Ser Met Glu Asn Pro Gly Leu Trp Val Leu Gly Cys His Asn
        675                 680                 685

Ser Asp Phe Arg Asn Arg Gly Met Thr Ala Leu Leu Lys Val Ser Ser
690                 695                 700

Cys Asn Arg Asn Ile Asp Asp Tyr Tyr Glu Asp Thr Tyr Glu Asp Ile
705                 710                 715                 720

Pro Thr Pro Leu Leu Asn Glu Asn Asn Val Ile Lys Pro Arg Ser Phe
                725                 730                 735

Ser Gln Asn Ser Arg His Pro Ser Thr Lys Glu Lys Gln Leu Lys Ala
            740                 745                 750

Thr Thr Thr Pro Glu Asn Asp Ile Glu Lys Ile Asp Leu Gln Ser Gly
        755                 760                 765

Glu Arg Thr Gln Leu Ile Lys Ala Gln Ser Val Ser Ser Ser Asp Leu
770                 775                 780

Leu Met Leu Leu Gly Gln Asn Pro Thr Pro Arg Gly Leu Phe Leu Ser
785                 790                 795                 800

Asp Leu Arg Glu Ala Thr Asp Arg Ala Asp His Ser Arg Gly Ala
                805                 810                 815

Ile Glu Arg Asn Lys Gly Pro Pro Glu Val Ala Ser Leu Arg Pro Glu
            820                 825                 830

Leu Arg His Ser Glu Asp Arg Glu Phe Thr Pro Glu Pro Glu Leu Gln
```

-continued

```
              835                 840                 845
Leu Arg Leu Asn Glu Asn Leu Gly Thr Asn Thr Thr Val Glu Leu Lys
    850                 855                 860
Lys Leu Asp Leu Lys Ile Ser Ser Ser Asp Ser Leu Met Thr Ser
865                 870                 875                 880
Pro Thr Ile Pro Ser Asp Lys Leu Ala Ala Thr Glu Lys Thr Gly
                885                 890                 895
Ser Leu Gly Pro Pro Asn Met Ser Val His Phe Asn Ser His Leu Gly
                900                 905                 910
Thr Ile Val Phe Gly Asn Asn Ser Ser His Leu Ile Gln Ser Gly Val
            915                 920                 925
Pro Leu Glu Leu Ser Glu Glu Asp Asn Asp Ser Lys Leu Leu Glu Ala
930                 935                 940
Pro Leu Met Asn Ile Gln Glu Ser Ser Leu Arg Glu Asn Val Leu Ser
945                 950                 955                 960
Met Glu Ser Asn Arg Leu Phe Lys Glu Glu Arg Ile Arg Gly Pro Ala
                965                 970                 975
Ser Leu Ile Lys Asp Asn Ala Leu Phe Lys Val Asn Ile Ser Ser Val
                980                 985                 990
Lys Thr Asn Arg Ala Pro Val Asn Leu Thr Thr Asn Arg Lys Thr Arg
            995                 1000                1005
Val Ala Ile Pro Thr Leu Leu Ile Glu Asn Ser Thr Ser Val Trp
    1010                1015                1020
Gln Asp Ile Met Leu Glu Arg Asn Thr Glu Phe Lys Glu Val Thr
    1025                1030                1035
Ser Leu Ile His Asn Glu Thr Phe Met Asp Arg Asn Thr Thr Ala
    1040                1045                1050
Leu Gly Leu Asn His Val Ser Asn Lys Thr Thr Leu Ser Lys Asn
    1055                1060                1065
Val Glu Met Ala His Gln Lys Lys Glu Asp Pro Val Pro Leu Arg
    1070                1075                1080
Ala Glu Asn Pro Asp Leu Ser Ser Ser Lys Ile Pro Phe Leu Pro
    1085                1090                1095
Asp Trp Ile Lys Thr His Gly Lys Asn Ser Leu Ser Ser Glu Gln
    1100                1105                1110
Arg Pro Ser Pro Lys Gln Leu Thr Ser Leu Gly Ser Glu Lys Ser
    1115                1120                1125
Val Lys Asp Gln Asn Phe Leu Ser Glu Glu Lys Val Val Val Gly
    1130                1135                1140
Glu Asp Glu Phe Thr Lys Asp Thr Glu Leu Gln Glu Ile Phe Pro
    1145                1150                1155
Asn Asn Lys Ser Ile Phe Phe Ala Asn Leu Ala Asn Val Gln Glu
    1160                1165                1170
Asn Asp Thr Tyr Asn Gln Glu Lys Lys Ser Pro Glu Glu Ile Glu
    1175                1180                1185
Arg Lys Glu Lys Leu Thr Gln Glu Asn Val Ala Leu Pro Gln Ala
    1190                1195                1200
His Thr Met Ile Gly Thr Lys Asn Phe Leu Lys Asn Leu Phe Leu
    1205                1210                1215
Leu Ser Thr Lys Gln Asn Val Ala Gly Leu Glu Glu Gln Pro Tyr
    1220                1225                1230
Thr Pro Ile Leu Gln Asp Thr Arg Ser Leu Asn Asp Ser Pro His
    1235                1240                1245
```

```
Ser Glu Gly Ile His Met Ala Asn Phe Ser Lys Ile Arg Glu Glu
    1250                1255                1260

Ala Asn Leu Glu Gly Leu Gly Asn Gln Thr Asn Gln Met Val Glu
    1265                1270                1275

Arg Phe Pro Ser Thr Thr Arg Met Ser Ser Asn Ala Ser Gln His
    1280                1285                1290

Val Ile Thr Gln Arg Gly Lys Arg Ser Leu Lys Gln Pro Arg Leu
    1295                1300                1305

Ser Gln Gly Glu Ile Lys Phe Glu Arg Lys Val Ile Ala Asn Asp
    1310                1315                1320

Thr Ser Thr Gln Trp Ser Lys Asn Met Asn Tyr Leu Ala Gln Gly
    1325                1330                1335

Thr Leu Thr Gln Ile Glu Tyr Asn Glu Lys Glu Lys Arg Ala Ile
    1340                1345                1350

Thr Gln Ser Pro Leu Ser Asp Cys Ser Met Arg Asn His Val Thr
    1355                1360                1365

Ile Gln Met Asn Asp Ser Ala Leu Pro Val Ala Lys Glu Ser Ala
    1370                1375                1380

Ser Pro Ser Val Arg His Thr Asp Leu Thr Lys Ile Pro Ser Gln
    1385                1390                1395

His Asn Ser Ser His Leu Pro Ala Ser Ala Cys Asn Tyr Thr Phe
    1400                1405                1410

Arg Glu Arg Thr Ser Gly Val Gln Glu Gly Ser His Phe Leu Gln
    1415                1420                1425

Glu Ala Lys Arg Asn Asn Leu Ser Leu Ala Phe Val Thr Leu Gly
    1430                1435                1440

Ile Thr Glu Gly Gln Gly Lys Phe Ser Ser Leu Gly Lys Ser Ala
    1445                1450                1455

Thr Asn Gln Pro Met Tyr Lys Lys Leu Glu Asn Thr Val Leu Leu
    1460                1465                1470

Gln Pro Gly Leu Ser Glu Thr Ser Asp Lys Val Glu Leu Leu Ser
    1475                1480                1485

Gln Val His Val Asp Gln Glu Asp Ser Phe Pro Thr Lys Thr Ser
    1490                1495                1500

Asn Asp Ser Pro Gly His Leu Asp Leu Met Gly Lys Ile Phe Leu
    1505                1510                1515

Gln Lys Thr Gln Gly Pro Val Lys Met Asn Lys Thr Asn Ser Pro
    1520                1525                1530

Gly Lys Val Pro Phe Leu Lys Trp Ala Thr Glu Ser Ser Glu Lys
    1535                1540                1545

Ile Pro Ser Lys Leu Leu Gly Val Leu Ala Trp Asp Asn His Tyr
    1550                1555                1560

Asp Thr Gln Ile Pro Ser Glu Glu Trp Lys Ser Gln Lys Lys Ser
    1565                1570                1575

Gln Thr Asn Thr Ala Phe Lys Arg Lys Asp Thr Ile Leu Pro Leu
    1580                1585                1590

Gly Pro Cys Glu Asn Asn Asp Ser Thr Ala Ala Ile Asn Glu Gly
    1595                1600                1605

Gln Asp Lys Pro Gln Arg Glu Ala Met Trp Ala Lys Gln Gly Glu
    1610                1615                1620

Pro Gly Arg Leu Cys Ser Gln Asn Pro Pro Val Ser Lys His His
    1625                1630                1635
```

-continued

```
Gln Arg Glu Ile Thr Val Thr Thr Leu Gln Pro Glu Glu Asp Lys
1640                1645                1650

Phe Glu Tyr Asp Asp Thr Phe Ser Ile Glu Met Lys Arg Glu Asp
1655                1660                1665

Phe Asp Ile Tyr Gly Asp Tyr Glu Asn Gln Gly Leu Arg Ser Phe
1670                1675                1680

Gln Lys Lys Thr Arg His Tyr Phe Ile Ala Ala Val Glu Arg Leu
1685                1690                1695

Trp Asp Tyr Gly Met Ser Arg Ser Pro His Ile Leu Arg Asn Arg
1700                1705                1710

Ala Gln Ser Gly Asp Val Gln Gln Phe Lys Lys Val Val Phe Gln
1715                1720                1725

Glu Phe Thr Asp Gly Ser Phe Thr Gln Pro Leu Tyr Arg Gly Glu
1730                1735                1740

Leu Asn Glu His Leu Gly Leu Leu Gly Pro Tyr Ile Arg Ala Glu
1745                1750                1755

Val Glu Asp Asn Ile Val Val Thr Phe Lys Asn Gln Ala Ser Arg
1760                1765                1770

Pro Tyr Ser Phe Tyr Ser Ser Leu Ile Ser Tyr Asp Glu Asp Glu
1775                1780                1785

Gly Gln Gly Ala Glu Pro Arg Arg Lys Phe Val Asn Pro Asn Glu
1790                1795                1800

Thr Lys Ile Tyr Phe Trp Lys Val Gln His His Met Ala Pro Thr
1805                1810                1815

Lys Asp Glu Phe Asp Cys Lys Ala Trp Ala Tyr Phe Ser Asp Val
1820                1825                1830

Asp Leu Glu Lys Asp Val His Ser Gly Leu Ile Gly Pro Leu Leu
1835                1840                1845

Ile Cys Arg Ser Asn Thr Leu Asn Pro Ala His Gly Arg Gln Val
1850                1855                1860

Thr Val Gln Glu Phe Ala Leu Val Phe Thr Ile Phe Asp Glu Thr
1865                1870                1875

Lys Ser Trp Tyr Phe Thr Glu Asn Leu Glu Arg Asn Cys Arg Ala
1880                1885                1890

Pro Cys Asn Val Gln Lys Glu Asp Pro Thr Leu Lys Glu Asn Phe
1895                1900                1905

Arg Phe His Ala Ile Asn Gly Tyr Val Lys Asp Thr Leu Pro Gly
1910                1915                1920

Leu Val Met Ala Gln Asp Gln Lys Val Arg Trp Tyr Leu Leu Ser
1925                1930                1935

Met Gly Ser Asn Glu Asn Ile His Ser Ile His Phe Ser Gly His
1940                1945                1950

Val Phe Thr Val Arg Lys Lys Glu Glu Tyr Lys Met Ala Val Tyr
1955                1960                1965

Asn Leu Tyr Pro Gly Val Phe Glu Thr Val Glu Met Leu Pro Ser
1970                1975                1980

Gln Val Gly Ile Trp Arg Ile Glu Cys Leu Ile Gly Glu His Leu
1985                1990                1995

Gln Ala Gly Met Ser Thr Leu Phe Leu Val Tyr Ser Lys Lys Cys
2000                2005                2010

Gln Thr Pro Leu Gly Met Ala Ser Gly His Ile Arg Asp Phe Gln
2015                2020                2025

Ile Thr Ala Ser Gly Gln Tyr Gly Gln Trp Ala Pro Lys Leu Ala
```

|      |      |      |      | 2030 |      |      |      | 2035 |      |      |      | 2040 |
|------|------|------|------|------|------|------|------|------|------|------|------|------|
| Arg  | Leu  | His  | Tyr  | Ser  | Gly  | Ser  | Ile  | Asn  | Ala  | Trp  | Ser  | Thr  | Lys  | Asp  |
|      |      |      |      | 2045 |      |      |      | 2050 |      |      |      | 2055 |
| Pro  | Phe  | Ser  | Trp  | Ile  | Lys  | Val  | Asp  | Leu  | Leu  | Ala  | Pro  | Met  | Ile  | Ile  |
|      |      |      |      | 2060 |      |      |      | 2065 |      |      |      | 2070 |
| His  | Gly  | Ile  | Met  | Thr  | Gln  | Gly  | Ala  | Arg  | Gln  | Lys  | Phe  | Ser  | Ser  | Leu  |
|      |      |      |      | 2075 |      |      |      | 2080 |      |      |      | 2085 |
| Tyr  | Val  | Ser  | Gln  | Phe  | Ile  | Ile  | Met  | Tyr  | Ser  | Leu  | Asp  | Gly  | Asn  | Lys  |
|      |      |      |      | 2090 |      |      |      | 2095 |      |      |      | 2100 |
| Trp  | His  | Ser  | Tyr  | Arg  | Gly  | Asn  | Ser  | Thr  | Gly  | Thr  | Leu  | Met  | Val  | Phe  |
|      |      |      |      | 2105 |      |      |      | 2110 |      |      |      | 2115 |
| Phe  | Gly  | Asn  | Val  | Asp  | Ser  | Ser  | Gly  | Ile  | Lys  | His  | Asn  | Ile  | Phe  | Asn  |
|      |      |      |      | 2120 |      |      |      | 2125 |      |      |      | 2130 |
| Pro  | Pro  | Ile  | Ile  | Ala  | Gln  | Tyr  | Ile  | Arg  | Leu  | His  | Pro  | Thr  | His  | Tyr  |
|      |      |      |      | 2135 |      |      |      | 2140 |      |      |      | 2145 |
| Ser  | Ile  | Arg  | Ser  | Thr  | Leu  | Arg  | Met  | Glu  | Leu  | Leu  | Gly  | Cys  | Asp  | Phe  |
|      |      |      |      | 2150 |      |      |      | 2155 |      |      |      | 2160 |
| Asn  | Ser  | Cys  | Ser  | Met  | Pro  | Leu  | Gly  | Met  | Glu  | Ser  | Lys  | Ala  | Ile  | Ser  |
|      |      |      |      | 2165 |      |      |      | 2170 |      |      |      | 2175 |
| Asp  | Ala  | Gln  | Ile  | Thr  | Ala  | Ser  | Ser  | Tyr  | Leu  | Ser  | Ser  | Met  | Leu  | Ala  |
|      |      |      |      | 2180 |      |      |      | 2185 |      |      |      | 2190 |
| Thr  | Trp  | Ser  | Pro  | Ser  | Gln  | Ala  | Arg  | Leu  | His  | Leu  | Gln  | Gly  | Arg  | Thr  |
|      |      |      |      | 2195 |      |      |      | 2200 |      |      |      | 2205 |
| Asn  | Ala  | Trp  | Arg  | Pro  | Gln  | Ala  | Asn  | Asn  | Pro  | Lys  | Glu  | Trp  | Leu  | Gln  |
|      |      |      |      | 2210 |      |      |      | 2215 |      |      |      | 2220 |
| Val  | Asp  | Phe  | Arg  | Lys  | Thr  | Met  | Lys  | Val  | Thr  | Gly  | Ile  | Thr  | Thr  | Gln  |
|      |      |      |      | 2225 |      |      |      | 2230 |      |      |      | 2235 |
| Gly  | Val  | Lys  | Ser  | Leu  | Leu  | Ile  | Ser  | Met  | Tyr  | Val  | Lys  | Glu  | Phe  | Leu  |
|      |      |      |      | 2240 |      |      |      | 2245 |      |      |      | 2250 |
| Ile  | Ser  | Ser  | Ser  | Gln  | Asp  | Gly  | His  | Asn  | Trp  | Thr  | Leu  | Phe  | Leu  | Gln  |
|      |      |      |      | 2255 |      |      |      | 2260 |      |      |      | 2265 |
| Asn  | Gly  | Lys  | Val  | Lys  | Val  | Phe  | Gln  | Gly  | Asn  | Arg  | Asp  | Ser  | Ser  | Thr  |
|      |      |      |      | 2270 |      |      |      | 2275 |      |      |      | 2280 |
| Pro  | Val  | Arg  | Asn  | Arg  | Leu  | Glu  | Pro  | Pro  | Leu  | Val  | Ala  | Arg  | Tyr  | Val  |
|      |      |      |      | 2285 |      |      |      | 2290 |      |      |      | 2295 |
| Arg  | Leu  | His  | Pro  | Gln  | Ser  | Trp  | Ala  | His  | His  | Ile  | Ala  | Leu  | Arg  | Leu  |
|      |      |      |      | 2300 |      |      |      | 2305 |      |      |      | 2310 |
| Glu  | Val  | Leu  | Gly  | Cys  | Asp  | Thr  | Gln  | Gln  | Pro  | Ala  |      |      |      |      |
|      |      |      |      | 2315 |      |      |      | 2320 |      |      |      |      |

VARIANT OF ANTIHEMOPHILIC FACTOR VIII HAVING INCREASED SPECIFIC ACTIVITY

CROSS-REFERENCE TO RELATED APPLICATIONS AND INCORPORATION BY REFERENCE

This application is a divisional of U.S. patent application Ser. No. 13/883,244, filed Jul. 23, 2013, which is the U.S national phase pursuant to 35 U.S.C. § 371 of International Application No. PCT/US2011/059297, filed Nov. 4, 2011, which claims priority to U.S. Provisional Patent Application No. 61/410,437, filed Nov. 5, 2010, the disclosures of which are incorporated herein in their entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: ASCII (text) file named 008073_5144_US01_Sequence_Listing; Size 173 KB; Created: Jan. 15, 2018.

FIELD OF THE INVENTION

The present invention is in the field of blood coagulation factors and hemophilia. It relates to a new variant of antihemophilic factor VIII (FVIII), designated herein rFVIIIv3, having an increased specific activity in comparison to known factor VIII products.

BACKGROUND OF THE INVENTION

Blood clotting begins when platelets adhere to the cut wall of an injured blood vessel at a lesion site. Subsequently, in a cascade of enzymatically regulated reactions, soluble fibrinogen molecules are converted by the enzyme thrombin to insoluble strands of fibrin that hold the platelets together in a thrombus. At each step in the cascade, a variant precursor is converted to a protease that cleaves the next variant precursor in the series. Cofactors are required at most of the steps.

Factor VIII (also called antihemophilic factor VIII or FVIII) circulates as an inactive precursor in blood, bound tightly and non-covalently to von Willebrand factor. Factor VIII is proteolytically activated by thrombin or factor Xa, which dissociates it from von Willebrand factor and activates its procoagulant function in the cascade. In its active form, the variant factor VIIIa is a cofactor that increases the catalytic efficiency of factor IXa toward factor X activation by several orders of magnitude.

Cloning of human FVIII has revealed that the variant contains 2332 amino acids organized within a number of domains with the sequence A1-A2-B-A3-C1-C2 (Vehar et al., 1984, Nature 312, 337-342; Toole et al., 1984, Nature 312, 342-347 and Wood et al., 1984, Nature 312, 330-337). Most of FVIII is heterodimeric in plasma, containing a light-chain and various heavy-chain derivatives. The heterodimeric structure is due to proteolytic cleavage of the precursor at arginine$^{1648}$, resulting in heavy- and light-chains comprising $A_1$-$A_2$-B and $A_3$-$C_1$-$C_2$, respectively. The heterogeneity within the heavy chain is explained by limited proteolysis within its carboxy-terminal B-domain.

In order to function as a co-factor for factor X activation, FVIII requires limited proteolysis by factor Xa or thrombin. This activation involves cleavage at arginine at positions 372 and 740 on the heavy-chain and at position 1689 on the light-chain. It has been established that in comparison with the inactive precursor, active FVIII cofactor lacks a light chain fragment 1649-1689 and the whole B-domain (Mertens et al., 1993).

People with deficiencies in factor VIII or antibodies against factor VIII who are not treated with factor VIII suffer uncontrolled internal bleeding that may cause a range of serious symptoms, from inflammatory reactions in joints to early death. Severe hemophiliacs, who number about 10,000 in the United States, can be treated with infusion of human factor VIII, which will restore the blood's normal clotting ability if administered with sufficient frequency and concentration. The classic definition of factor VIII, in fact, is the substance present in normal blood plasma that corrects the clotting defect in plasma derived from individuals with hemophilia A.

Several preparations of human plasma-derived factor VIII of varying degrees of purity are available commercially for the treatment of hemophilia A. These include a partially purified factor VIII derived from the pooled blood of many donors that is heat- and detergent treated for viruses but contain a significant level of antigenic variants; a monoclonal antibody purified factor VIII that has lower levels of antigenic impurities and viral contamination; and recombinant human factor VIII.

The development of antibodies ("inhibitors" or "inhibitory antibodies") that inhibit the activity of factor VIII is a serious complication in the management of patients with hemophilia.

Alloantibodies develop in approximately 20% of patients with hemophilia A in response to therapeutic infusions of factor VIII. In previously untreated patients with hemophilia A who develop inhibitors, the inhibitor usually develops within one year of treatment. Additionally, antibodies (autoantibodies) that inactivate factor VIII occasionally develop in individuals with previously normal factor VIII levels. If the inhibitor titer is low enough, patients can be managed by increasing the dose of factor VIII. However, often the inhibitor titer is so high that it cannot be overwhelmed by factor VIII. An alternative strategy is to bypass the need for factor VIII during normal hemostasis using activated prothrombin complex concentrate preparations (for example, KONYNE (Cutter Laboratories), FEIBA (Baxter Healthcare), PROPLEX (Baxter Healthcare)) or recombinant human factor VIIa. Additionally, since porcine factor VIII usually has substantially less reactivity with inhibitors than human factor VIII, a partially purified porcine factor VIII preparation (HYATE: C (IPSEN Pharma)) has been used. Many patients who have developed inhibitory antibodies to human factor VIII have been successfully treated with porcine factor VIII and have tolerated such treatment for long periods of time.

However, public health concerns regarding the risk of viruses or other blood-borne contaminants have limited the usefulness of porcine factor VIII purified from porcine blood. A recombinant porcine factor VIII variant has therefore been developed, which is designated "OBI-1" and described e.g. in WO 01/68109. OBI-1 is a partially B-domain deleted porcine FVIII. This molecule is presently in clinical development.

B-domain deleted factor VIII variants are known to keep the procoagulant and cofactor activity of factor VIII. In addition to this, Mertens et al. (British Journal of Haematology 1993, 85, 133-142) describe recombinant human factor VIII variants lacking the B-domain and the heavy-chain sequence spanning from Lysine 713 to Arginine 740.

Many hemophiliacs require daily replacement of factor VIII to prevent bleeding and the resulting deforming hemophilic arthropathy. In view of this, there is a need for a more potent factor VIII molecule.

SUMMARY OF THE INVENTION

In a first aspect, the invention relates to an isolated, recombinant, fully or partially B-domain deleted factor VIII (FVIII) variant, the FVIII variant being devoid of an up to 27 amino acid sequence corresponding to amino acids 716 to 742 of porcine factor VIII as depicted in FIG. 2 or amino acids 714 to 740 of SEQ ID NO: 7. This 27 amino acid sequence, NTGDYYEDSYEDISAYLLSKNNAIEPR (SEQ ID NO:10), may be partially or completely deleted.

In one embodiment, the invention relates to an isolated, recombinant, fully or partially B-domain deleted FVIII variant, the FVIII variant being devoid of an up to 27 amino acid sequence corresponding to amino acids 716 to 742 of porcine factor VIII as depicted in FIG. 2 or amino acids 714 to 740 of SEQ ID NO: 7, where 27, 26, 25, 24, 23, 22, 21, 20, 19, 18, 17, 16, 15, 14, 13, 12, 11, 10, 9, 8, 7, 6, 5, 4, 3, 2 or 1 amino acids may be deleted. In another embodiment, 27, 26, 25, 24, 23, 22, 21 or 20 amino acids are deleted. In another embodiment, 27, 26, or 25 amino acids are deleted. In another embodiment, the 27 amino acids corresponding to DIGDYYDNTYEDIPGFLLSGKNVIEPR (SEQ ID NO:10) are deleted.

In one embodiment, the invention relates to an isolated, recombinant, fully or partially B-domain deleted FVIII variant, the FVIII variant being devoid of an up to 27 amino acid sequence corresponding to amino acids 716 to 742 of human factor VIII as depicted in FIG. 2 or amino acids 714 to 740 of SEQ ID NO: 8, where 27, 26, 25, 24, 23, 22, 21, 20, 19, 18, 17, 16, 15, 14, 13, 12, 11, 10, 9, 8, 7, 6, 5, 4, 3, 2 or 1 amino acids may be deleted. In another embodiment, 27, 26, 25, 24, 23, 22, 21 or 20 amino acids are deleted. In another embodiment, 27, 26, or 25 amino acids are deleted. In another embodiment, the 27 amino acids corresponding to NTGDYYEDSYEDISAYLLSKNNAIEPR (SEQ ID NO:11) are deleted.

In another embodiment, the invention relates to an isolated, recombinant, fully or partially B-domain deleted porcine FVIII variant being completely devoid of the 27 amino acids corresponding to DIGDYYDNTYEDIPGFLLSGKNVIEPR (SEQ ID NO:10).

In another embodiment, the invention relates to an isolated, recombinant, fully or partially B-domain deleted human FVIII variant being completely devoid of the 27 amino acids corresponding to NTGDYYEDSYEDISAYLLSKNNAIEPR (SEQ ID NO:11).

In another embodiment, the invention relates to an isolated, recombinant, fully or partially B-domain deleted canine FVIII variant being completely devoid of the 27 amino acids corresponding to NIDDYYEDTYEDIPTPLLNENNVIKPR (SEQ ID NO:12).

A second aspect of the invention relates to a polynucleotide encoding a polypeptide as defined in the first aspect and the embodiments described.

In a third aspect, the invention relates to an expression vector comprising a polynucleotide as defined in the second aspect.

A fourth aspect of the invention relates to a mammalian cell comprising an expression vector as defined in the third aspect.

In a fifth aspect, the invention relates to a method for producing a FVIII as defined in the first aspect, comprising the steps of:
  a. Culturing a mammalian cell according to the fourth aspect; and
  b. Isolating from the mammalian cell the FVIII variant.

A sixth aspect of the invention relates to a pharmaceutical composition comprising a FVIII variant as defined in the first aspect.

In a seventh aspect, the invention relates to a method of treating a patient suffering from hemophilia comprising administering a therapeutically effective amount of FVIII variant according to the first aspect of the invention to a patient in need thereof, thereby treating the hemophilia in said patient.

In an eighth aspect, the invention relates to a FVIII variant according to the first aspect for use in treating hemophilia.

BRIEF DESCRIPTION OF THE DRAWINGS

FIG. 2 a-e are continuations of the same sequence. FIG. 2a-e shows a sequence alignment between the factor VIII sequences from human (*homo sapiens*), pig (*sus scrofa*), mouse (*mus musculus*) and dog (*canis familiaris*). This sequence alignment is taken from HADB (aka HAMSTeRS) 2010, home page of the Haemophilia A Mutation Database and a resource site for work on factor VIII (hadb.org.uk). The numbering follows the human sequence and is not identical to the amino acid numbers of the sequences in the Sequence Listing. The bold plus double underlined sequence depicts the sequence missing in the recombinant FVIIIv3 variants of the invention. The underlined sequence is the sequence of the B-domain. The sequence highlighted in grey is the portion from the B-domain which can be retained in the partially B-domain deleted FIIIv3 sequences of the invention.

BRIEF DESCRIPTION OF THE SEQUENCES

Figure 1:
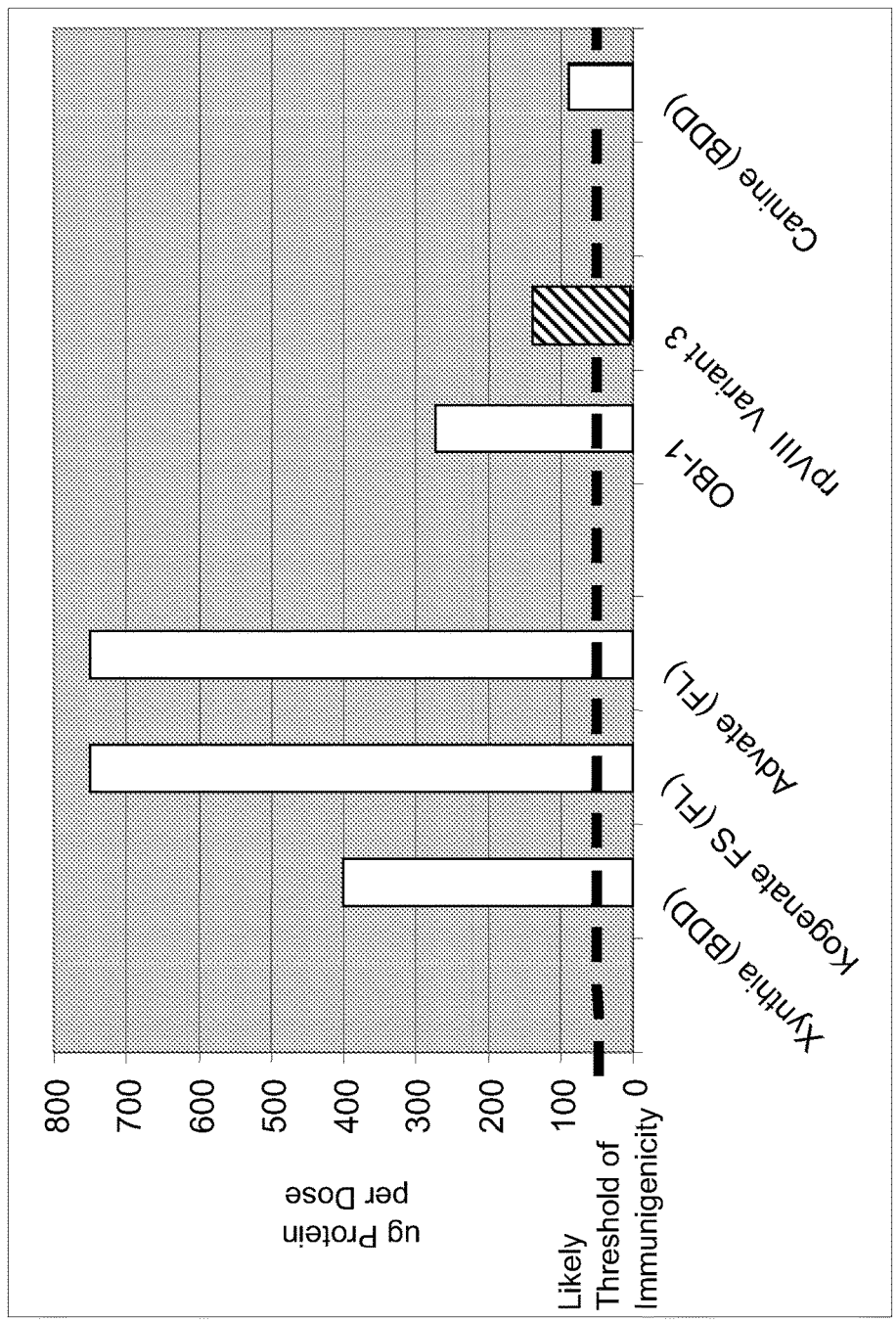
FIG. 1 shows the amount of protein in μg per dose required for 5 known FVIII products (blank columns) and the new rpFVIIIv3 (hashed column). BDD=B-domain deleted; FL=full length; u=μ.

SEQ ID NO: 1 shows the sequence of porcine partially B-domain deleted FVIIIv3;
SEQ ID NO: 2 shows the sequence of a human B-domain deleted FVIIIv3;
SEQ ID NO: 3 shows the sequence of a canine B-domain deleted FVIIIv3;
SEQ ID NO: 4 shows the sequence from the porcine FVIII B-domain that can be present in a partially B-domain deleted FVIII molecule of the invention (the so called "B-domain linker");
SEQ ID NO: 5 shows a B-domain linker sequence from the human FVIII B-domain that can be present in a partially B-domain deleted FVIII molecule of the invention;
SEQ ID NO: 6 shows a B-domain linker sequence from the canine FVIII B-domain that can be present in a partially B-domain deleted FVIII molecule of the invention;
SEQ ID NO: 7 shows the amino acid sequence of full-length porcine FVIII;
SEQ ID NO: 8 shows the amino acid sequence of full-length human FVIII;

SEQ ID NO: 9 shows the amino acid sequence of full-length canine FVIII;

SEQ ID NO:10 shows the 27 peptide sequence which corresponds to amino acids 716 to 742 of porcine factor VIII as depicted in FIG. 2 or amino acids 714 to 740 of SEQ ID NO: 7;

SEQ ID NO:11 shows the 27 peptide sequence which corresponds to amino acids 714 to 740 of human factor VIII as depicted in FIG. 2 or amino acids 714 to 740 of SEQ ID NO: 8; and SEQ ID NO:12 shows the 27 peptide sequence which corresponds to amino acids 714 to 740 of canine factor VIII as depicted in FIG. 2 or amino acids 708 to 734 of SEQ ID NO: 9.

DETAILED DESCRIPTION OF THE INVENTION

The invention is based on the finding of a variant of a partially B-domain deleted recombinant porcine factor VIII protein which contains a particular 27 amino acid deletion. This variant, which is herein designated rpFVIIIv3, has been shown to have an increased specific activity as compared to a similar protein containing the 27 amino acid stretch, namely a partially B-domain deleted recombinant porcine FVIII called "OBI-1". OBI-1, its amino acid sequence and polynucleotides encoding OBI-1 are known e.g. from U.S. Pat. No. 6,458,563.

The invention relates to an isolated, recombinant, fully or partially B-domain deleted factor VIII (FVIII) variant, wherein the FVIII variant is devoid of an amino acid sequence corresponding to amino acids 716 to 742 of porcine factor VIII as depicted in FIG. 2 or amino acids 714 to 740 of SEQ ID NO: 7.

Additionally, the invention relates to an isolated, recombinant, fully or partially B-domain deleted FVIII variant, the FVIII variant being devoid of a 27 amino acid sequence corresponding to amino acids 716 to 742 of porcine factor VIII as depicted in FIG. 2 or amino acids 714 to 740 of SEQ ID NO: 7, where 27, 26, 25, 24, 23, 22, 21, 20, 19, 18, 17, 16, 15, 14, 13, 12, 11, 10, 9, 8, 7, 6, 5, 4, 3, 2 or 1 amino acids may be deleted. In one variant, 27, 26, 25, 24, 23, 22, 21 or 20 amino acids are deleted. In another variant, 27, 26, or 25 amino acids are deleted. In the rpFVIIIv3 variant, the 27 amino acids corresponding to DIGDYYDNTYEDIPGFLLSGKNVIEPR (SEQ ID NO:10) are deleted.

Additionally, the invention relates to an isolated, recombinant, fully or partially B-domain deleted FVIII variant, the FVIII variant being devoid of a 27 amino acid sequence corresponding to amino acids 714 to 740 of human factor VIII as depicted in FIG. 2 or amino acids 714 to 740 of SEQ ID NO: 8, where 27, 26, 25, 24, 23, 22, 21, 20, 19, 18, 17, 16, 15, 14, 13, 12, 11, 10, 9, 8, 7, 6, 5, 4, 3, 2 or 1 amino acids may be deleted. In one variant, 27, 26, 25, 24, 23, 22, 21 or 20 amino acids are deleted. In another variant, 27, 26, or 25 amino acids are deleted. In a human FVIIIv3 variant (rhFVIIIv3), the 27 amino acids corresponding to NTGDYYEDSYEDISAYLLSKNNAIEPR (SEQ ID NO:11) are deleted.

Additionally, the invention relates to an isolated, recombinant, fully or partially B-domain deleted FVIII variant, the FVIII variant being devoid of a 27 amino acid sequence corresponding to amino acids 714 to 740 of canine factor VIII as depicted in FIG. 2 or amino acids 708 to 734 of SEQ ID NO: 9, where 27, 26, 25, 24, 23, 22, 21, 20, 19, 18, 17, 16, 15, 14, 13, 12, 11, 10, 9, 8, 7, 6, 5, 4, 3, 2 or 1 amino acids may be deleted. In one variant, 27, 26, 25, 24, 23, 22, 21 or 20 amino acids are deleted. In another variant, 27, 26, or 25 amino acids are deleted. In a canine FVIIIv3 variant (rcFVIIIv3), the 27 amino acids corresponding to NIDDYYEDTYEDIPTPLLNENNVIKPR (SEQ ID NO:12) are deleted.

Such variants have an elevated specific activity as compared to similar variants containing the intact 27 amino acid sequence. Preferably, the specific activity is increased by more than 25% or 30% or 35% or 40% or 45% or 50% or 55% or 60%.

The term "specific activity," as used herein, refers to the activity that will correct the coagulation defect of human factor VIII deficient plasma. Specific activity is measured in units of clotting activity per milligram total factor VIII variant in a standard assay in which the clotting time of human factor VIII deficient plasma is compared to that of normal human plasma. A suitable standard assay for measuring the potency of FVIII products, which is accepted by the FDA for high purity FVIII concentrates, is called the one-stage clotting assay (OSCA; see Example 5; Langdell R D, Wagner R H, Brinkhous K M., Effect of antihemophilic factor on one-stage clotting tests: a presumptive test for hemophilia and a simple one-stage antihemophilic assay procedure, J Lab Clin Med, 1953; 41:637-47; Brand J T, Measurement of factor VIII: a potential risk factor for vascular disease, Arch Pathol Lab Med, 1993; 117:48-51; Preston F E, Kitchen S, Quality control and factor VIII assays, Haemophilia, 1998; 4:651-3; National Committee for Clinical Laboratory Standards (NCCLS USA). Determination of factor coagulant activities; Approved guideline, NCCLS Document H-48-A 1997; 17:1-36). The amount of FVIII protein present in a sample can be measured e.g. by SEC HPLC (size-exclusion high-performance liquid chromatography).

One unit of factor VIII activity is the activity present in one milliliter of normal human plasma. In the assay, the shorter the time for clot formation, the greater the activity of the factor VIII being assayed. Porcine factor VIII has coagulation activity in a human factor VIII assay.

In line with the present invention, the terms "protein" and "polypeptide" are being used interchangeably.

Being "devoid of an amino acid sequence corresponding to amino acids 716 to 742 as depicted in FIG. 2" means that amino acids 716 and 742, as well as the amino acids between these positions, are deleted, i.e. not included, in the FVIII variant of the invention. This stretch of amino acids consists thus of 27 amino acids, of which the FVIII variants of the invention are devoid.

The factor VIII variants of the invention are herein globally designated "FVIII variant(s)" or "FVIIIv3" or "rFVIIIv3". They can be of porcine, human, canine, murine or any other origin which is appropriate for human or animal therapy. FIG. 2 depicts a sequence alignment of FVIII sequences of human, porcine, murine and canine origin.

The sequence deleted in the FVIII variants of the invention is highlighted in bold and double underlined. This stretch of amino acids can be identified for the FVIII variants of other species by the person skilled in the art by aligning the FVIII sequences of further species with e.g. the porcine or human sequence and taking the amino acids that correspond to amino acids 716 to 742 as per FIG. 2 of the present patent application.

Embodiments of the invention relate to FVIII variants of porcine, human or canine origin.

In an embodiment, the FVIII variant according to the invention comprises the sequence of SEQ ID NO:1, or a variant thereof comprising a sequence being at least 90% identical to SEQ ID NO: 1. It is understood that the 10% variability concerns the sequences outside of the deleted stretch of amino acids, i.e. that the variant is completely devoid of DIGDYYDNTYEDIPGFLLSGKNVIEPR (SEQ ID NO:10), an amino acid sequence corresponding to amino acids 716 to 742 of porcine factor VIII as depicted in FIG. 2 or amino acids 714 to 740 of SEQ ID NO: 7.

In a further embodiment, the FVIII variant of the invention comprises the sequence of SEQ ID NO:2, or a variant thereof comprising a sequence being at least 90% identical to SEQ ID NO: 2. Again, the variant is understood to be completely devoid of an amino acid sequence NTGDYYEDSYEDISAYLLSKNNAIEPR (SEQ ID NO:11), corresponding to amino acids 714 to 740 of human factor VIII as depicted in FIG. 2 or amino acids 714 to 740 of SEQ ID NO: 8.

In yet a further embodiment, the FVIII variant of the invention comprises the sequence of SEQ ID NO:3, or a variant thereof comprising a sequence being at least 90% identical to SEQ ID NO: 3. Again, the variant is understood to be completely devoid of an amino acid sequence NID-DYYEDTYEDIPTPLLNENNVIKPR (SEQ ID NO:12) corresponding to amino acids 714 to 740 of canine factor VIII as depicted in FIG. 2 or amino acids 708 to 734 of SEQ ID NO: 9.

The FVIII variants of the invention can also comprise sequences that are at least 91, 92, 93, 94, 95, 96, 97, 98, 99, 99.5, 99.6, 99.7, 99.8 or 99.9% identical to the sequences of SEQ ID NO: 7, 8 or 9.

To determine the percent identity of two polypeptides/proteins, the amino acid sequences are aligned for optimal comparison purposes (e.g., gaps can be introduced in the sequence of a first amino acid sequence for optimal alignment with a second amino acid sequence). The amino acid residues at corresponding amino acid positions are then compared. When a position in the first sequence is occupied by the same amino acid residue as the corresponding position in the second sequence, then the molecules are identical at that position. The percent identity between the two sequences is a function of the number of identical positions shared by the sequences (i.e., % identity=# of identical positions/total # of positions (e.g., (overlapping positions)× 100).

The determination of percent identity between two sequences can be accomplished using a mathematical algorithm. A preferred, non-limiting example of a mathematical algorithm utilized for the comparison of two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. Such an algorithm is incorporated into the NBLAST and XBLAST programs of Altschul, et al. (1990) J. Mol. Biol. 215:403-410. BLAST nucleotide searches can be performed with the NBLAST program, score=100, wordlength=12 to obtain nucleotide sequences homologous to a nucleic acid molecules of the invention. BLAST variant searches can be performed with the XBLAST program, score=50, wordlength=3 to obtain amino acid sequences homologous to a variant molecules of the invention. To obtain gapped alignments for comparison purposes, Gapped BLAST can be utilized as described in Altschul et al. (1997) Nucleic Acids Res. 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller, (1988) CABIOS 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) Proc. Natl. Acad. Sci. USA 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The FVIII variant of the invention can be partially or fully B-domain deleted. This means that either the whole B-domain is deleted, or a part of the B-domain is retained in the FVIII variant. The remaining (retained) part of the B-domain is e.g. selected from the 20, 15, 12, 10 or 5 N-terminal amino acids and the 20, 15, 12, 10 or 5 C-terminal amino acids of the B-domain, fused in frame with each other.

Hence, preferably, in the partially B-domain deleted FVIII variants of the invention, significant portions of the approximately 900 amino acid B-domain are being removed. In embodiments of the invention, less than 5% or less than 4% or less than 3% or less than 2% or less than 1% of the B-domain remain present in the FVIII variants.

In embodiments of the invention, the remaining portion of the B-domain is selected from a sequence consisting of SEQ ID NO: 4 or SEQ ID NO:5 or SEQ ID NO: 6.

In a further aspect, the invention relates to a polynucleotide encoding a polypeptide/protein as described above. A polynucleotide can be an RNA or DNA molecule whose nucleotide sequence embodies coding information to a host cell for the amino acid sequence of the variant of the invention, according to the known relationships of the genetic code.

In a further aspect, the invention relates to an expression vector comprising a polynucleotide as described above.

An "expression vector" is a DNA element, often of circular structure, having the ability to replicate autonomously in a desired host cell, or to integrate into a host cell genome and also possessing certain well-known features which permit expression of a coding DNA inserted into the vector sequence at the proper site and in proper orientation. Such features can include, but are not limited to, one or more promoter sequences to direct transcription initiation of the coding DNA and other DNA elements such as enhancers, polyadenylation sites and the like, all as well known in the art. The term "expression vector" is used to denote both a vector having a DNA coding sequence to be expressed inserted within its sequence, and a vector having the requisite expression control elements so arranged with respect to an insertion site that it can serve to express any coding DNA inserted into the site, all as well-known in the art. Thus, for example, a vector lacking a promoter can become an expression vector by the insertion of a promoter combined with a coding DNA. An expression vector, as used herein, can also be a viral vector.

Expression of the recombinant FVIII variants of the invention is preferably carried out in mammalian cell culture.

Therefore, in a further aspect, the invention relates to a mammalian cell comprising an expression vector as described above. For instance, CHO (Chinese hamster ovary) cells and BHK cells (baby hamster kidney cells) are mammalian cells that are suitable host cells in the context of the present invention.

In accordance with another aspect of the invention, a method for producing a FVIII variant of the invention comprises the steps of:
  a. Culturing a mammalian cell as described above; and
  b. Isolating from the mammalian cell the FVIII variant.
In an embodiment, the method further comprises the step of
  c. Formulating the factor VIII variant together with appropriate excipients into a pharmaceutical composition.

Excipients suitable for human or animal administration are e.g. pharmaceutical stabilization compounds, preservatives, delivery vehicles, and/or carrier vehicles. One suitable formulation for factor VIII products is e.g. described in WO 03/080108, which is incorporated by reference herein.

In a further aspect, the invention relates to a pharmaceutical composition comprising a FVIII variant of the invention.

A further aspect of the invention relates to a method of treating a patient suffering from factor VIII deficiency comprising administering a therapeutically effective amount of FVIII variant of the invention to a patient in need thereof, thereby treating the factor VIII deficiency in said patient.

The term "therapeutically effective amount" as used herein, means the level of FVIII in the plasma of a patient having FVIII deficiency, who has received a pharmaceutical composition of FVIII variant, that is sufficient to exhibit a measurable improvement or protective effect in the patient (e.g., to stop bleeding). The patients having FVIII deficiency are typically congenital hemophilia A patients but also include those subjects diagnosed with "acquired hemophilia", a condition in which those who are not congenital hemophiliacs spontaneously develop inhibitory antibodies to their FVIII, creating a serious FVIII deficiency.

The invention also relates to a FVIII variant of the invention for use in treating factor VIII deficiency.

Treatment can take the form of a single intravenous administration of the composition or periodic or continuous administration over an extended period of time, as required. Preferably, administration of the FVIII variant is by intravenous route.

"Factor VIII deficiency," as used herein, includes deficiency in clotting activity caused by production of defective factor VIII, by inadequate or no production of factor VIII, or by partial or total inhibition of factor VIII by inhibitors. Hemophilia A is a type of factor VIII deficiency resulting from a defect in an X-linked gene and the absence or deficiency of the factor VIII variant it encodes.

The FVIII variants of the invention are used to treat uncontrolled bleeding due to factor VIII deficiency (e.g., intraarticular, intracranial, or gastrointestinal hemorrhage) in hemophiliacs.

In an embodiment of the invention, the factor VIII deficiency is hemophilia A.

In another embodiment, the factor VIII deficiency is acquired hemophilia.

In the factor VIII deficiency is treated in patients having developed human FVIII antibodies.

As mentioned above, the FVIII variants of the invention have increased specific activity. It is therefore possible to administer reduced amounts of FVIII variant in order to treat VIII deficiency in accordance with the present invention.

The amounts of FVIII variant can be reduced by at least 30%, 35%, 40%, 45%, 50%, 55%, 60% as compared to therapy with a FVIII product that does not contain the up to 27 amino acid deletion of the invention.

Reducing the amount of FVIII variant therapy has the advantage of expected reduced immunogenicity, i.e. it is expected that the probability of generation of inhibitory antibodies against the FVIII replacement therapy in the patient is significantly reduced.

In an embodiment, a factor VIII variant of the invention is administered in an amount of no more than 200 µg/dose or 150 µg/dose or 145 µg/dose or 140 µg/dose or 136 µg/dose or 130 µg/dose.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning a range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EXAMPLES

Example 1

Expression of Recombinant Porcine Partially B-Domain Deleted FVIII (OBI-1) and Isolation of Three Variant Proteins (rpVIIIv1, v2 and v3)

Expression of OBI-1 in BHK cells was carried out essentially as described in U.S. Pat. No. 6,458,563. Three variants were detected in the produced material (rpVIIIv1, v2 and v3). The variants were isolated and purified to >95% purity ion exchange chromatography. For purification, an AKTA Explorer system (AKTA Explorer 10, GE Healthcare Lifesciences #17-5167-01) using a MonoQ HR10/10 semi-preparative anion exchange column (now Mono Q 10/100 GL, GE Healthcare Lifesciences #17-5167-01) was used. Elution was carried out on a gradient with the two following buffers:
Buffer A: 10 mM TRIS, pH 7.0, 0.01% Polysorbate 80
Buffer B: Buffer A and 1 M sodium chloride.

The purification method characteristics are summarized in Table 1.

TABLE 1 rpFVIII Variant Purification Method

| AKTA Method: | LoopMQ1010 |
|---|---|
| Flow: | 4 ml/min |
| Equilibrium Column | 8 CV |
| Load flow | 4 ml/min |
| Sample Volume | 40-1000 ml |
| Wash Column | 10 CV |

| Gradient | Column Volume (CV) | % B |
|---|---|---|
| | 7 | 45 |
| | 4 | 50 |
| | 4 | 50 |
| | 6 | 52 |
| | 4 | 52 |
| | 2 | 55 |
| | 7 | 60 |
| | 1 | 65 |
| | 5 | 65 |
| | 1 | 70 |
| | 5 | 70 |
| | 1 | 100 |
| | 7 | 100 |
| | 1 | 10 |
| | 4 | 10 |
| Total Run | 59 CV | |
| Column Temp | Not controlled | |

Example 2

Variant 3 (rpVIIIv3) has a Significantly Higher Specific Activity than Variants 1 and 2

The specific activity of each variant was assessed by dividing the potency assessed by one stage coagulation assay (OSCA) by the protein concentration as measured by the SEC HPLC per method. The OSCA and SEC HPLC methods were carried out as described in "Materials and Methods" Example 5.

Results

The results for the specific activities are indicated in Table 2.

TABLE 2

Specific Activities (OSCA method) for Purified Variants 1, 2 and 3 obtained from two different lots of rpFVIII

| Sample based on SEC | OSCA units/ml | % RSD* | Specific activity units/ml | % RSD* |
|---|---|---|---|---|
| V1-lot 1 | 1060 | 1.5 | 11956 | 1.7 |
| V2-lot 1 | 715 | 2.7 | 17267 | 3.3 |
| V3-lot 1 | 216 | 1.2 | 25926 | 2.8 |
| OBI-1 | 513 | 1 | 18150 | 1.3 |
| V1-lot 2 | 980 | 1.2 | 12532 | 1.5 |
| V2-lot 2 | 613 | 0.6 | 16089 | 1.3 |
| V3-lot 2 | 280 | 2.9 | 19718 | 4.1 |
| OBI-1 | 565 | 4.0 | 14427 | 4.4 |

*relative standard deviation

The observation of significantly higher specific activity for variant 3 in the OSCA assay is distinct and consistent. Since the OSCA method is predictive and representative for the coagulation process in humans, it is expected that variant 3 is a product of significant value. It is expected that 1.5-2.0 fold increase in potency reduce the amount of FVIII administered to patients and might therefore indirectly reduce the occurrence of immunological side effects.

Example 3

Sequence Determination of rpFVIIIv3

The sequence of purified v3 was determined by peptide map followed by LCMS (liquid chromatography mass spectrometry) and LCMS/MS (liquid chromatography mass spectrometry/mass spectrometry) on a Q-TOF Ultima Mass Spectrometer, running MassLynx 4.0 (Waters Corporation, Milford, Mass.).

Approximately 250 μg of Variant 3 was concentrated using an Amicon, Centricon YM-10 concentrator with a 10,000 MWCO filter (Millipore Corporation, Billerica, Mass.) to a volume of <100 μL. The samples were mixed with 450 μL of 6 M guanidine HCl/0.002 M EDTA (ethylenediaminetetraacetic acid)/0.02 M Tris buffer pH 8 and transferred to 2.0 mL polypropylene tubes. 1 M DTT (dithiothreitol) was added to each sample to a final concentration of 10 mM and incubated for 1 hour at 37° C. After reduction, 2 M iodoacetamide was added to each tube to a final concentration of 20 mM and incubated for an additional hour at room temperature. The reduced and alkylated samples were transferred to dialysis cassettes and dialyzed for 1 hour against 1 L of 50 mM ammonium bicarbonate dialysis buffer containing 1.0 M urea, pH 8. The samples were then dialyzed against 1 L of dialysis buffer overnight at room temperature while maintaining constant stirring. After dialysis the final volumes were approximately 0.5 mL each. Samples were divided into two 125 μg aliquots.

After dialysis, the protein sample was contained in a matrix that is optimal for proteolytic digestion with trypsin. Trypsin was added to each sample at an enzyme to substrate ratio of 1:20 (w:w) and incubated for 8 hours at 37° C. All samples were transferred to HPLC vials and analyzed by HPLC-MS.

Reduced and alkylated protein was injected onto a Vydac C18 reverse phase column (Grace, Deerfield, Ill.). Prior to the sample injection, a blank sample (Mobile Phase A; deionized water containing 0.2% (v:v) formic acid) was analyzed to equilibrate the column and demonstrate the absence of interfering peaks.

Mass spectrometry data was collected on a Q-TOF API-US mass spectrometer or a Q-TOF Ultima mass spectrometer (Waters Corporation, Milford, Mass.) using electrospray ionization (ESI) in the positive ion mode. Prior to sample analysis, the mass spectrometer was calibrated using a 5th order fit on the fragment ions of Glu-Fibrinogen peptide covering a range of 175 to 1285 m/z. For the calibration to pass specifications, a RMS (root mean square) error for the mass of the peptide fragments less than 5 ppm was required. The software package Masslynx 4.0™ SP2 and SP4 (Waters Corporation, Milford, Mass.) were used for data acquisition and analysis.

Both MS and MS/MS data were collected using a single liquid chromatography (LC) run. Full mass spectrometer (MS) survey scans were collected from 200-1950 m/z.

The sequence of rpFVIII was determined to correspond to SEQ ID NO: 1. This sequence contains a 27 amino acid deletion in comparison with the OBI-1 sequence.

Example 4 rpFVIIIv3 has a Higher Specific Activity than Other Known FVIII Products

The specific activity of rpFVIIIv3 was compared to three commercially available FVIII products, namely Xynthia® (a recombinant, B-domain deleted human FVIII from Wyeth Pharmaceuticals (Philadelphia, Pa.)), Kogenate FS® (a full-length human FVIII from Bayer Healthcare (Tarrytown, N.Y.)) and Advate® (a full-length human FVIII from Baxter (Westlake Village, Calif.)), as well as to OBI-1 (a recombinant partially B-domain deleted porcine FVIII), which is presently under clinical development, and a B-domain deleted canine factor VIII (Denise E. Sabatino et. al., Recombinant canine B-domain-deleted FVIII exhibits high specific activity and is safe in the canine hemophilia A model, Blood, 12 Nov. 2009, Vol. 114, No. 20, pp. 4562-4565).

The specific activity of OBI-1 and rpFVIIIv3 was determined by the methods as described in Example 5.

The results are depicted in Table 3 and FIG. 1. Due to its increased specific activities, lower amounts of prVIIIv3 per dose can be administered to a patient. It is expected that this decrease in dose will lead to a reduced immunogenicity, i.e. result in a lower probability that patients develop inhibitory antibodies.

TABLE 3

Specific activities of FVIII products as compared to rpVIIIv3

| | Specific Activity in IU/mg Protein | Amt protein^ pg/dose |
|---|---|---|
| Xynthia | 7500 | 400 |
| Kogenate FS | 4000 | 750 |
| Advate | 4000 | 750 |
| OBI-1 | 11000 | 273 |
| rpVIIIv3 | 22000 | 136 |
| Canine BDD* FVIII | 34000 | 88 |

^Amt Protein = xxxx µg/dose. The numbers shown in the column for rpVIII3 mean that an amount of 136 µg per dose will be required. One dose is the required amount to raise the blood factor VIII level from 0% to 100%, i.e. the higher the specific activity (XXX units/mg), the less amount (in terms of µg) is required. Note that 1 mg = 1000 µg. Given that a typical dose is 3000 units per patient, the amount of actual protein required = 3000/22000 = 0.136 mg = 136 µg.
*BDD stands for B-domain deleted and FL stands for full length In conclusion, these results show that rpVIIIv3 has a significantly higher specific activity than the tested products that are presently commercialized, or under clinical development, for FVIII replacement therapy.

In particular, it is highly surprising a deletion of 27 amino acids, present in rpVIIIv3 but not in OBI-1, leads to a 50% increase in specific activity (as measured by the OSCA assay).

Example 5

Materials and Methods

One-Stage Coagulation Assay—OSCA—Method
1. Dilute Reference Standard in Assay Buffer (10% Factor VIII deficient plasma+Owren's Veronal Buffer, per liter, 28 mmol of sodium barbital and 125 mmol of NaCl, pH 7.35) to target potency of 1.0 units/mL.
2. Dilute check standards, activity controls and samples in Assay Buffer to the target potency.
3. Load the calibration standard (reference) and reagents into the appropriate wells inside a Symex instrument. (Sysmex CA-1500, Coagulation Analyzer, Dade Behring # B4260-1500 (Siemans Corporation, Deerfield, Ill.)).
4. Load check standard, controls and samples into racks outside of the Sysmex instrument.
5. Assay sequence occurs automatically inside the instrument as follows:
    a. 5 uL of sample is diluted into 45 ul of assay buffer inside the reaction tube
    b. 50 ul of factor VIII deficient plasma is added to the reaction tube
    c. 50 ul of Dade Actin FS (purified soy phosphatides in $1.0 \times 10^{-4}$M Ellagic acid activator, Dade Behring, Liederbach, Germany) activated partial thromboplastin time reagent is added to the reaction tube and incubated for 60 seconds.
    d. 50 ul of Calcium Chloride (0.025M, Dade Behring, Liederbach, Germany) is added to the reaction tube and incubated for 240 seconds.
    e. The clot time is measured up to a maximum time of 300 seconds.
6. The clot time is then correlated to the potency generated by the reference standard calibration curve.

Size-Exclusion (Sec) HPLC Method

An Agilent 1100 (Agilent Technologies, Santa Clara, Calif.) or a Waters Bioalliance HPLC system (Waters Corporation, Milford, Mass.) was and is typically used for the size exclusion method for determination of protein concentration. The typical size exclusion column used was a Superdex 200 from GE (Superdex 200 10.300 GL, 10×300 mm, Cat #17-5175-01 (GE Healthcare Lifesciences, Piscataway, N.J.)). A general assay protocol is as follows:
1. A typical mobile phase was prepared that contained 400 mM NaCl with 20 mM TRIS, pH 7.4 and 0.01% polysorbate 80.
2. The mobile phase was run through the HPLC system and column until equilibration of the baseline was observed.
3. Standards were run to establish system suitability with a typical run time of 30 minutes for each sample.
4. Samples were typically loaded onto an auto sampler with a control chamber temperature of 4° C.
5. A calibration standard of known concentrations containing various amounts of standard samples, typically from 1, 3, 5, 10 and 25 µg of protein were loaded onto the column in volumes between 10 to 50 µl.
6. Samples of unknown concentrations were also loaded into the columns typically in volumes between 30 to 50 µl.

7. The HPLC system was programmed to run the samples automatically according the sequence set up.
8. The peak area of the calibration standards and the unknown samples were determined based on fluorescence detection with excitation and emission at 280 nm and 340 nm respectively.
9. A linear regression of the calibration standards was generated and the concentration of the unknown sample was determined against this calibration curve.

Figure 3:
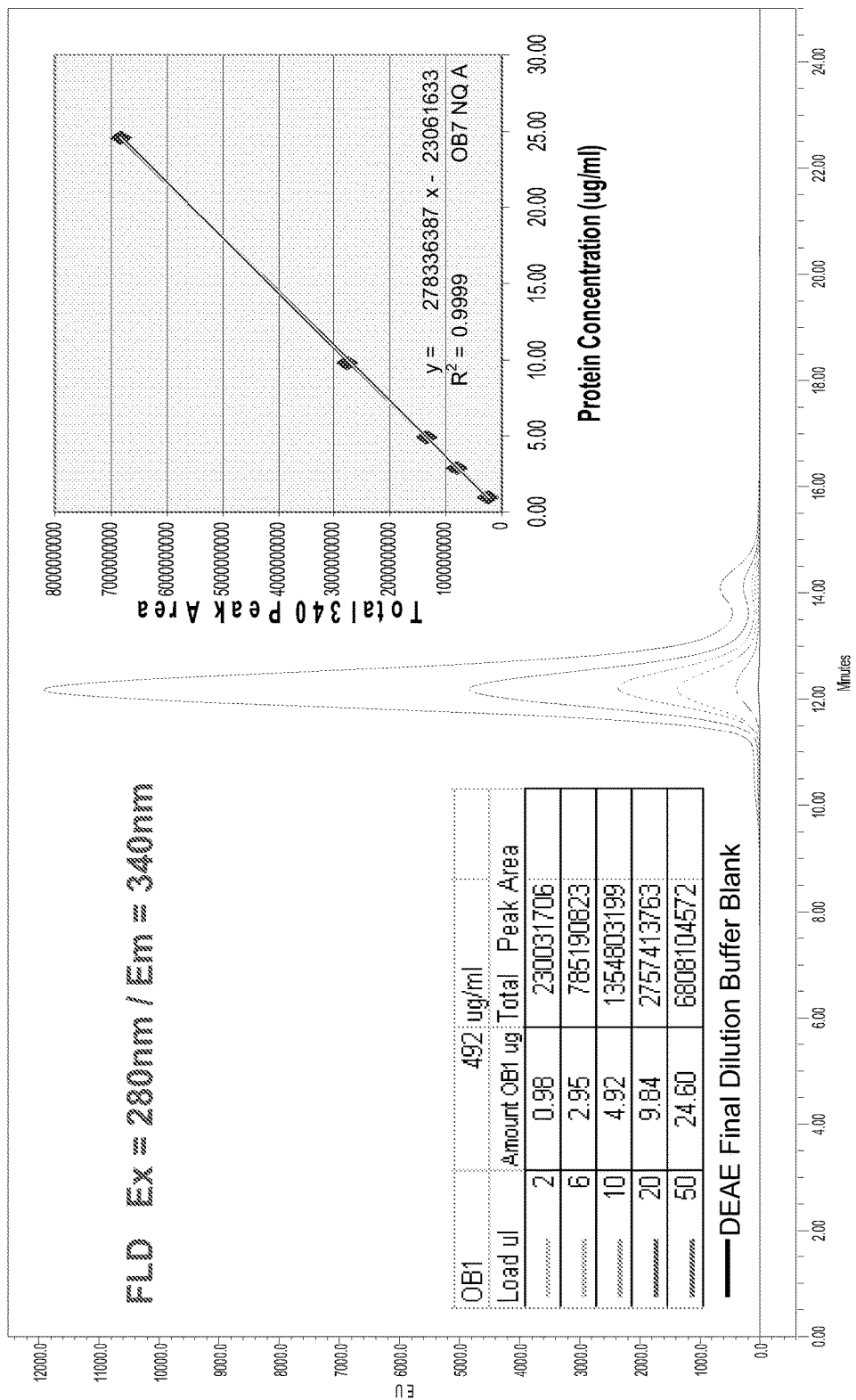
FIG. 3 shows typical example of the SEC profile of the calibration standards and the linear regression of the calibration curve as described in Example 5.

A typical example of the SEC profile of the calibration standards and the linear regression of the calibration curve is shown in FIG. 3.

Example 6

Binding to Von Willebrand Factor

Von Willebrand factor (vWF) is a multifunctional glycoprotein which circulates in plasma as a multimeric form complexed with Factor VIII (FVIII/vWF complex). The FVIII/vWF complex serves to protect the bound FVIII from early proteolysis in circulation in vivo.

Size exclusion chromatography (SEC) is used to characterize the binding in FVIII/vWF complexes. A Superose 6 column (Superose 6 10/300GL, GE Healthcare #17-5172-01, flow rate=0.5 mL/min) was selected for its known biocompatibility and high exclusion limit of 40 million Daltons (Mobile Phase formulation buffer: 2 mM CaCl2, 10 mM Tris pH 7.0, 300 mM NaCl, 0.01% PSB-80, 11 mM sucrose, 10 mM trisodium citrate). The differences in molecular weight between von Willebrand factor (dimeric @~500 KD, Fitzgerald Cat#30C-CP4003U, Lot # A09121050, Monomer Mol. Wt=~260 kD, Conc.=77 µg/mL) and rpFVIII (~160 KD) is sufficient to resolve the two species.

The stoichiometry of binding was determined by titration of constant amount of vWF with increasing amounts of rpFVIII. The profile of the complexation formation between rpFVIII and vWF was determined from the SEC chromatogram and integration of the appropriate peaks. The soluble form of the resultant mixtures in the supernatant were used to determine the end point of the complexation from titration with increasing amounts of rpFVIII. The larger, stable complexes formed between rpFVIII and vWF migrate from the normal retention time to the exclusion limit of the column. When saturation occurs, increasing amounts of unbound rpFVIII will be observed in the SEC chromatogram. This method is used to distinguish differences and similarities in the properties of the variants.

Example 7

Thrombin Digestion Kinetics

SDS-PAGE

Recombinant porcine factor VIII (rpFVIII) molecules are heterodimers of approximately 160 kD composed of a 78.5 kD molecular weight light chain (A3-C1-C2, 765-1448) and a heavy chain ranging in molecular weight from 86.7 kD (A1-A2). The heavy chain of rpFVIII is heterogeneous and composed of three main variants which are formed upon secretion from the cell and may be cleaved by membrane bound proteases of the subtilisin family designated PACE (Paired Basic Amino Acid Cleavage Enzyme).

Like the human factor VIII, rpFVIII is transformed into an active form by limited proteolysis from thrombin. Thrombin activation of rpFVIII is specific for the cleavage site of the heavy chain at Arg(372)-Ser(373). The cleavage region for the Light Chain at Arg(805)-Ser(806) liberates a small 40 amino acid peptide fraction ranging from 765-804 (~4.4 kD). The combination of these initial cleavages by thrombin form the activated recombinant porcine factor VIII as a heterotrimer of subunits designated as A1 (~50 kD), A2 (~40 kD), and A3-C1-C2 (~70 kD). The cleaved rpFVIII A1 and A3-C1-C2 subunits retain the divalent metal ion-dependent linkage, whereas the A2 subunit is weakly associated with the A1-A3-C1-C2 dimer by primarily electrostatic interactions. In SDS-PAGE, these subunits are displayed as three distinct bands. The efficiency in conversion of the rpFVIII (2 peptide units) to three peptide units is characteristic of thrombin activation of the product. This method distinguishes the similarity and differences between the individual variants.

Two other orthogonal methods can be and were used to map the kinetics of thrombin digestion of FVIII. Denaturing reverse phase HPLC may be used; the peak profiles are expected to be similar to that of SDS-PAGE. Anion exchange chromatography, which retains the native form of the peptides, may also be used.

Reverse Phase HPLC

Equipment:
1. HPLC 1100 series: Agilent Technologies, Santa Clara, Calif., USA; Model No. 61312A, Serial No. DE10907753.
2. Poroshell 5 um 2.1×75 mm column: Agilent Technologies, Santa Clara, Calif., USA; Part No. 660750-909, Serial No. USVV001988.

Reagents
1. Buffer A: 0.1% TFA (JT B Baker, Phillisburg, N.J.; Cat No. 94700-00, Lot No. J23J00) in water
2. Buffer B: 0.1% TFA in Acetonitrile (JT Baker, Phillisburg, N.J.; Cat No. 9017-03, Lot No. J38807).

Procedure:
1. Equilibrate the column for 60 minutes using 99% A and 1% B at 1 ml/min.
2. Sample injections were 50 µl in volume; 25 µl of reference standard was used as control.
3. An example of the method used to run the samples is shown Table 4.

TABLE 4

| Injection | Time (min) | Flow (ml/min) | % A | % B |
|---|---|---|---|---|
| 1 | 0.00 | 2 | 99 | 1 |
| 2 | 2.00 | 2 | 99 | 1 |
| 3 | 3.00 | 2 | 64 | 36 |
| 4 | 3.50 | 2 | 64 | 36 |
| 5 | 4.00 | 2 | 61 | 39 |
| 6 | 5.00 | 2 | 61 | 39 |
| 7 | 5.10 | 2 | 58 | 42 |
| 8 | 6.50 | 2 | 58 | 42 |
| 9 | 6.51 | 2 | 56 | 44 |
| 10 | 7.20 | 2 | 56 | 44 |
| 11 | 7.21 | 2 | 40 | 60 |
| 12 | 8.50 | 2 | 40 | 60 |
| 13 | 8.51 | 2 | 10 | 90 |
| 14 | 9.00 | 2 | 10 | 90 |
| 15 | 9.10 | 2 | 99 | 1 |
| 16 | 10.00 | 2 | 99 | 1 |

Anion Exchange Chromatography

Equipment:
1. AllianceBio HPLC, Waters corporation, Milford, Mass., USA; Model No. 2796; Serial No M08BA1199M.

2. Protein Pak Hi Res Q 5 um 4.6×100 mm column: Waters Corporation, Milford, Mass., USA; Part No. 186004931, Serial No. 502N112561VE04.

Reagents:
Buffer A:
10 mM Tris base (1.211 g/L)
2 mM Calcium Chloride (0.588 g/L)
0.01% polysorbate 80 (1 ml of 10% PS-80/L)
Filtered water up to 1 L, pH 7.0
Buffer B
10 mM Tris base (1.211 g/L)
2 mM Calcium Chloride (0.588 g/L)
0.01% polysorbate 80 (1 ml of 10% PS-80/L)
1M Sodium Chloride (58.44 g/L)
Filtered water up to 1 L, pH 7.0
Procedure:
1. Equilibrate the column for 60 min using 70% A and 30% B at 0.5 ml/min
2. Sample injections were 50 μl in volume; 10 μl of reference standard was used as control.
3. An example of the method used to run the samples is shown Table 5.

TABLE 5

| Injection | Time (min) | Flow (ml/min) | % A | % B |
|---|---|---|---|---|
| 1 | 0.01 | 0.5 | 70 | 30 |
| 2 | 0.50 | 0.5 | 70 | 30 |
| 3 | 3.50 | 0.5 | 60 | 40 |
| 4 | 5.00 | 0.5 | 60 | 40 |
| 5 | 10.00 | 0.5 | 30 | 70 |
| 6 | 10.10 | 0.5 | 1 | 99 |
| 7 | 12.00 | 0.5 | 1 | 99 |
| 8 | 12.10 | 0.5 | 70 | 30 |
| 9 | 17.00 | 0.5 | 70 | 30 |

The skilled artisan would know and appreciate that these and other methods may be used to arrive at understanding recombinant Factor VIII proteins as described herein.

The invention claimed is:

1. A polynucleotide encoding an isolated and recombinant, fully or partially B-domain deleted porcine factor VIII (FVIII) variant, the FVIII variant being devoid of an amino acid sequence corresponding to amino acids 714 to 740 of SEQ ID NO: 7.

2. An expression vector comprising a polynucleotide according to claim 1.

3. A mammalian cell comprising an expression vector according to claim 2.

4. A method for producing a FVIII variant, comprising the steps of:
   a. Culturing a mammalian cell according to claim 3; and
   b. Isolating from the mammalian cell the FVIII variant.

5. The method according to claim 4, further comprising the step of c. Formulating the factor VIII variant together with appropriate excipients into a pharmaceutical composition.

6. The polynucleotide of claim 1, wherein the FVIII variant comprises a sequence at least 90% identical to SEQ ID NO: 1, the variant being devoid of the amino acid sequence corresponding to amino acids 714 to 740 of SEQ ID NO: 7.

7. The polynucleotide of claim 6, wherein the FVIII variant shares at least 95% identity to SEQ ID NO: 1.

8. The polynucleotide of claim 7, wherein the FVIII variant shares at least 99.5% identity to SEQ ID NO: 1.

9. The polynucleotide of claim 8, wherein the FVIII variant is SEQ ID NO: 1.

10. The polynucleotide of claim 1, wherein the FVIII variant is partially B-domain deleted and the remaining portion of the B-domain is selected from a sequence consisting of SEQ ID NO: 4.

11. An expression vector comprising a polynucleotide according to claim 6.

12. An expression vector comprising a polynucleotide according to claim 7.

13. An expression vector comprising a polynucleotide according to claim 8.

14. An expression vector comprising a polynucleotide according to claim 9.

15. A mammalian cell comprising an expression vector according to claim 11.

16. A mammalian cell comprising an expression vector according to claim 12.

17. A mammalian cell comprising an expression vector according to claim 13.

18. A mammalian cell comprising an expression vector according to claim 14.

19. A method for producing a FVIII variant, comprising the steps of:
   a. Culturing a mammalian cell according to claim 16; and
   b. Isolating from the mammalian cell the FVIII variant.

20. A method for producing a FVIII variant, comprising the steps of:
   a. Culturing a mammalian cell according to claim 18; and
   b. Isolating from the mammalian cell the FVIII variant.

* * * * *